United States Patent
Smith et al.

(10) Patent No.: US 9,289,447 B2
(45) Date of Patent: Mar. 22, 2016

(54) CHEMOTHERAPEUTIC METHODS AND COMPOSITIONS

(75) Inventors: Victoria Smith, Burlingame, CA (US); Alison Kay Holzer, Redwood City, CA (US)

(73) Assignee: Gilead Biologics, Inc., Foster City, CA (US)

( * ) Notice: Subject to any disclaimer, the term of this patent is extended or adjusted under 35 U.S.C. 154(b) by 0 days.

(21) Appl. No.: 13/619,139

(22) Filed: Sep. 14, 2012

(65) Prior Publication Data

US 2013/0017207 A1    Jan. 17, 2013

Related U.S. Application Data

(62) Division of application No. 12/652,687, filed on Jan. 5, 2010, now Pat. No. 9,107,935.

(60) Provisional application No. 61/204,480, filed on Jan. 6, 2009.

(51) Int. Cl.
| | |
|---|---|
| A61K 39/395 | (2006.01) |
| A61K 31/7105 | (2006.01) |
| A61K 31/282 | (2006.01) |
| A61K 31/337 | (2006.01) |
| A61K 31/513 | (2006.01) |
| A61K 31/517 | (2006.01) |
| A61K 31/519 | (2006.01) |
| A61K 31/704 | (2006.01) |
| A61K 31/7068 | (2006.01) |
| A61K 33/24 | (2006.01) |
| A61K 45/06 | (2006.01) |
| C07K 16/40 | (2006.01) |
| C12N 15/113 | (2010.01) |

(52) U.S. Cl.
CPC ........... *A61K 31/7105* (2013.01); *A61K 31/282* (2013.01); *A61K 31/337* (2013.01); *A61K 31/513* (2013.01); *A61K 31/517* (2013.01); *A61K 31/519* (2013.01); *A61K 31/704* (2013.01); *A61K 31/7068* (2013.01); *A61K 33/24* (2013.01); *A61K 39/3955* (2013.01); *A61K 45/06* (2013.01); *C07K 16/40* (2013.01); *C12N 15/1137* (2013.01); *C12N 2310/14* (2013.01)

(58) Field of Classification Search
USPC .................. 424/146.1, 141.1, 130.1; 530/350
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber et al. |
| 4,098,876 A | 7/1978 | Piasio et al. |
| 4,331,647 A | 5/1982 | Goldenberg |
| 4,485,088 A | 11/1984 | Chvapil |
| 4,545,382 A | 10/1985 | Higgins et al. |
| 4,637,403 A | 1/1987 | Garcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagan et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,192,659 A | 3/1993 | Simons |
| 5,252,608 A | 10/1993 | Palfreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,641,484 A | 6/1997 | Hung et al. |
| 5,661,016 A | 8/1997 | Lonberg et al. |
| 5,712,170 A | 1/1998 | Kouvonen et al. |
| 5,721,138 A | 2/1998 | Lawn |
| 6,015,562 A | 1/2000 | Hinman et al. |

(Continued)

FOREIGN PATENT DOCUMENTS

| | | |
|---|---|---|
| EP | 0186087 | 8/1989 |
| EP | 0375408 | 6/1990 |

(Continued)

OTHER PUBLICATIONS

Fong et al. (Genes, Chromosomes & Cancer 2007, 46: 644-655).*

(Continued)

*Primary Examiner* — Yan Xiao
(74) *Attorney, Agent, or Firm* — Yu-Ming Dammann

(57) ABSTRACT

Disclosed herein are methods and compositions for enhancing the cell-killing activity of anti-neoplastic agents by inhibiting the activity of a lysyl oxidase-type enzyme. Also disclosed are methods for screening for chemotherapeutic agents, and for molecules that enhance the activity of chemotherapeutic agents, using cells grown on an extracellular matrix.

14 Claims, 24 Drawing Sheets

(56) References Cited

U.S. PATENT DOCUMENTS

| | | | |
|---|---|---|---|
| 6,140,056 A | 10/2000 | Khodadoust | |
| 6,225,118 B1 | 5/2001 | Grant et al. | |
| 6,277,622 B1 | 8/2001 | Weiss | |
| 6,300,092 B1 | 10/2001 | Khodadoust et al. | |
| 6,303,318 B1 | 10/2001 | O'Brien | |
| 6,316,416 B1 | 11/2001 | Patierno et al. | |
| 6,326,174 B1 | 12/2001 | Joyce et al. | |
| 6,352,862 B1 | 3/2002 | Davis et al. | |
| 6,391,602 B1 | 5/2002 | Khodadoust | |
| 6,534,261 B1 | 3/2003 | Cox, III et al. | |
| 6,808,707 B2 | 10/2004 | Ensley | |
| 7,112,668 B2 | 9/2006 | Rastelli et al. | |
| 7,208,300 B2 | 4/2007 | Evans et al. | |
| 7,255,856 B2 | 8/2007 | Li et al. | |
| 7,255,857 B2 | 8/2007 | Li et al. | |
| 7,335,294 B2 | 2/2008 | Heller et al. | |
| 7,348,170 B2 | 3/2008 | Yuuki et al. | |
| 7,396,920 B2 | 7/2008 | Hemmings et al. | |
| 7,445,920 B2 | 11/2008 | Evans et al. | |
| 7,585,634 B2 | 9/2009 | Kim et al. | |
| 8,163,494 B2 | 4/2012 | Neufeld et al. | |
| 8,168,180 B2 | 5/2012 | Neufeld et al. | |
| 8,461,303 B2 | 6/2013 | Smith et al. | |
| 8,512,990 B2 | 8/2013 | Mccauley et al. | |
| 8,658,167 B2 | 2/2014 | Smith et al. | |
| 8,679,485 B2 | 3/2014 | Smith et al. | |
| 8,680,246 B2 | 3/2014 | Mccauley et al. | |
| 8,815,823 B2 | 8/2014 | Neufeld et al. | |
| 2001/0005581 A1 | 6/2001 | Grant et al. | |
| 2001/0012890 A1 | 8/2001 | Thompson | |
| 2002/0072089 A1 | 6/2002 | Holtzman et al. | |
| 2002/0123476 A1 | 9/2002 | Emanuele et al. | |
| 2002/0128218 A1 | 9/2002 | Emanuele et al. | |
| 2002/0151007 A1 | 10/2002 | Khodadoust et al. | |
| 2002/0156263 A1 | 10/2002 | Chen | |
| 2003/0008023 A1 | 1/2003 | Lu | |
| 2003/0017068 A1 | 1/2003 | Larrain et al. | |
| 2003/0092037 A1 | 5/2003 | Matsuzaki et al. | |
| 2003/0096980 A1 | 5/2003 | Froehler et al. | |
| 2003/0099213 A1 | 5/2003 | Lee et al. | |
| 2003/0114410 A1 | 6/2003 | Neufeld et al. | |
| 2003/0129672 A1 | 7/2003 | Dyer et al. | |
| 2003/0149997 A1 | 8/2003 | Hageman | |
| 2003/0152926 A1 | 8/2003 | Murray et al. | |
| 2003/0211076 A1 | 11/2003 | Li et al. | |
| 2004/0009154 A1 | 1/2004 | Khan et al. | |
| 2004/0029114 A1 | 2/2004 | Mack et al. | |
| 2004/0156854 A1 | 8/2004 | Mulligan et al. | |
| 2004/0171110 A1 | 9/2004 | Evans et al. | |
| 2004/0176296 A1 | 9/2004 | Holtzman et al. | |
| 2004/0197328 A1 | 10/2004 | Young et al. | |
| 2004/0213756 A1 | 10/2004 | Michal et al. | |
| 2004/0248871 A1 | 12/2004 | Farjanel et al. | |
| 2004/0253220 A1 | 12/2004 | Perrier et al. | |
| 2004/0253606 A1 | 12/2004 | Aziz et al. | |
| 2004/0258676 A1 | 12/2004 | Perrier et al. | |
| 2004/0265230 A1 | 12/2004 | Martinez et al. | |
| 2005/0020521 A1 | 1/2005 | Rana et al. | |
| 2005/0079538 A1 | 4/2005 | Griffin et al. | |
| 2005/0119202 A1 | 6/2005 | Kreutzer et al. | |
| 2005/0181375 A1 | 8/2005 | Aziz et al. | |
| 2005/0259483 A1 | 11/2005 | Nakamura et al. | |
| 2005/0260639 A1 | 11/2005 | Nakamura et al. | |
| 2006/0019256 A1 | 1/2006 | Clarke et al. | |
| 2006/0083736 A1 | 4/2006 | Law et al. | |
| 2006/0088532 A1 | 4/2006 | Alitalo et al. | |
| 2006/0088882 A1 | 4/2006 | Jain et al. | |
| 2006/0127402 A1* | 6/2006 | Neufeld et al. | 424/146.1 |
| 2006/0127902 A1 | 6/2006 | Madden et al. | |
| 2006/0134172 A1 | 6/2006 | Shepard et al. | |
| 2006/0134801 A1 | 6/2006 | Chada et al. | |
| 2006/0188889 A1 | 8/2006 | Burgess et al. | |
| 2006/0216722 A1 | 9/2006 | Betholtz et al. | |
| 2006/0223760 A1 | 10/2006 | Li et al. | |
| 2007/0010469 A1 | 1/2007 | Chan et al. | |
| 2007/0021365 A1 | 1/2007 | Erler et al. | |
| 2007/0037203 A1 | 2/2007 | Kapeller-Libermann et al. | |
| 2007/0054278 A1 | 3/2007 | Cargill | |
| 2007/0059745 A1 | 3/2007 | Sharp et al. | |
| 2007/0148173 A1 | 6/2007 | Huang et al. | |
| 2007/0154481 A1 | 7/2007 | Gelinas et al. | |
| 2007/0184439 A1 | 8/2007 | Guilford et al. | |
| 2007/0197424 A1 | 8/2007 | Friedman et al. | |
| 2007/0225242 A1 | 9/2007 | Erler et al. | |
| 2007/0231323 A1 | 10/2007 | Phillips | |
| 2007/0243214 A1 | 10/2007 | Schiemann et al. | |
| 2008/0031817 A1 | 2/2008 | Mazar et al. | |
| 2008/0118928 A1 | 5/2008 | Hageman | |
| 2008/0137893 A1 | 6/2008 | Ross et al. | |
| 2008/0181896 A1 | 7/2008 | Khan et al. | |
| 2008/0187523 A1 | 8/2008 | Zhang et al. | |
| 2008/0220424 A1 | 9/2008 | Haber et al. | |
| 2008/0248477 A1 | 10/2008 | Holtzman et al. | |
| 2008/0261870 A1 | 10/2008 | Trackman et al. | |
| 2008/0274453 A1 | 11/2008 | Hageman | |
| 2008/0279857 A1 | 11/2008 | Skerry et al. | |
| 2008/0286808 A1 | 11/2008 | Schellenberger et al. | |
| 2008/0292547 A1 | 11/2008 | Tolleshaug et al. | |
| 2008/0305965 A1 | 12/2008 | Moorhouse et al. | |
| 2009/0022703 A1 | 1/2009 | Li et al. | |
| 2009/0023149 A1 | 1/2009 | Knudsen et al. | |
| 2009/0035348 A1 | 2/2009 | Zadini et al. | |
| 2009/0053224 A1* | 2/2009 | Smith et al. | 424/135.1 |
| 2009/0104201 A1 | 4/2009 | Smith et al. | |
| 2009/0142301 A1 | 6/2009 | Bevec et al. | |
| 2009/0232773 A1 | 9/2009 | Kato et al. | |
| 2009/0233270 A9 | 9/2009 | St. Croix et al. | |
| 2009/0239947 A1 | 9/2009 | Dai et al. | |
| 2009/0275633 A1 | 11/2009 | Esteller | |
| 2010/0119515 A1 | 5/2010 | Neufeld et al. | |
| 2010/0144603 A1 | 6/2010 | Watnick | |
| 2010/0203062 A1 | 8/2010 | Stalmans et al. | |
| 2010/0209415 A1* | 8/2010 | Smith et al. | 424/130.1 |
| 2010/0317721 A1 | 12/2010 | Neufeld | |
| 2011/0044907 A1 | 2/2011 | Marshall et al. | |
| 2011/0044981 A1 | 2/2011 | Spangler et al. | |
| 2011/0076272 A1 | 3/2011 | Smith et al. | |
| 2011/0076285 A1 | 3/2011 | Stalmans et al. | |
| 2011/0076739 A1 | 3/2011 | McCauley et al. | |
| 2011/0200606 A1 | 8/2011 | McCauley et al. | |
| 2011/0207144 A1 | 8/2011 | Marshall et al. | |
| 2012/0087917 A1 | 4/2012 | Smith et al. | |
| 2012/0165398 A1 | 6/2012 | Neufeld et al. | |
| 2012/0202206 A1 | 8/2012 | Neufeld et al. | |
| 2012/0309020 A1 | 12/2012 | Smith et al. | |
| 2013/0017207 A1 | 1/2013 | Smith et al. | |
| 2013/0022617 A1 | 1/2013 | Neufeld | |
| 2013/0095101 A1 | 4/2013 | Smith et al. | |
| 2013/0157361 A1 | 6/2013 | Mccauley et al. | |
| 2013/0324705 A1 | 12/2013 | Smith et al. | |
| 2014/0079707 A1 | 3/2014 | Smith et al. | |
| 2014/0120102 A1 | 5/2014 | Bornstein et al. | |
| 2014/0128284 A1 | 5/2014 | Smith et al. | |
| 2014/0186340 A1 | 7/2014 | Marshall et al. | |
| 2014/0206017 A1 | 7/2014 | Smith et al. | |
| 2014/0255951 A1 | 9/2014 | Mccauley et al. | |
| 2014/0302524 A1 | 10/2014 | Mccauley et al. | |

FOREIGN PATENT DOCUMENTS

| | | |
|---|---|---|
| EP | 0799891 | 10/1997 |
| EP | 0960192 | 12/1999 |
| EP | 1149169 | 10/2001 |
| EP | 1616881 | 1/2006 |
| EP | 1690932 | 8/2006 |
| EP | 1693448 | 8/2006 |
| EP | 1715035 | 10/2006 |
| EP | 2078531 | 7/2009 |
| EP | 1315519 B1 | 12/2010 |
| EP | 2467162 | 6/2012 |
| EP | 2470218 | 7/2012 |
| WO | WO-89/12060 | 12/1989 |
| WO | WO-92/20702 | 11/1992 |
| WO | WO-96/00614 | 1/1996 |

(56) References Cited

FOREIGN PATENT DOCUMENTS

| WO | WO-96/40746 | 12/1996 |
|---|---|---|
| WO | WO-97/00441 | 1/1997 |
| WO | WO-98/06830 | 2/1998 |
| WO | WO-99/65928 | 12/1999 |
| WO | WO-00/44910 | 8/2000 |
| WO | WO-01/83702 | 11/2001 |
| WO | WO-01/92495 | 12/2001 |
| WO | WO-02/11667 | 2/2002 |
| WO | WO-02/061092 | 8/2002 |
| WO | WO-02/079492 | 10/2002 |
| WO | WO-02/086443 | 10/2002 |
| WO | WO-03/031939 | 4/2003 |
| WO | WO-03/100016 | 12/2003 |
| WO | WO-2004/023973 | 3/2004 |
| WO | WO-2004/047720 | 6/2004 |
| WO | WO-2004/061423 | 7/2004 |
| WO | WO-2004/091655 | 10/2004 |
| WO | WO-2005/100604 | 10/2005 |
| WO | WO-2006/128740 | 7/2006 |
| WO | WO-2007/045927 | 4/2007 |
| WO | WO-2007/126457 | 11/2007 |
| WO | WO 2007/146172 | 12/2007 |
| WO | WO-2008/063479 | 5/2008 |
| WO | WO-2008/070616 | 6/2008 |
| WO | WO-2008/132453 | 11/2008 |
| WO | WO-2008/138578 | 11/2008 |
| WO | WO-2009/010974 | 1/2009 |
| WO | WO-2009/017833 | 2/2009 |
| WO | WO-2009/035791 | 3/2009 |
| WO | WO-2010/080769 | 7/2010 |
| WO | WO-2010/091279 | 8/2010 |
| WO | WO-2011/022667 | 2/2011 |
| WO | WO-2011/022670 | 2/2011 |
| WO | WO-2011/022706 | 2/2011 |
| WO | WO-2011/022709 | 2/2011 |
| WO | WO-2011/022710 | 2/2011 |
| WO | WO-2011/041309 | 4/2011 |
| WO | WO-2011/097513 | 8/2011 |
| WO | WO-2012/139045 | 10/2012 |
| WO | WO-2012/167181 | 12/2012 |
| WO | WO 2014/070939 | 5/2014 |

OTHER PUBLICATIONS

Tannock, I.F. (Experimental Chemotherapy, Ch. 19; p. 338 and 352-359, in The Basic Science of Oncology, Tannock and Hill, eds., New York 1992).*
Harmsen and Haard (Appl Microbiol Biotechnol 2007, 77:13-22).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Jiang et al. (J. Biol. Chem. Feb. 11, 2005; 280 (6): 4656-4662).*
Stancoviski et al. (Proceedings of the National Academy of Science USA. 1991; 88: 8691-8695).*
Decision to Grant for EP 10012458.5 dated Sep. 12, 2013.
Search Report and Written Opinion for SN 201201215-9 mailed Jul. 19, 2013.
First Office Action (translation) for CN 201080047970.7 mailed Jul. 26, 2013.
Kraus et al. (2006) "CSMD1 Is a Novel Multiple Domain Complement-Regulatory Protein Highly Expressed in the Central Nervous System and Epithelial Tissues" J. Immunol. 176:4419-4430.
Final Office Action for U.S. Appl. No. 13/021,555, mailed Jul. 19, 2013.
Final Office Action for U.S. Appl. No. 12/860,834, mailed Jul. 26, 2013.
Final Office Action for U.S. Appl. No. 12/652,687, mailed Aug. 1, 2013.
Notice of Allowance (translation) for JP 2010-519263, mailed Jun. 21, 2013.
Advisory Action for U.S. Appl. No. 12/185,054 mailed Aug. 20, 2013.
Office Action (translation) for JP 2010-519951 mailed Jul. 12, 2013.
Decision on Rejection (translation) for CN 200880101321.3 mailed Jul. 3, 2013.
First Office Action (translation) for CN 201080047979.8 mailed Jun. 28, 2013.
Non-Final Office Action for U.S. Appl. No. 13/487,109 mailed Aug. 8, 2013.
American Thoracic Society International Consensus Statement (2000) "Idiopathic Pulmonary Fibrosis: Diagnosis and Treatment" Am J Respir Grit Care Med 161:646-664.
Peng et al. (2009) "Secreted LOXL2 is a Novel Therapeutic Target that Promotes Gastric Cancer Metastasis via the Src/FAK Pathway," Carcinogenesis 30(10):1660-1669.
Schietke et al., Journal of Biological Chemistry vol. 285, No. 9, pp. 6658-6669, Feb. 26, 2010, Published, JBC Papers in Press, Dec. 21, 2009.
Final Office Action mailed May 10, 2013 in U.S. Appl. No. 12/185,054.
Office Action mailed Apr. 2, 2013, in U.S. Appl. No. 13/707,495.
Notice of Allowance mailed Feb. 6, 2013, in U.S. Appl. No. 12/185,050.
Notice of Reasons for Rejection (translation) mailed Feb. 1, 2013 for JP 2010-519263.
First Examination Report mailed Apr. 4, 2013, in NZ 601615.
Communication Pursuant to Rules 70(2) and 70a(2) EPC mailed Mar. 22, 2013, for EP 10810702.0.
Fujimoto et al. (2009) "Reciprocal Regulation of LOX and LOXL2 Expression During Cell Adhesion and Terminal Differentiation in Epidermal Keratinocytes," Journal of Dermatological Science 55(2):91-98.
U.S. Appl. No. 12/860,632, filed Aug. 2011, Marshall et al.
U.S. Appl. No. 13/021,555, filed Aug. 2011, McCauley et al.
Office Action mailed Sep. 23, 2010 in U.S. Appl. No. 12/185,054.
Office Action mailed Feb. 15, 2011 in U.S. Appl. No. 12/185,054.
International Preliminary Report on Patentability Chapter I issued Feb. 2, 2010, in PCT/US2008/009354.
Written Opinion of the ISA mailed Apr. 29, 2009, in PCT/US2008/009354.
Invitation to Pay Additional Fees mailed Jan. 14, 2009 (including Annex Communication Relating to the Results of Partial International Search), in PCT/US2008/009354.
Communication pursuant to Article 94(3) EPC dated Jun. 8, 2010, in EP 08795003.6-1222.
Communication pursuant to Article 94(3) EPC dated Jul. 19, 2011, in EP 08795003.6-1222.
Communication under Rule 71(3) EPC dated Jul. 23, 2012, in EP 08795003.6-1222.
Patent Examination Report No. 1 for AU 2008282739, issued Nov. 19, 2012.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.

(56) References Cited

OTHER PUBLICATIONS

International Preliminary Examination Report mailed Dec. 8, 2003, in PCT/IL01/00728.
Written Opinion mailed Jun. 6, 2003, in PCT/IL01/00728.
Invitation to Pay Additional Fees mailed May 23, 2002, in PCT/IL01/00728.
Invitation to Pay Additional Fees mailed Jun. 13, 2005, in PCT/IL03/01008.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
Communication pursuant to Article 94(3) EPC mailed May 29, 2008, in EP 03777136.7-1222.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
Communication pursuant to Article 94(3) EPC mailed Dec. 27, 2011, in EP 08020753.3-1222.
Office Action mailed Sep. 23, 2010, in U.S. Appl. No. 12/185,050.
Office Action mailed Feb. 15, 2011, in U.S. Appl. No. 12/185,050.
International Preliminary Report on Patentability Chapter I issued May 11, 2010, in PCT/US2008/072039.
Written Opinion of the Isa mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Communication pursuant to Article 94(3) EPC for EP 08 830 207.0, mailed Nov. 22, 2012.
Notice on the Second Office Action (translation) for CN 200880101321.3, mailed Nov. 23, 2012.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.
Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
Communication pursuant to Rules 70(2) and 70a(2) EPC for EP 10739181.5, mailed Nov. 5, 2012.
Notice of Allowance for U.S. Appl. No. 12/860,625, mailed Nov. 23, 2012.
International Preliminary Report on Patentability Chapter I issued Feb. 21, 2012, in PCT/US2010/046192.
Written Opinion of the ISA mailed Feb. 17, 2011, in PCT/US2010/046192.
Invitation to Pay Additional Fees mailed Nov. 18, 2010, in PCT/US2010/046192.
Examination Report for NZ 598466, mailed Nov. 5, 2012.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
Office Action mailed Jul. 12, 2012, in U.S. Appl. No. 12/860,693.
Final Office Action for U.S. Appl. No. 12/860,693, mailed Nov. 15, 2012.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Preliminary Report on Patentability Chapter I issued Feb. 21, 2012, in PCT/US2010/046244.
Written Opinion of the ISA mailed Feb. 8, 2011, in PCT/US2010/046244.
Invitation to Pay Additional Fees mailed Dec. 3, 2010, in PCT/US2010/046244.
Examination Report for NZ 598464, mailed Nov. 5, 2012.
Written Opinion of the ISA mailed Jun. 14, 2012, in PCT/US2012/032600.
Written Opinion of the ISA mailed Aug. 10, 2012, in PCT/US2012/037580.
Written Opinion of the ISA mailed Sep. 10, 2012, in PCT/US2012/040585.
"The role of the Extracellular Matrix in Cancer," Mar. 2001, U.S. Department of Energy: http:www.science.doe.gov/Accomplishments_Awards/Decades_Discovery/85.html.
Adamson et al. (1974) "The Pathogenesis of Bleomycin-Induced Pulmonary Fibrosis in Mice" Am. J. Pathol. 77(2):185-189.
Akagawa et al. (2007) "Systematic Screening of Lysyl Oxidase-like (LOXL) Family Genes Demonstrates that LOXL2 is a Susceptibility Gene to Intracranial Aneurysms." Hum Genet 121(3-4): 377-87.
Akhtar et al. (2002) "The Sponge/Matrigel Angiogenesis Assay" Angiogenesis 5(1-2):75-80.
Akiri et al. (2003) "Lysyl Oxidase-Related Protein-1 Promotes Tumor Fibrosis and Tumor Progression in Vivo" Cancer Res. 63(7):1657-1666.
Albini et al. (1987) "A Rapid in Vitro Assay for Quantitating the Invasive Potential of Tumor Cells" Cancer Res. 47(12):3239-3245.
Albini et al. (2004) "The chemoinvasion assay: a tool to study tumor and endothelial cell invasion of basement membranes," Int. J. Dev. Biol. 48:563-571.
Aplin et al. (1998) "Signal transduction and signal modulation by cell adhesion receptors: the role of integrins, cadherins, immunoglobulin-cell adhesion molecules, and selectins" Pharmacol Rev. 50(2):197-263.

(56) References Cited

OTHER PUBLICATIONS

Arguello et al.(1992) "Incidence and Distribution of Experimental Metastases in Mutant Mice with Defective Organ Microenvironments (Genotypes Sl/Sld and W/Wv)" Cancer Research 52(8):2304-2309.
Armstrong et al. (1999) "Changes in Collagen Turnover in Early Acute Respiratory Distress Syndrome," Am. J. Respir. Crit. Care Med. 160:1910-1915.
Asuncion et al. (2001) "A Novel Human Lysyl Oxidase-Like Gene (LOXL4) on Chromosome 10q24 Has an Altered Scavenger Receptor Cysteine Rich Domain" Matrix Biol. 20(7):487-491.
Atabani, et al. (1997) "Identification of an Immunodominant Neutralizing and Protective Epitope from Measles Virus Fusion Protein by Using Human Sera from Acute Infection" J. Virology 71(10):7240-7245.
Atsawasuwan et al. (2005) "Expression of lysyl oxidase isoforms in MC3T3-E1 osteoblastic cells." Biochem Biophys Res Commun 327(4): 1042-6.
Atsawasuwan et al. (2008) "Lysyl oxidase binds transforming growth factor-β and regulates its signaling via amine oxidase activity." J Biol Chem 283(49): 34229-40.
Auerbach et al. (1974) "A simple procedure for the long-term cultivation of chicken embryos" Devel. Biol. 41(2):391-394.
Auerbach et al. (2003) "Angiogenesis Assays: A Critical Overview" Clinical Chemistry 49(1):32-40.
Barker, et al. (2011) "LOXL2-mediated matrix remodeling in metastasis and mammary gland involution" Cancer Res., 71(5):1561-1572.
Barry-Hamilton et al. (2010) "Allosteric inhibition of lysyl oxidase-like-2 impedes the development of a pathologic microenvironment" Nat.Med. 19(9):1009-1017.
Barzu et al. (1993) "Characterization of B-Cell Epitopes on IpaB, an Invasion-Associated Antigen of Shigella flexneri: Identification of an Immunodominant Domain Recognized during Natural Infection" Infection and Immunity, vol. 61, No. 9, pp. 3825-3831.
Bedogni et al. (2004) "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice" Cancer Res. 64(7):2552-2560.
Beilmann et al. (2004) "Human primary co-culture angiogenesis assay reveals additive stimulation and different angiogenic properties of VEGF and HGF" Cytokine 26(4):178-185.
Bendig (1995) "Humanization of Rodent Monoclonal Antibodies by CDR Grafting" Methods: Companion to Methods in Enzymology 8:83-93.
Berger et al. (2004) "A murine model of ex vivo angiogenesis using aortic disks grown in fibrin clot" Microvascular Res. 68(3):179-187.
Berithaupt et al. (2008) "Demyelinating Myelin Oligodendrocyte Glycoprotein-Specific Autoantibody Response Is Focused on one Dominant Conformational Epitope Region in Rodents" J. Immunology 181(2):1255-1263.
Betakova et al. (1998) "Monoclonal Anti-Idiotypic Antibodies Mimicking the Immunodominant Epitope of Influenza Virus Haemagglutinin Elicit Biologically Significant Immune Responses" J. Gen. Virology 79:461-470.
Bhowmick et al. (2004) "Stromal fibroblasts in cancer initiation and progression." Nature 432(7015): 332-7.
Blacher et al. (2001) "Improved quantification of angiogenesis in the rat aortic ring assay" Angiogenesis 4(2):133-142.
Blast 2 Sequences (LOR-1 and LOR-2) results version BLASTP 2.2.14, Apr. 9, 2006.
Boneberg et. al. (2009) "Angiogenesis and lymphangiogenesis are downregulated in primary breast cancer" Br. J. Cancer, 101(4):605-614.
Borel et al. (2001) "Lysyl Oxidase-Like Protein from Bovine Aorta. Isolation and Maturation to an Active Form by Bone Morphogenetic Protein-1" J. Biol. Chem. 276(52):48944-48949.

Bouez, et al. (2006) "The Lysyl Oxidase LOX is Absent in Basal and Squamous Cell Carcinomas and its Knockdown Induces an Invading Phenotype in a Skin Equivalent Model" Clinical Cancer Res. 12(5) 1463-1469.
Brody, et al. (1976) "Lung lysyl oxidase and elastin synthesis during compensatory lung growth" Chest 69(2 Suppl):271-272.
Bronson et al. (2005) "LOXL Null Mice Demonstrate Selective Dentate Structural Changes but Maintain Dentate Granule Cell and CA1 Pyramidal Cell Potentiation in the Hippocampus" Neurosci. Lett. 390(2):118-122.
Brown et al. (1996) "A novel in vitro assay for human angiogenesis" Laboratory Investigation 75(4):539-555.
Brown et al. (2004) "Exploiting Tumour Hypoxia in Cancer Treatment" Nature Reviews 4:437-447.
Brukamp et al. (2007) "Hypoxia and Podocyte-Specific Vhlh Deletion Confer Risk of Glomerular Disease" Am. J. Physiol. Renal. Physiol. 293(4):F1397-F1407.
Bruns et al. (2000) "Vascular Endothelial Growth Factor Is an In Vivo Survival Factor for Tumor Endothelium in a Murine Model of Colorectal Carcinoma Liver Metastases" Cancer, 89(3):488-499.
Burbelo et al. (1986) "Monoclonal Antibodies to Human Lysyl Oxidase" Coll. Relat. Res. 6(2):153-62.
Butcher et al. (2009) "A Tense Situation: Forcing Tumour Progression" Nat. Rev. Cancer 9(2):108-122.
Cairns et al. (2004) "Acute Hypoxia Enhances Spontaneous Lymph Node Metastasis in an Orthotopic Murine Model of Human Cervical Carcinoma" Cancer Res. 64:2054-2061.
Campbell, Monoclonal Antibody Technology, 1984, Chapter 1, pp. 1-32.
Cancer Reference Information; Detailed guide: Breast cancer, how is breast cancer diagnosed? www.cancer.org/docroot/CRI_2_4_3X_How_is_breast_cancer_diagnosed, Nov. 16, 2009.
Cardone et al. (1997) "Prognostic value of desmoplastic reaction and lymphocytic infiltration in the management of breast cancer." Panminerva Med 39(3): 174-7.
Castera (2011) "Invasive and Non-Invasive Methods for the Assessment of Fibrosis and Disease Progression in Chronic Liver Disease," Best Pract. Res. Clin. Gastroent. 25:291-303.
Chan et al. (2007) "Hypoxia, Gene Expression, and Metastasis" Cancer Metastasis Rev. 26(2):333-339.
Chang & Werb (2001) "The Many Faces of Metalloproteases: Cell Growth, Invasion, Angiogenesis and Metastasis" Trends Cell. Biol. 11(11):537-43.
Chang et al. (2004) "Gene expression signature of fibroblast serum response predicts human cancer progression: similarities between tumors and wounds" PLoS Biol. 2(2):206-213.
Chanoki, et al. (1995) "Increased Expression of Lysyl Oxidase in Skin with Scleroderma" Br. J. Dermatol. 133(5):710-5.
Chen (2005) "Boyden chamber assay" Methods Mol. Biol. 294:15-22.
Chichester et al. (1981) "Lung lysyl oxidase and prolyl hydroxylase: increases induced by cadmium chloride inhalation and the effect of β-aminopropionitrile in rats." Am Rev Respir Dis 124(6): 709-13.
Chioza, et al. (2001) "Mutations in the lysyl oxidase gene are not associated with amyotrophic lateral sclerosis." Amyotroph Lateral Soler Other Motor Neuron Disord 2(2): 93-7.
Chow et al. (2000) "Identification and Expression of an Allergen Asp f 13 from Aspergillus Fumigatus and Epitope Mapping Using Human IgE Antibodies and Rabbit Polyclonal Antibodies," Biochem. J, vol. 346, pp. 423-431.
Christiansen & Rajasekaran (2006) "Reassessing Epithelial to Mesenchymal Transition as a Prerequisite for Carcinoma Invasion and Metastasis" Cancer Res., 66(17):8319-26.
Christiansen et al. (2004) "Biological Impediments to Monoclonal Antibody-Based Cancer Immunotherapy" Mol. Cancer Ther. 3(11):1493-1501.
Chu & Peters (2008) "Serial analysis of the vascular endothelial transcriptome under static and shear stress conditions." Physiol Genomics 34(2): 185-92.
Chu, et al. (2008) "Glycogen synthase kinase-3l3 regulates DeltaNp63 gene transcription through the β-catenin signaling pathway." J Cell Biochem 105(2): 447-53.

(56) References Cited

OTHER PUBLICATIONS

Chua et al. (2005) "Pulmonary Fibrosis Searching for Model Answers," Am J. Respir. Cell. Mol. Biol. 33:9-13.
Colman (1994) "Effects of Amino Acid Sequence Changes on Antibody-Antigen Interactions" Res. Immunol. 145(1):33-36.
Conti, et al. (2008). "The desmoplastic reaction surrounding hepatic colorectal adenocarcinoma metastases aids tumor growth and survival via alphav integrin ligation." Clin Cancer Res 14(20): 6405-13.
Csiszar (2001) "Lysyl Oxidases: a Novel Multifunctional Amine Oxidase Family" Prog. Nucl. Acid Res. 70:1-32.
Csiszar (2002) "Somatic Mutation of the Lysyl Oxidase Gene on Chromosome S023.1 in Colorectal Tumors" Int. J. Cancer 97:636-642.
Csiszar et al. (1996) "Functional analysis of the promoter and first intron of the human lysyl oxidase gene." Mol Biol Rep 23(2): 97-108.
Database EMBL [Online] Oct. 28, 2008, "Sequence 15133 from Patent WO2004061423", retrieved from EBI accession No. EMBL:FB530075, Database accession No. FB530075.
Database Geneseq (Derwent, London, UK), Accession No. A13B07649, Feb. 14, 2002, 99.9% identical to SEQ ID No. 2.
Database Issued Patents (United States Patent & Trademark Office, Alexandria, VA) U.S. Pat. No. 6,300,092. Oct. 9, 2001, 99.9% identical to SEQ ID No. 2.
De Eguileor et al. (2004) "Hirudo medicinalis: avascular tissues for clear-cut angiogenesis studies?" Current Pharmaceutical Design 10(16):1979-1998.
Decitre et al. (1998) "Lysyl oxidase-like protein localizes to sites of de novo fibrinogenesis in fibrosis and in the early stromal reaction of ductal breast carcinomas" Lab. Invest. 78(2):143-151.
Denko et al. (2003) "Investigating Hypoxic Tumor Physiology through Gene Expression Patterns" Oncogene 22:5907-5914.
Dermer (1994) "Another Anniversary for the War on Cancer" Biotechnology 12:320.
Dillman (1989) "Monoclonal antibodies for treating cancer" Ann. Intern. Med. 111(7):592-603.
Entrez Gene data base searching result in National Library of Medicine. 2010.
Erler et al. (2004) "The role of Hypoxia-Induced Lysyl Oxidase in Cancer Progression, Tumor Response to Therapy and Patient Prognosis" Eur. J. Cancer Suppl. 2(8):190.
Erler et al. (2006) "Lysyl Oxidase is Essential for Hypoxia-Induced Metastasis" Pro. Amer. Assoc. Cancer Res. 47:Abstract 2409.
Erler et al. (2005) "Hypoxia promotes invasion and metastasis of breast cancer cells by increasing lysyl oxidase expression" Breast Cancer Res. 7 (Suppl 2):P5.05.
Erler et al. (2006) "12 LOX is Essential for Hypoxia-Induced Metastasis" Radiother. Oncol. 78:S5.
Erler et al. (2006) "Lysyl Oxidase is Essential for Hypoxia-Induced Metastasis" Nature 440(7088):1222-1226.
Erler et al. (2006) "Lysyl Oxidase Mediates Hypoxic Control of Metastasis" Cancer Res. 66(21):10238-10241.
Erler et al. (2009) "Hypoxia-induced lysyl oxidase is a critical mediator of bone marrow cell recruitment to form the premetastatic niche." Cancer Cell 15(1): 35-44.
Evans et al. (1999) "Vaccine Therapy for Cancer—Fact or Fiction?" QJM. 92(6):299-307.
Example from Wikipedia, the free encyclopedia, "Monoclonal Antibody Therapy," (http://en.wikipedia.org/wiki/Antibody_therapy), accessed on Oct. 4, 2010.
Example of the USPTO's Written Description Training Materials, Revision 1, Mar. 25, 2008, 84 pages in length.
Ferrari et al. (1991) "Identification of Immunodominant T Cell Epitopes of the Hepatitis B Virus Nucleocapsid Antigen" J. Clin. Invest. 88(1):214-222.
Fidler et al. (1994) "The implications of angiogenesis for the biology and therapy of cancer metastasis" Cell 79(2):185-188.
Fodstad et al. (1988) "A New Experimental Metastasis Model in Athymic Nude Mice, the Human Malignant Melanoma Lox" Intl. J. Cancer 41:442-449.A216.

Fogelgren et al. (2005) "Cellular fibronectin binds to lysyl oxidase with high affinity and is critical f its proteolytic activation" J Biol. Chem. 280(26):24690-24697.
Fong et al. (2007) "Lysyl oxidase-like 2 expression is increased in colon and esophageal tumors and associated with less differentiated colon tumors" Genes, Chromosomes and Cancer vol. 46(7):644-655.
Freshney (1983) Culture of Animal Cells: A Manual of Basic Technique, Alan R. Liss Inc.: NY:4.
Gacheru et al. (1997) "Transcriptional and post-transcriptional control of lysyl oxidase expression in vascular smooth muscle cells: effects of TGF-beta1 and serum deprivation." J Cell Biochem 65(3): 395-407.
Gelatt (1977) "Animal models for glaucoma" Invest. Ophthalmol. Visual Sci. 16(7):592-596.
GenBank Public DNA Database Accession No. AAA59525.1 "Lysyl Oxidase [*Homo sapiens*]", Jan. 7, 1995.
GenBank Public DNA Database Accession No. AAA59541.1 "Lysyl Oxidase [*Homo sapiens*]", Jan. 7, 1995.
GenBank Public DNA Database Accession No. AAB21243.1 "Lysyl Oxidase [*Homo sapiens*]", May 7, 1993.
GenBank Public DNA Database Accession No. AAB23549.1 "Lysyl Oxidase [*Homo sapiens*]", May 8, 1993.
GenBank Public DNA Database Accession No. AAD02130.1 "Lysyl Oxidase [*Homo sapiens*]", May 6, 1999.
GenBank Public DNA Database Accession No. AAH15090.1 "Lysyl Oxidase-Like 1 [*Homo sapiens*]", Jul. 15, 2006.
GenBank Public DNA Database Accession No. AAH74820.1 "Lysyl Oxidase [*Homo sapiens*]", Jul. 15, 2006.
GenBank Public DNA Database Accession No. AAH74872.1 "Lysyl Oxidase [*Homo sapiens*]", Jul. 15, 2006.
GenBank Public DNA Database Accession No. AAK51671.1 "Lysyl Oxidase-Like 3 Protein [*Homo sapiens*]", May 9, 2001.
GenBank Public DNA Database Accession No. AAK71934.1 "Lysyl Oxidase-Related Protein C [*Homo sapiens*]", Jul. 11, 2001.
GenBank Public DNA Database Accession No. AF039291 "*Homo sapiens* Lysyl Oxidase mRNA, Complete cds", May 6, 1999.
GenBank Public DNA Database Accession No. AF282619 "*Homo sapiens* Lysyl Oxidase-like 3 Protein mRNA, Complete cds", May 9, 2001.
GenBank Public DNA Database Accession No. AF338441 "*Homo sapiens* Lysyl Oxidase-Related Protein C (LOXC) mRNA, Complete cds", Jul. 11, 2001.
GenBank Public DNA Database Accession No. BC015090 "*Homo sapiens* Lysyl Oxidase-Like 1, mRNA (cDNA Clone MGC:16541 Image:4040510), Complete cds", Jul. 15, 2006.
GenBank Public DNA Database Accession No. BC018439 "Mus Musculus Lysyl Oxidase, mRNA (cDNA Clone MGC:11525 Image:2655752), Complete cds", Jul. 15, 2006.
GenBank Public DNA Database Accession No. BC074820 "*Homo sapiens* Lysyl Oxidase, mRNA (cDNA Clone MGC:104085 Image:30915536), complete cds", Jul. 15, 2006.
GenBank Public DNA Database Accession No. BC074872 "*Homo sapiens* Lysyl Oxidase, mRNA (cDNA Clone MGC:103851 Image:30915233), Complete cds", Jul. 15, 2006.
GenBank Public DNA Database Accession No. M84150 "Human Lysyl Oxidase Gene, Partial cds", Jan. 7, 1995.
GenBank Public DNA Database Accession No. M94054 "Human Lysyl Oxidase (LOX) mRNA, Complete cds", Jan. 7, 1995.
GenBank Public DNA Database Accession No. NM_002317 "*Homo sapiens* Lysyl Oxidase (LOX), Transcript Variant 1, mRNA", Mar. 13, 2011.
GenBank Public DNA Database Accession No. NM_033325 "Mus Musculus Lysyl Oxidase-Like 2 (Loxl2), mRNA", Mar. 10, 2011.
GenBank Public DNA Database Accession No. NP_002308 "Protein-Lysine 6-Oxidase Isoform 1 Preproprotein [*Homo sapiens*]", Mar. 13, 2011.
GenBank Public DNA Database Accession No. NP_002309 "Lysyl Oxidase 2 Precursor [*Homo sapiens*]", Mar. 27, 2011.
GenBank Public DNA Database Accession No. NP_005567 "Lysyl Oxidase Homolog 1 Preproprotein [*Homo sapiens*]", Mar. 27, 2011.
GenBank Public DNA Database Accession No. NP_034858 "Protein-Lysine 6-Oxidase Precursor [Mus Musculus]", Mar. 11, 2011.

(56) References Cited

OTHER PUBLICATIONS

GenBank Public DNA Database Accession No. NP_034859 "Lysyl Oxidase Homolog 1 Precursor [Mus Musculus]", Mar. 12, 2011.
GenBank Public DNA Database Accession No. NP_115587 "Lysyl Oxidase Homolog 4 Precursor [*Homo sapiens*]", Mar. 13, 2011.
GenBank Public DNA Database Accession No. NP_115882 "AP-1 Complex Subunit mu-1 Isoform 2 [*Homo sapiens*]", Mar. 13, 2011.
GenBank Public DNA Database Accession No. NP_201582 "Lysyl Oxidase Homolog 2 Precursor [Mus Musculus]", Mar. 10, 2011.
GenBank Public DNA Database Accession No. S45875 "Lysyl Oxidase [Human, Skin Fibroblasts, mRNA Partial, 1254 nt]", May 8, 1993.
GenBank Public DNA Database Accession No. S78694 "Lysyl Oxidase [Human, mRNA, 1780 nt]", May 7, 1993.
GenBank Public DNA Database Accession No. U89942 "Human Lysyl Oxidase-Related Protein (WS9-14) mRNA, Complete cds", Aug. 18, 2003.
Giampuzzi et al. (2000) "Lysyl Oxidase Activates the Transcription Activity of Human Collagene III Promoter. Possible Involvement of Ku Antigen" J. Biol. Chem. 275(46):36341-36349.
Giampuzzi et al. (2001) "Down-Regulation of Lysyloxidase-Induced Tumorigenic Transformation in NRK-49F Cells Characterized by Constitutive Activation of Ras Proto-Oncogene" J Biol. Chem. 276(31):29226-29232.
Go et al. (2003) "The rat aortic ring assay for in vitro study of angiogenesis" Methods Mol. Med. 85:59-64.
González-Iriate et al. (2003) "A modified chorioallantoic membrane assay allows for specific detection of endothelial apoptosis induced by antiangiogenic substances" Angiogenesis 6(3):251-254.
Görögh et al. (2007) "Selective Upregulation and Amplification of the Lysyl Oxidase Like-4 (LOXL4) Gene in Head and Neck Squamous cell Carcinoma" J. Pathol. 212(1):74-82.
Görögh et al. (2008) "Functional analysis of the 5' flanking domain of the LOXL4 gene in head and neck squamous cell carcinoma cells." Int J Oncol 33(5): 1091-8.
Grant et al. (2001) "Overview: Rational Integration of Agents Directed at Novel Therapeutic Targets into Combination Chemotherapeutic Regimens" Curr. Opin. Investig Drugs 2(11):1600-1605.
Greenbaum et al. (2003) "Comparing protein abundance and mRNA expression levels on a genomic scale", Genome Biology 40 (9):117.01-117.08.
Grigorescu (2006) "Noninvasive Biochemical Markers of Liver Fibrosis," J. Gastrointestin. Liver Dis. 15(2):149-159.
Gross, et al. (2001) "Idiopathic Pulmonary Fibrosis" N. Engl. J. Med. 345(7):517-525.
Guedez et al. (2003) "Quantitative assessment of angiogenic responses by the directed in vivo angiogenesis assay" Am. J. Pathol. 162(5):1431-1439.
Gulec et al. (2004) "A new in vitro assay for human tumor angiogenesis: three-dimensional human tumor angiogenesis assay" Ann. Surgical Oncology 11(1):99-104.
Gura (1997) "Systems for Identifying New Drugs Are Often Faulty" Science 278(5347):1041-1042.
Ham et al. (2008) "144. Inhibition of an Extracellular Matrix Protein Increases Survival in Orthotopic Nude Mouse Models" J. Surg. Res. 144(2):239-240.
Harris et al. (1974) "Connective Tissue Amine Oxidase. II. Purification and Partial Characterization of Lysyl Oxidase from Chick Aorta" Biochim. Biophys. Acta 341(2):332-344.
Harrison & Lazo (1987) "High Dose Continuous Infusion of Bleomycin in Mice: A New Model for Drug-Induced Pulmonary Fibrosis" J. Pharmacol. Exp. Ther. 243(3):1185-1194.
Hartwell (1998) "Angiogenesis in P- and E-selectin-deficient mice" Microcirculation 5(2-3):173-178.
Hayashi et al. (2004) "Comparative immunocytochemical localization of lysyl oxidase (LOX) and the lysyl oxidase-like (LOXL) proteins: changes in the expression of LOXL during development and growth of mouse tissues." J Mol Histol 35(8-9): 845-55.
Hein et al. (2001) "Lysyl oxidases: expression in the fetal membranes and placenta." Placenta 22(1): 49-57.

Herrington et al. (1992) "Principles and basic methodology of DNA/RNA detection by in situ hybridization," Chapter 4, pp. 69-102, Diagnostic Molecular Pathology vol. 1, Phenotyping and genotyping of intact cells, IRL Press, Oxford University Press.
Higgins et al. (2007) "Hypoxia promotes a fibrogenesis in vivo via HIF-I stimulation of epithelial-to-mesenchymal transition" Journal Clinical Investigation 117(12):3810-20.
Hockel et al. (2001) "Tumor Hypoxia: Definitions and Current Clinical, Biologic and Molecular Aspects" Journal of the National Cancer Institute. 93(4):266-276.
Hohenester et al. (1999) "Crystal Structure of a Scavenger Receptor Cysteine-Rich Domain Sheds Light on an Ancient Superfamily" Nat. Struct. Biol. 6(3):228-232.
Hollosi et al. (2009) "Lysyl oxidase-like 2 promotes migration in noninvasive breast cancer cells but not in normal breast epithelial cells." Int J Cancer 125(2):318-327.
Hornstra et al. (2003) "Lysyl Oxidase is Required for Vascular and Diaphragmatic Development in Mice" J. Biol. Chem. 278(16):14387-14393.
Huang et al. (2001) "Cloning and Characterization of a Human Lysyl Oxidase-Like 3 Gene (hLOXL3)" Matrix Biol. 20(2):153-157.
Ishak et al. (1995) "Histological Grading and Staging of Chronic Hepatitis," J. Hepatol. 22:696-699.
Ito et al. (2001) "Molecular Cloning and Biological Activity of a Novel Lysyl Oxidase-Related Gene Expressed in Cartilage" J. Biol. Chem. 276(26):24023-24029.
Jain (1994) "Barriers to Drug Delivery in Solid Tumors" Scientific American 271(1):58-65.
Jakobsson et al. (1994) "A Morphometric Method to Evaluate Angiogenesis Kinetics in the Rat Mesentry" Intl. J. Exp. Pathol. 75(3):214-219.
Jansen & Csiszar (2007). "Intracellular localization of the matrix enzyme lysyl oxidase in polarized epithelial cells." Matrix Biol 26(2): 136-9.
Jansen et al. (2006) "Lysyl oxidase regulates kidney epithelial cell phenotype" ASMB Meeting Abstract/Matrix Biology 25:S92.
Jourdan Le-Saux et al. (1994) "Lysyl Oxidase cDNA of Myofibroblast from Mouse Fibrotic Liver" Biochem. Biophys. Res. Comm. 199(2):587-592.
Jourdan Le-Saux et al. (1999) "The LOXL2 Gene Encodes a New Lysyl Oxidase-Like Protein and Is Expressed at High Levels in Reproductive Tissues" J. Biol. Chem. 274(18):12939-12944.
Jourdan Le-Saux et al. (2001) "Central Nervous System, Uterus, Heart, and Leukocyte Expression of the LOXL3 Gene, Encoding a Novel Lysyl Oxidase-Like Protein" Genomics 74(2):211-218.
Jourdan-Le Saux et al. (1998) "The human lysyl oxidase-related gene (LOXL2) maps between markers D8S280 and D8S278 on chromosome 8p21.2-p21.3." Genomics 51(2): 305-7.
Jourdan-Le Saux et al. (2000) "The mouse lysyl oxidase-like 2 gene (mLOXL2) maps to chromosome 14 and is highly expressed in skin, lung and thymus." Matrix Biol 19(2): 179-83.
Julien et al. (2008) "A reproducible and quantifiable model of choroidal neovascularization induced by VEGF A after subretinal adenoviral gene transfer in the rabbit" Molecular Vision 14: 1358-1372.
Jung et al. (2003) "Purification of enzymatically active human lysyl oxidase and lysyl oxidase-like protein from *Escherichia coli* inclusion bodies." Protein Expr Purif 31(2): 240-6.
Kagan & Li (2003) "Lysyl Oxidase: Properties, Specificity, and Biological Roles Inside and Outside of the Cell" J. Cell. Biochem 88(4):660-672.
Kagan (1994) "Lysyl Oxidase: Mechanism, Regulation and Relationship to Liver Fibrosis" Pathol. Res. Pract. 190(9-10):910-919.
Kagan et al. (1982) "Lysyl Oxidase: Preparation and Role in Elastin Biosynthesis" Meth. Enzymol. 82(A):637-649.
Kagan et al. (1995) "Expression of Lysyl Oxidase from cDNA Constructs in Mammalian Cells: The Propeptide Region Is Not Essential to the Folding and Secretion of the Functional Enzyme" J. Cell Biochem. 59(3):329-38.
Kagan et al. (1995) "Catalytic properties and structural components of lysyl oxidase." Novartis Foundation Symp. 192: 100-15; discussion 115-21.

(56) References Cited

OTHER PUBLICATIONS

Kagan H.M. (2000) "Intra-and Extracellular Enzymes of Collagen Biosynthesis as Biological and Chemical Targets in the Control of Fibrosis" Acta Tropica 77(I):147-152.
Kaiser et al. (2006) "Cancer. First pass at cancer genome reveals complex landscape" Science 313(5792):1370.
Kaku et al. (2007) "Post-translational modifications of collagen upon BMP-induced osteoblast differentiation." Biochem Biophys Res Commun 359(3): 463-8.
Kamath et al. (2001) "Signaling from Protease-Activated Receptor-1 Inhibits Migration and Invasion of Breast Cancer Cells" Cancer Res. 61(15):5933-5940.
Kaneda et al. (2004) "Lysyl Oxidase is a Tumor Suppressor Gene Inactivated by Methylation and Loss of Heterozygosity in Human Gastric Cancers" Cancer Res. 64(18):6410-6415.
Kang et al. (2009) "Prosaposin Inhibits Tumor Metastasis Via Paracrine and Endocrine Stimulation of Stromal p53 and Tsp-1" Proc. Natl. Acad. Sci. U.S.A. 106(29):12115-12120.
Kenyon et al. (1991) "Lysyl Oxidase and rrg Messenger RNA" Science 253:802.
Kenyon et al. (2003) "TGF-[beta]1 Causes Airway Fibrosis and Increased Collagen I and III mRNA in Mice" Thorax 58(9):772-777.
Khakoo et al. (1997) "Congenital Cutis Laxa and Lysyl Oxidase Deficiency" Clin. Genet. 51(2):109-14.
Kim et al. (1995) "A New Gene with Sequence and Structural Similarity to the Gene Encoding Human Lysyl Oxidase" J. Biol. Chem. 270(13):7176-7182.
Kim et al. (1999) "Coexpression of the Lysyl Oxidase-Like Gene (LOXL) and the Gene Encoding Type III Procollagen in Induced Liver Fibrosis" J. Cell Biochem. 72(2):181-188.
Kim et al. (2003) "Expression and Purification of Enzymatically Active Forms of the Human Lysyl Oxidase-Like Protein 4" J. Biol. Chem. 278(52):52071-52074.
Kim et al. (1997) "A highly polymorphic (CA) repeat sequence in the human lysyl oxidase-like gene." Clin Genet 51(2): 131-2.
Kirschmann et al. (2002) "A Molecular Role for Lysyl Oxidase in Breast Cancer Invasion" Cancer Res. Cancer Res. 62(15):4478-4483.
Kirschmann et al. (1999) "Differentially expressed genes associated with the metastatic phenotype in breast cancer" Breast Cancer Res Treat. 55(2):127-136.
Klutke et al. (2008) "Decreased endopelvic fascia elastin content in uterine prolapse." Acta Obstet Gynecol Scand 87(1): 111-5.
Knodell et al. (1981) "Formulation and Application of a Numerical Scoring System for Assessing Histological Activity in Asymptomatic Chronic Active Hepatitis," Hepatol. 1(5):431-435.
Kragh et al. (2003) "In vivo chamber angiogenesis assay: an optimized Matrigel plug assay for fast assessment of anti-angiogenic activity" Intl. J. Oncology 22(2):305-311.
Kragh et al. (2004) "A versatile in vivo chamber angiogenesis assay for measuring antiangiogenic activity in mice" Oncology Reports 11(2):303-307.
Krebs & Krawetz (1993) "Lysyl Oxidase Copper-Talon Complex: A Model" Biochim. Biophys. Acta 1202(1):7-12.
Kresse et al. (2008) "DNA copy number changes in high-grade malignant peripheral nerve sheath tumors by array CGH." Mol Cancer 7: 48.
Laczko et al. (2007) "Active lysyl oxidase (LOX) correlates with focal adhesion kinase (FAK)/paxillin activation and migration in invasive astrocytes." Neuropathol Appl Neurobiol 33(6): 631-43.
Lazarus et al. (1995) "Induction of Human Monocyte Motility by Lysyl Oxidase" Matrix Biol. 14(9):727-731.
Le et al. (2007) "Expression and Prognostic Significance of a Panel of Tissue Hypoxia Markers in Head-and-Neck Squamous Cell Carcinoma," Int. J. Radiation Oncology Biol. Phys. 69(1):157-175.
Lelievre et al. (2008) "VE-statin/egfl7 regulates vascular elastogenesis by interacting with lysyl oxidases." EMBO J 27(12): 1658-70.
Levene et al. (1985) "Possibilities for the Therapeutic Control of Fibrosis," Br. J. Dermatol. 112(3):363-371.

Li et al. (1997) "Localization and Activity of Lysyl Oxidase within Nuclei of Fibrogenic Cells" Proc. Natl. Acad. Sci. USA 94(24):12817-12822.
Li et al. (1999) "Liver Fibrogenesis and the Role of Hepatic Stellate Cells: New Insights and Prospects for Therapy," J. Gastroentero. Hepatol. 14:618-633.
Li, et al. (2007) "Tumor microenvironment: the role of the tumor stroma in cancer." J Cell Biochem 101(4): 805-15.
Lichtenberg et al. (1999) "The rat Subcutaneous Air Sac model: a quantitative assay of antiangiogenesis in induced vessels" Am. J. Pharmacol. Toxicology 84(1):34-40.
Lucero & Kagan (2006) "Lysyl oxidase: an oxidative enzyme and effector of cell function." Cell Mol Life Sci 63(19-20): 2304-16.
Lugassy et al. (2012) "The Enzymatic Activity of Lysyl Oxidas-like-2 (LOXL2) Is Not Required for LOXL2-induced Inhibition of Keratinocyte Differentiation", Journal of Biological Chemistry 287(5):3541-3549.
Luo et al. (1998) "Differential Inhibition of Fluid Accumulation and Tumor Growth in Two Mouse Ascites Tumors by an Antivascular Endothelial Growth Factor/Permeability Factor Neutralizing Antibody" Cancer Res. 58(12):2594-2600.
Luo et al. (1998) "Significant expression of vascular endothelial growth factor/vascular permeability factor in mouse ascites tumors" Cancer Res., 58(12):2652-2660.
Macartney-Coxson et al. (2008) "Metastatic susceptibility locus, an 8p hot-spot for tumour progression disrupted in colorectal liver metastases: 13 candidate genes examined at the DNA, mRNA and protein level." BMC Cancer 8: 187.
Madakamutil et al. (2008) "Immunodominance in the TCR Repertoire of βTCR Peptide-Specific CD4+ Treg Population that Controls Experimental Autoimmune Encephalomyelitis" J. Immunology 180:4577-4585.
Maier et al. (2009) "Correlation of mRNA and protein in complex biological samples", FEBS Letters 583 (24):3966-3973.
Mäki & Kivirikko (2001) "Cloning and Characterization of a Fourth Human Lysyl Oxidase Isoenzyme" Biochem. J. 355(Pt 2):381-387.
Mäki et al. (2001) "Cloning and characterization of a fifth human lysyl oxidase isoenzyme: the third member of the lysyl oxidase-related subfamily with four scavenger receptor cysteine-rich domains." Matrix Biol 20(7): 493-6.
Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. 54 Supplement 1: S55-S56.
Masson et al. (2002) "Mouse Aortic Ring Assay: A New Approach of the Molecular Genetics of Angiogenesis" Biol. Proc. Online 4:24-31.
Mattioli et al. (1995) "Mimicry of the Immunodominant Conformation-Dependent Antigenic Site of Hepatitis A Virus by Motifs Selected from Synthetic Peptide Libraries," Journal of Virology 69(9):5294-5299.
Mbeunkui et al. (2007) "Identification of differentially secreted biomarkers using LC-MS/MS in isogenic cell lines representing a progression of breast cancer" Journal Proteome Res. 6:2993-3002.
McKechnie et al. (2003) "Hr44 Secreted wtih exosomes: Loss from Ciliary epithelium in response to inflammation" IOVS 44(6): 2650-2656.
Mehal et al. (2011) "Expressway to the Core of Fibrosis," Nat. Med. 17(5):552-553.
Miller et al. (2004) "A novel technique for quantifying changes in vascular density, endothelial cell proliferation and protein expression in response to modulators of angiogenesis using the chick chorioallantoic membrane (CAM) assay" J. Translational Med. 2(1):4.
Mollenhauer, et al. (1987) "Distribution of Extracellular Matrix Proteins in Pancreatic Ductal Adenocarcinoma and Its Influence on Tumor Cell Proliferation in Vitro," Pancreas 2(1):14-24.
Molnar et al. (2003) "Structural and functional diversity of lysyl oxidase and the LOX-like proteins" Biochim Biophys Acta. 1647(1-2):220-224.
Molnar et al. (2005) "Drosophila lysyl oxidases Dmloxl-1 and Dmloxl-2 are differentially expressed and the active DmLOXL-1 influences gene expression and development." J Biol Chem 280(24): 22977-85.

(56) References Cited

OTHER PUBLICATIONS

Monticone et al. (2004) "Gene expression profile of human bone marrow stromal cells determined by restriction fragment differential display analysis." J Cell Biochem 92(4): 733-44.
Morbidelli et al. (2004) "The rabbit corneal pocket assay for the study of angiogenesis" Cancer Treatment Res. 117:147-151.
Muller et al. (2006) "Lung fibroblasts from patients with emphysema show markers of senescence in vitro." Respir Res 7: 32.
Murawaki et al. (1991) "Serum Lysyl Oxidase Activity in Chronic Liver Disease in Comparison with Serum Levels of Prolyl Hydroxylase and Laminin" Hepatology 14(6):1167-1173.
Nagaoka et al. (2008) "1,25(OH)2D3 regulates collagen quality in an osteoblastic cell culture system." Biochem Biophys Res Commun 377(2): 674-8.
Nakken et al. (2007) "Multiple inflammatory-, tissue remodelling- and fibrosis genes are differentially transcribed in the livers of Abcb4 (-/-) mice harbouring chronic cholangitis." Scand J Gastroenterol 42(10): 1245-55.
National Cancer Institute; Staging: Questions and answers, www.cancer.gov/cancertopics/factsheet/detection/staging, Nov. 6, 2009.
NCBI dbSNP record for LOXL2, available at http://www.ncbi.nlm.nih.gov/projects/SNP/snpöref.cqi?locusId=4017, retrieved Apr. 19, 2012.
Nehls et al. (1995) "A novel, microcarrier-based in vitro assay for rapid and reliable quantification of three-dimensional cell migration and angiogenesis" Microvascular Res. 50(3):311-322.
Nelson et al. (1988) "Effect of beta-Aminopropionitrile and Ascorbate on Fibroblast Migration" Proc. Soc. Exp. Biol. Med. 188(3):346-352.
Nguyen et al. (1994) "Quantitation of angiogenesis and antiangiogenesis in the chick embryo chorioallantoic membrane" Microvascular Res. 47(1):31-40.
Nicosia et al. (1990) "Growth of microvessels in serum-free matrix culture of rat aorta. A quantitative assay of angiogenesis in vitro" Laboratory Investig. 63(1):115-122.
Nissanov et al. (1995) "Automatic vessel segmentation and quantification of the rat aortic ring assay of angiogenesis" Laboratory Investig. 73(5):734-739.
Noblesse et al. (2004) "Lsyl oxidase-like and lysysl oxidase are present in the dermis and epidermis of a skin equivalent and in himan skin and are associate to elastic fibers" J. Investig. Dermatol., 122:621-630.
Norrby (1992) "On the quantitative rat mesenteric-window angiogenesis assay" EXS 61:282-286.
Norrby (2006) "In vivo models of angiogenesis" J. Cell. Mol. Med. 10(3):588-612.
Ogata et al. (1996) "Changes in alveolar capilary formation in growing rat lung by repeated injections of a lathyrogen" Growth, Development and Aging 60:153-160.
Okada et al. (1995) "A quantative in vivo method of analyzing human tumor-induced angiogenesis in mice using agarose microencapsulation and hemoglobin enzyme-linked immunosorbent assay" Japan. J. Cancer Res. 86(12):1182-1188.
Ooshima & Midorikawa (1977) "Increased lysyl Oxidase Activity in Blood Vessels of Hypertensive Rats and Effect of beta-Aminopropionitrile on Arteriosclerosis" Jpn. Circ. J. 41(12):1337-40.
Orimo & Weinberg (2006) "Stromal fibroblasts in cancer: a novel tumor-promoting cell type." Cell Cycle 5(15): 1597-601.
Orimo et al. (2001) "Cancer-associated myofibroblasts possess various factors to promote endometrial tumor progression." Clin Cancer Res 7(10): 3097-105.
Palamakumbura et al. (2002) "A Fluorometric Assay for Detection of Lysyl Oxidase Enzyme Activity in Biological Samples" Anal. Biochem. 300(2):245-251.
Palamakumbura et al. (2004) "The Propeptide Domain of Lysyl Oxidase Induces Phenotypic Reversion of Ras-Transformed cells" J. Biol. Chem. 279(39):40593-40600.

Panchenko et al. (1996) "Metalloproteinase activity secreted by fibrogenic cells in the processing of prolysyl oxidase Potential Role of Procollagen C-Proteinase" J Biol Chem. 271(12):7113-7119.
Parsons-Wingerter et al. (2000) "Fibroblast growth factor-2 selectively stimulates angiogenesis of small vessels in arterial tree" Arteriosclerosis Thrombosis Vasc. Biol. 20(5):1250-1256.
Pascal et al. (2005) "Comparison of replicative senescence and stress-induced premature senescence combining differential display and low-density DNA arrays." FEBS Lett 579(17): 3651-9.
Paul (1993) Fundamental Immunology, 3rd Ed., Raven Press: NY:292-295.
Payne et al. (2005) "Lysyl oxidase regulates breast cancer cell migration and adhesion through a hydrogen peroxide-mediated mechanism" Cancer Res. 65(24):11429-11436.
Payne et al. (2007) "Paradoxical roles for lysyl oxidases in cancer—a prospect." J Cell Biochem 101(6): 1338-54.
Peinado et al. (2005) "A Molecular Role for Lysyl Oxidase-Like 2 Enzyme in Snail Regulation and Tumor Progression" EMBO J. 24(19):3446-3458.
Peinado et al. (2005) "Switching on-off Snail: LOXL2 versus GSK3β." Cell Cycle 4(12): 1749-52.
Peinado et al. (2008) "Lysyl Oxidase-Like 2 as a New Poor Prognosis Marker of Squamous Cell Carcinomas" Cancer Research 68(12):4541-4550.
Peroutka et al. (2008) "Enhanced Protein Expression in Mammalian Cells Using Engineered SUMO Fusions: Secreted Phospholipase A2" Protein Sci. 17(9):1586-1595.
Peyrol et al. (1997) "Lysyl oxidase gene expression in the stromal reaction to in situ and invasive ductal breast carcinoma" Am J. Pathol. 150(2):497-507.
Pinnell (1982) "Molecular Defects in the Ehlers-Danlos Syndrome" J. Invest. Dermatol. 79(Supp 1):90S-92S.
Pires Martins, et al. (2001) "Whole-body gene expression by data mining." Genomics 72(1): 34-42.
Polgar et al. (2007) "Lysyl oxidase interacts with hormone placental lactogen and synergistically promotes breast epithelial cell proliferation and migration." J Biol Chem 282(5):3262-72.
Postlethwaite et al. (1987) "Stimulation of the chemotactic migration of human fibroblasts by transforming growth factor β" J. Exp. Med. 165(1):251-256.
Postovit et al. (2008). "Hypoxia/reoxygenation: a dynamic regulator of lysyl oxidase-facilitated breast cancer migration." J Cell Biochem 103(5): 1369-78.
Pouysségur et al. (2006) "Hypoxia Signalling in Cancer and Approaches to Enforce Tumour Regression" Nature 441(7092):437-443.
Presta et al. (1999) "Purine analogue 6-methylmercaptopurine riboside inhibits early and late phases of the angiogenesis process" Cancer Res. 59(10):2417-2424.
R&D Systems. Ordering Information: Catalog No. MAB2639. Anti-human lysyl oxidase homolog 2 monoclonal antibody. Apr. 18, 2005.
Radisky et al. (2001) "Tumors Are Unique Organs Defined by Abnormal Signaling and Context" Semin. Cancer Bio. 11(2):87-95.
Rakic et al. (2003) "Placental Growth Factor, a Member of the VEGF Family, Contributes to the Development of Choroidal Neovascularization" Invest. Ophthalmol. Vis. Sci. 44(7):3186-3193.
Rayton et al. (1979) "Induction of Lysyl Oxidase with Copper. Properties of an In Vitro System" J. Biol. Chem. 254(3):621-626.
Reed et al. (2007) "Culture of murine aortic explants in 3-dimensional extracellular matrix: a novel, miniaturized assay of angiogenesis in vitro" Microvascular Res. 73(3):248-252.
Ren et al. (1998) "Reduced lysyl oxidase messenger RNA levels in experimental and human prostate cancer" Cancer Res. 58:1285-1290.
Resnick et al. (1994) "The SRCR Superfamily: A Family Reminiscent of the Ig Superfamily" Trends Biochem. Sci. 19(1):5-8.
Ribatti (2004) "The first evidence of the tumor-induced angiogenesis in vivo by using the chorioallantoic membrane assay dated 1913" Leukemia 18(8):1350-1351.
Ribatti et al. (1996) "The chick embryo chorioallantoic membrane as a model for in vivo research on angiogenesis" Intl. J. Devel. Biol. 40(6):1189-1197.

(56) References Cited

OTHER PUBLICATIONS

Ribatti et al. (1997) "New model for the study of angiogenesis and antiangiogenesis in the chick embryo chorioallantoic membrane: the gelatin sponge/chorioallantoic membrane assay" J. Vascular Res. 34(6):455-463.

Ribatti et al. (2000) "The Chick Embryo Chorioallantoic Membrane as a Model for In Vivo Research on Anti-Angiogenesis" Curr. Pharmacol. Biotechnol. 1(1):73-82.

Richardson et al. (2003) "Observations on the use of the avian chorioallantoic membrane (CAM) model in investigations into angiogenesis" Curr. Drug Targets Cardiovasc. Hematol. Disorders 3(2):155-185.

Riechmann, et al. (1988) "Reshaping Human Antibodies for Therapy" Nature 332(6162):323-327.

Rodriguez et al. (2010) "Modulation of lysyl oxidase-like 2 enzymatic activity by an allosteric antibody inhibitor" J. Biol. Chem. 285:20964-20974.

Rodriguez et al. (2008) Regulation of lysyl oxidase in vascular cells: lysyl oxidase as a new player in cardiovascular diseases. Cardiovasc Res. 79(I):7-13.

Roskoski (2007) "Vascular endothelial growth factor (VEGF) signaling in tumor progression" Critical Reviews in Oncology/Hematology 62: 179-213.

Rost et al. (2003) "Reduction of LOX- and LOXL2-mRNA expression in head and neck squamous cell carcinomas" Anticancer Res. 23(2B):1565-1573.

Royce et al. (1980) "Reduced Lysyl Oxidase Activity in Skin Fibroblasts from Patients with Menkes' Syndrome" Biochem. J. 192(2):579-86.

Rozalski et al. (1989) "Epitope Specificities of Murine Monoclonal and Rabbit Polyclonal Antibodies against Enterobacterial Lipopolysaccharides of the Re Chemotype" Infection and Immunity, 57(9):2645-2652.

Rucker et al. (1998) "Copper, Lysyl Oxidase, and Extracellular Matrix Protein Cross-Linking" Am. J. Clin. Nutr. 67(5 Suppl):996S-1002S.

Ruckert et al. (2009) "Functional analysis of LOXL2 in pancreatic carcinoma" International Journal of Colorectal Disease; Clinical and Molecular Gastroenterology and Surgery, Springer, Berlin, DE, 25(3):303-311.

Rudikoff et al. (1982) "Single Amino Acid Substitution Altering Antigen-Binding Specificity" PNAS USA 79(6):1979-1983.

Saito et al. (1997) "Regulation of a novel gene encoding a lysyl o5cidase-related protein in cellular adhesion and senescence" J. Biol Chem. 272(13):8157-8160.

Salnikow et al. (2008) "Regulation of hypoxia-inducible genes by ETS1 transcription factor." Carcinogenesis 29(8): 1493-9.

Sappino et al. (1988) "Smooth-Muscle Differentiation in Stromal Cells of Malignant and Non-Malignant Breast Tissues" Int. J. Cancer 41(5):707-712. Abstract Only.

Sasaki et al. (1998) "Mac-2 Binding Protein is a Cell-Adhesive Protein of the Extracellular Matrix Which Self-Assembles into Ring-Like Structures and Binds β1 Integrins, Collagens and Fibronectin" EMBO J. 17(6):1606-1613.

Satoh et al. (2003) "Inhibition of local adhesion kinase by antisense oligonucleotides enhances the sensitivity of breast cancer cells to camptothecins" Biocell 27(1):47-55.

Schena et al. (2005) "Pathogenic Mechanisms of Diabetic Nephropathy," J. Am. Soc. Nephrol. 16:S30-S33.

Scheuer (1991) "Classification of Chronic Viral Hepatitis: A Need for Reassessment," J. Hepatol. 13:372-374.

Schlotzer-Schrehardt et al. (2008) "Genotype-correlated expression of lysyl oxidase-like 1 in ocular tissues of patients with pseudoexfoliation syndrome/glaucoma and normal patients." Am J Pathol 173(6):1724-35.

Schmidt et al. (2007) "[Mapping of a deletion interval on 8p21-22 in prostate cancer by gene dosage PCR]." Verh Dtsch Ges Pathol 91: 302-7.

Sebban et al. (2009) "Lysyl oxidase-like 4 is alternatively spliced in an anatomic site-specific manner in tumors involving the serosal cavities." Virchows Arch 454(1): 71-9.

Selman et al. (2005) "Gene Expression Profiles Distinguish Idiopathic Pulmonary Fibrosis from Hypersensitivity Pneumonitis" Am. J. Respir. Crit.Care Med. 173(2):188-198.

Sevil et al. (1996) "Pharmacokinetic Analysis of Beta-Aminopropionitrile in Rabbits" Vet Res. 27(2):117-123 (Abstract only).

Sheppard (2006) "Transforming Growth Factor β: A Central Modulator of Pulmonary and Airway Inflammation and Fibrosis" Proc. Am. Thorac. Soc. 3(5):413-417.

Sheridan et al. (1979) "Increased Lysyl Oxidase Activity in Aortas of Hypertensive Rats and Effect of Beta-Aminopropionitrile" Exp Mol Pathol. 30(2):315-324.

Shieh et al. (2007) "Association of expression aberrances and genetic polymorphisms of lysyl oxidase with areca-associated oral tumorigenesis" Clinical Cancer Res. 13(15):4378-4385.

Siegel et al. (1978) "Biochemical and Immunochemical Study of Lysyl Oxidase in Experimental Hepatic Fibrosis in the Rat" Proc. Natl. Acad. Sci. USA 75(6):2945-2949.

Siegers et al. (1986) "Hepatoprotection by Malotilate against Carbon Tetrachloride-Alcohol Induced Liver Fibrosis" Inflammation Res. 18(5-6):600-603. Abstract Only.

Siemann et al. (2006) "Tumor Vasculature: a Target for Anticancer Therapies" in: "Vascular-Targeted Therapies in Oncology", John Wiley & Sons. Ltd. Chichester, UK.

Sion et al. (2006) "Lysyl oxidase (lox) and hypoxia-induced metastases" Cancer Biology & Therapy, 5(8):909-911.

Sivakumar et al. (2008) "Upregulation of Lysyl Oxidase and MMPs During Cardiac Remodeling in Human Dilated Cardiomyopathy" Mol Cell Biochem 307(1-2):159-167.

Smith-Mungo & Kagan (1998) "Lysyl Oxidase: Properties, Regulation and Multiple Functions in Biology" Matrix Biol. 16: 387-98.

Sommer et al. (1993) "Transient expression of lysyl oxidase by liver myofibroblasts in murine schistosomiasis" Laboratory Investigation 69(4):460-470.

Sørensen et al. (2007) "Hypoxia-induced Expression of Endogenous Markers in Vitro is Highly Influenced by pH" Radiotherapy and Oncology 83:362-366.

Stapleton et al. (1987) "Neutralization Escape Mutants Define a Dominant Immunogenic Neutralization Site on Hepatitis A Virus," Journal of Virology 61(2):491-498.

Stassar et al. (2001) "Identification of Human renal cell carcinoma associated genes by suppression subtractive hybridization" Br. J. Cancer 85(9):1372-1382.

Stassen (1976) "Properties of Highly Purified Lysyl Oxidase from Embryonic Chick Cartilage" Biophys. Acta 438(1):49-60.

Stiffey-Wilusz et al. (2001) "An ex vivo angiogenesis assay utilizing commercial porcine carotid artery: modification of the rat aortic ring assay" Angiogenesis 4(1):3-9.

Szabo et al. (1997) "The human lysyl oxidase-like gene maps between STS markers D15S215 and GHLC.GCT7C09 on chromosome 15." Hum Genet 101(2): 198-200.

Szauter et al. (2005) "Lysyl oxidase in development, aging and pathologies of the skin." Pathol Biol (Paris) 53(7): 448-56.

Tamura et al. (1998) "Inhibition of Cell Migration, Spreading, and Focal Adhesions by Tumor Suppressor PTEN" Science 280:1614-1618.

Tang et al. (1983) "Reaction of aortic lysyl oxidase with β-aminopropionitrile." J Biol Chem 258(7): 4331-8.

Tang, et al. (1984) "β-substituted ethylamine derivatives as suicide inhibitors of lysyl oxidase." J Biol Chem 259(2): 975-9.

Tannock. "Experimental Chemotherapy," Ch. 19, p. 338 and 352-359, in The Basic Science of Oncology, Tannock and Hill, eds., New York 1992.

Tarp et al. (2007) "Identification of a Novel Cancer-Specific Immunodominant Glycopeptide Epitope in the MUC1 Tandem Repeat," Glycobiology 17(2):197-209.

Terui, et al. (2006) "Blockade of bulky lymphoma-associated CD55 expression by RNA interference overcomes resistance to complement-dependent cytotoxicity with rituximab," Cancer Sci. 97:72-79.

(56) References Cited

OTHER PUBLICATIONS

Thiery et al. (2003) "Epithelial-Mesenchymal Transitions in Development and Pathologies" Curr. Opin. Cell. Biol. 15(6):740-6.

Thomassin et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.

Tockman et al. (1992) "Consideration in Bringing a Cancer Biomarker to Clinical Application" Cancer Res. 52:2711s-2718s.

Topp, et al. (1998) "Antibody Transport in Cultured Tumor Cell Layers" J. Control. Release 53(1-3):15-23.

Trackman & Kagan (1979) "Nonpeptidyl amine inhibitors are substrates of lysyl oxidase." J Biol Chem 254(16): 7831-6.

Trackman et al. (1981) "Development of a Peroxidase-Coupled Fluorometric Assay for Lysyl Oxidase" Anal. Biochem. 113(2):336-342.

Trackman et al. (1990) "Cloning of rat aorta lysyl oxidase cDNA: Complete codons and predicted amino acid sequence" Biochem. 29(20)4863-4870 (1990 and Corrected Page: Biochem. 30(33):8282.

Trentham et al. (1977) "Autoimmunity to Type II Collagen: An Experimental Model of Arthritis" J. Experimental Medicine 146:857-868.

Trivedy et al. (1999) "The Upregulation of Lysyl Oxidase in Oral Submucous Fibrosis and Squamou Cell Carcinoma" J. Oral Pathol. Med. 28(6):246-251.

Tzortzaki et al. (2006) "Active Remodeling in Idiopathic Interstitial Pneumonias: Evaluation of Collagen Types XII and XIV," J. Histochem. & Cytochem. 54(6):693-700.

Understanding Cancer Series: Cancer Slide 8: Invasion and Metastasis, www.cancer.gov/cancertopics/understandingcancer/cancer/slide8, posted Jan. 28, 2005, reviewed Sep. 30, 2009.

Vadasz et al. (2005) "Abnormal deposition of collagen around hepatocytes in Wilson's disease is associated with hepatocyte specific expression of lysyl oxidase and lysyl oxidase like protein-2." J Hepatol 43(3): 499-507.

Van Bergen et al. (2010) "The role of LOXa nd LOXL2 in wound healing after glaucoma filtration surgery", European Association for Vision and Eye Research, Oct. 8, 2010, Retrieved from the Internet: URL:http://www.ever.be/view_abstract.php?abs_id=5411.

Van Lancker et al. (1995) "Patterns of axillary lymph node metastasis in breast cancer" Am. J. Clin. Oncol. 18(3):267-272.

Van Roy et al. (1986) "Invasiveness and Metastatic Capability of Rat Fibroblast-like Cells before and after Transfection with Immortalizing and Transforming Genes" Cancer Res. 46:4787-4795.

Vautherot et al. (1992) "Bovine Coronavirus Spike Glycoprotein: Localization of an Immunodominant Region at the Amino-Terminal End of S2" Journal of General Virology 73:3289-3294.

Waldmann (2003) "Immunotherapy: Past, Present and Future" Nat. Med. 9(3):269-277.

Walling et al. (2004) "Agiessive basal cell carcinoma: Presentation, pathogenesis, and management" Cancer and Metastasis Reviews 23:389-402.

Walters & Kleeberger (2008) "Mouse Models of Bleomycin-Induced Pulmonary Fibrosis" Current Protocols Pharmacol. 40:5.46.1-5.46.17.

Wang et al. (2007) "Lysyl Oxidase Inhibition Reduces Rat Liver Fibrosis after Bile Duct Ligation" Gastroenterology & Digestive Disease Week Meeting—108th Annual Meeting of the American-Gastroenterological-Association. Washington, DC. May 19-24, 2007; 132(4):A827.

Watanabe et al. (2010) "Nucleolin as cell surface receptor for tumor necrosis factor-alpha inducing protein: a carcinogenic factor of Helicobacter pylori", Journal of Cancer Research and Clinical Oncology 136(6):911-921.

Watters et al. (1987) "Idiopathic Pulmonary Fibrosis. Pretreatment Bronchoalveolar Lavage Cellular Constituents and Their Relationships with Lung Histopathology and Clinical Response to Therapy" Am. Rev. Respir. Dis. 135(3):696-704. Abstract Only.

Weiner (1999) "An Overview of Monoclonal Antibody Therapy of Cancer" Seminars Oncology 26(4):41-50.

Weise et al. (2008) "LOXL4 is a selectively expressed candidate diagnostic antigen in head and neck cancer." Eur J Cancer 44(9): 1323-31.

Whaley-Connell et al. (2006) "Chronic Kidney Disease and the Cardiometabolic Syndrome," J. Clin. Hypert. 8(8):546-548.

Wu et al. (2007) "LOXL1 and LOXL4 are Epigenetically Silenced and Can Inhibit Ras/Extracellular Signal-Regulated Kinase Signaling Pathway in Human Bladder Cancer" Cancer Res. 67(9):4123-4129.

Zhang et al. (2007) "Hypoxia Enhances Metastatic Efficiency in HT-1060 Fibrosarcoma Cells by Increasing Cell Survival in Lungs Not Cell Adhesion and Invasion" Cancer Res. 67(18):7789-7797.

Zhu et al. (2002) "The thin prep rat aortic ring assay: a modified method for the characterization of angiogenesis in whole mounts" Angiogenesis 5(1-2):81-86.

Examination Report for NZ 598456, mailed Nov. 6, 2012.

Supplementary European Search Report for EP 10810673.3, mailed Nov. 26, 2012.

Supplementary European Search Report for EP 10810675.8, mailed Dec. 4, 2012.

Patent Examination Report No. 1 for AU 2008299784, mailed Dec. 12, 2012.

Non-Final Office Action for U.S. Appl. No. 12/860,834, mailed Jan. 10, 2013.

Office Action for U.S. Appl. No. 12/185,054, mailed Jan. 28, 2013.

Office Action for U.S. Appl. No. 13/204,336, mailed Nov. 26, 2012.

Office Action for U.S. Appl. No. 13/204,336, mailed Jan. 7, 2013.

Portolano, et al. (1993). "Lack of Promiscuity in Autoantigen-Specific H and L Chain Combinations as Revealed by Human H and L Chain 'Roulette'". J Immunol 150(3):880-887.

Notice of the Second Office Action for CN 200880110519.8, mailed Dec. 31, 2012.

Office Action for U.S. Appl. No. 13/021,555, mailed Feb. 15, 2013.

Office Action for U.S. Appl. No. 12/652,687, mailed Feb. 28, 2013.

Advisory Action issued by the United States Patent and Trademark Office for U.S. Appl. No. 13/412,544, mailed Sep. 15, 2014, 14 pages.

Behlke et al., "Designing Antisense Oligonucleotides," Integrated DNA Technologies, 17 pages (2005).

Communication Pursuant to Article 94(3) EPC issued by the European Patent Office for European Application No. 12172222.7, dated Jun. 26, 2014, 8 pages.

Communication pursuant to Article 94(3) EPC mailed Sep. 8, 2014, issued by the European Patent Office for European Application No. EP 08020752.5, 7 pages.

Communication Pursuant to Article 94(3) EPC issued by the European Patent Office for European Application No. 12172214.4, dated Jun. 27, 2014, 6 pages.

Communication Pursuant to Article 94(3) EPC mailed Jan. 20, 2014, issued by the European Patent Office for European Application No. EP 10810702.0, 6 pages.

Communication Pursuant to Rule 71(3) EPC for European Application No. 08830207.0, dated Jul. 22, 2014—Intent to Grant, 9 pages.

Decision on Rejection (translation) for Chinese Application No. 200880110519.8 mailed on Jul. 3, 2014, 14 pages.

Decision on Rejection (translation) for Chinese Application No. 201080047970.7, mailed on Aug. 1, 2014, 16 pages.

Decision to grant for EP 08795003.6, dated Dec. 13, 2012, 2 pages.

Erler, et al. (2006) "Lysyl Oxidase is Essential for Hypoxia-Induced Metastasis" Pro. Amer. Assoc. Cancer Res. 47:570.

Extended European Search Report for European Application No. 11740450.9, dated Oct. 28, 2013, 10 pages.

Final Office Action dated Jun. 13, 2014, in U.S. Appl. No. 13/412,544, 22 pages.

Final Office Action issued by the United States Patent and Trademark Office for U.S. Appl. No. 13/487,109, Feb. 27, 2014, 21 pages.

First Examination Report in corresponding Australian Application No. 2010284036, dated Feb. 21, 2014, 3 pages.

International Search Report issued by the International Searching Authority for PCT/US2013/067591, mailed Mar. 1, 2013, 5 pages.

(56) References Cited

OTHER PUBLICATIONS

Jianping, et al., "Influence of Gualouxiebai Decoction on the levels of NE, DA and 5-HT in the Lung and on BALF Cell Count in the Rats with Pulmonary Fibrosis", Journal of Beijing University, 26(6):36-38, 2003 (English abstract).
Laskowski, R.A., et al., "Protein Clefts in Molecular Recognition and Function," Protein Science, Wiley, US 5(12):2438-2452 (1996).
Lauwereys, M., et al., "Potent Enzyme Inhibitors Derived from Dromedary Heavy-Chain Antibodies," EMBO Journal, Oxford University Press, Surrey, GB 17(13):3512-3520, XP002135352 (1998).
Mayeux, et al., "Biomarkers: Potential Uses and Limitations," NeuroRx, 1:182-188, 2004.
Millipore Application Guide, "Rapid Lateral Flow Test Strips Considerations for Product Development," 2008, 42 pages.
Notice of Acceptance issued by the Australian Patent Office for Application No. 2008282739, dated Dec. 4, 2013, 3 pages.
Notice of Acceptance issued by the Australian Patent Office for Application No. 2011212830, dated May 9, 2014, 2 pages.
Notice of Acceptance issued by the New Zealand Patent Office for Application No. 598464, mailed Jun. 30, 2014, 2 pages.
Notice of Acceptance issued by the New Zealand Patent Office for Application No. 601615, mailed Jul. 9 , 2014, 1 page.
Notice of Allowance issued by the United States Patent and Trademark Office for U.S. Appl. No. 12/185,054, mailed Nov. 4, 2013, 11 pages.
Notice of Allowance issued by the United States Patent and Trademark Office for U.S. Appl. No. 13/021,555, mailed Nov. 4, 2013, 14 pages.
Notice of Allowance issued by the United States Patent and Trademark Office for U.S. Appl. No. 13/707,495, mailed Sep. 19, 2013, 9 pages.
Notice of Grant issued by the China Patent Office for Application No. 201080047979.8 dated Jun. 5, 2014, 4 pages.
Notice of the Fourth Office Action issued by the China Patent Office for Application No. 200880110519.8, dated Feb. 8, 2014, 19 pages (translation).
Notice of the Third Office Action issued by the China Patent Office for Application No. 200880110519.8, dated Sep. 27, 2013, 18 pages (translation).
Notterman, et al., "Transcriptional gene expression profiles of colorectal adenoma, adenocarcinoma, and normal tissue examined by oligonucleotide arrays," Cancer Research, 61(7): 3124-3130, 2001.
Office Action issued by the New Zealand Patent Office for Application 626510, dated Jul. 9, 2014, 2 pages.
Office Action issued by the United States Patent and Trademark Office for U.S. Appl. No. 13/416,976, dated Dec. 27, 2013, 15 pages.
Office Action issued by the United States Patent and Trademark Office for U.S. Appl. No. 13/412,544, dated Feb. 14, 2014, 36 pages.
Office Action issued by the New Zealand Patent Office for Application No. 618682, dated Aug. 27, 2014, 2 pages.
Office Action issued by the New Zealand Patent Office for Application 625850, dated Jun. 25, 2014, 3 pages.
Office Action issued by the Australian Patent Office for 2011212830, dated Oct. 26, 2013, 2 pages.
Office Action issued by the Australian Patent Office for Appliation 2010284036, mailed on Feb. 21, 2014, 3 pages.
Office Action issued by the Canadian Patent Office for Application No. 2,693,208 mailed on Jun. 16, 2014, 3 pages.
Office Action issued by the Federal Institute for Intellectual Property for Russian Application 2012110585, mailed on Jun. 26, 2014, 3 pages (translation).
Office Action issued by the issued by the Federal Institute for Intellectual Property for Russian Application No. 2012137515, dated May 19, 2014, 11 pages (translation).
Office Action issued by the United States Patent and Trademark Office for U.S. Appl. No. 12/652,687, mailed Apr. 14, 2014, 10 pages.
Office Action issued by the United States Patent and Trademark Office for U.S. Appl. No. 13/619,139, mailed Nov. 6, 2013, 27 pages.
Office Action issued by the United States Patent and Trademark Office for U.S. Appl. No. 13/487,109, mailed on Sep. 16, 2014, 29 pages.
Office Action issued by the China Patent Office for Application No. 201080047979.8 dated Feb. 20, 2014, 10 pages (translation).
Office Action issued by the European Patent Office for Application No. 10810673.3, dated May 12, 2014, 6 pages.
Office Action issued by the Singapore Patent Office for Application No. 201201216-7, mailed Feb. 27, 2014, 6 pages (translation).
Office Action issued by the Vietnamese Patent Office for Application No. 1-2013-03905, mailed Apr. 18, 2014, 2 pages (translation).
Office Action issued by the China Patent Office for Application No. 201180017532.0, mailed Mar. 25, 2014, 19 pages (translation).
Office Action issued by the Federal Institute for Intellectual Property for Russian Application No. 2012110578, mailed May 5, 2014, 5 pages (translation).
Office Action issued by the Federal Institute for Intellectual Property, in Russian Application No. 2012137515, mailed Nov. 22, 2013, 5 pages (translation).
Office Action issued by the Singapore Patent Office for Application No. 201205781-6, mailed Oct. 22, 2013, 6 pages (translation).
Otsuka, et al., "Differential expression of the L-plastin gene in human colorectal cancer progression and metastasis," Biochemical and Biophysical Research Communications, 289(4): 876-881 (2001).
Paul et al., (2002) "Effective Expression of Small Interfering RNA in Human Cells," Nature Biotechnology 20:505-508.
Popov et al., "Integrin alphavbeta6 is a marker of the progression of biliary and portal liver fibrosis and a novel target for antifibrotic therapies," Journal of Hepatology 48:453-464, 2008.
Popov et al., "Tissue transglutaminase does not affect fibrotic matrix stability or regression of liver fibrosis in mice," Gastroenterology 140:1642-1652, 2011.
Rosinberg A et al., Therapeutic angiogenesis for myocardial ischemia, Expert Rev Cardiovasc Ther., 2004, vol. 2, N.2, pp. 271-283.
S Van De Veire, The role of lox and LOXL2 in inflammation and fibrosis in a laser induced mouse model, 2009, vol. 87, Issue Supplement s244, p. 0, 2009 (found in the Internet at the http://onlinelibrary.wiley.eom/doi/10.1111/j.1755-3768.2009.4232.x/abstract, 2 pages.
Second Office Action issued by the China Patent Office for Applicaton 201080047970.7, mailed Apr. 10, 2014, 21 pages (translation).
Office Action dated May 20, 2015 for Chinese Patent Application No. CN20088010321.3.
Office Action dated Apr. 7, 2015 for U.S. Appl. No. 13/888,289.
Office Action dated Nov. 28, 2014 for Canadian Patent Application No. 2,693,310.
Office Action dated Apr. 9, 2015 for U.S. Appl. No. 13/888,293.

\* cited by examiner

```
                        SEQUENCE LISTING

<160> NUMBER OF SEQ ID NOS: 28

<210> SEQ ID NO 1
<211> LENGTH: 25
<212> TYPE: RNA
<213> ORGANISM: Artificial Sequence
<220> FEATURE:
<223> OTHER INFORMATION: Synthetic ribonucleotide

<400> SEQUENCE: 1
acagggauug aguccuggcu guuau                                           25

<210> SEQ ID NO 2
<211> LENGTH: 25
<212> TYPE: RNA
<213> ORGANISM: Artificial Sequence
<220> FEATURE:
<223> OTHER INFORMATION: Synthetic ribonucleotide

<400> SEQUENCE: 2
ucaacgaauu gucaaauuug aaccc                                           25

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ggggtttgtc cacagagctg                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
acgtgtcact ggagaagagc                                                 20

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
tggagcagca ccaagagcca gtct                                            24
```

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
cttgactggg gaagggtctg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
aaaacggggc tcaaatcacg                                              20

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
atcccaccct tggcattgct tggt                                         24

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
ccggctgctc agaagatac                                               19

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
ttcaggtaca ggctgtgata cat                                          23

<210> SEQ ID NO 11
<211> LENGTH: 26
<212> TYPE: DNA
<213> ORGANISM: Artificial Sequence
<220> FEATURE:
<223> OTHER INFORMATION: Synthetic primer

<400> SEQUENCE: 11
tggcgatcga tcttcttaga ttcacg                                       26

<210> SEQ ID NO 12
<211> LENGTH: 135
<212> TYPE: PRT
<213> ORGANISM: Artificial Sequence
<220> FEATURE:

```
<223> OTHER INFORMATION: synthetic construct
<220> FEATURE:
<221> NAME/KEY: CHAIN
<222> LOCATION: (1)...(135)
<223> OTHER INFORMATION: variable heavy chain region of monoclonal
      anti-LOXL2 antibody AB0023

<400> SEQUENCE: 12

Met Glu Trp Ser Arg Val Phe Ile Phe Leu Leu Ser Val Thr Ala Gly
  1               5                  10                  15

Val His Ser Gln Val Gln Leu Gln Gln Ser Gly Ala Glu Leu Val Arg
             20                  25                  30

Pro Gly Thr Ser Val Lys Val Ser Cys Lys Ala Ser Gly Tyr Ala Phe
         35                  40                  45

Thr Tyr Tyr Leu Ile Glu Trp Val Lys Gln Arg Pro Gly Gln Gly Leu
     50                  55                  60

Glu Trp Ile Gly Val Ile Asn Pro Gly Ser Gly Gly Thr Asn Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
        115                 120                 125

Thr Thr Leu Thr Val Ser Ser
        130                 135

<210> SEQ ID NO 13
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: variable light chain region of monoclonal
      anti-LOXL2 antibody AB0023

<400> SEQUENCE: 13

Met Arg Cys Leu Ala Glu Phe Leu Gly Leu Leu Val Leu Trp Ile Pro
  1               5                  10                  15

Gly Ala Ile Gly Asp Ile Val Met Thr Gln Ala Ala Pro Ser Val Ser
             20                  25                  30

Val Thr Pro Gly Glu Ser Val Ser Ile Ser Cys Arg Ser Ser Lys Ser
         35                  40                  45

Leu Leu His Ser Asn Gly Asn Thr Tyr Leu Tyr Trp Phe Leu Gln Arg
     50                  55                  60

Pro Gly Gln Ser Pro Gln Phe Leu Ile Tyr Arg Met Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
        130
```

```
<210> SEQ ID NO 14
<211> LENGTH: 116
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(116)
<223> OTHER INFORMATION: variable heavy chain region of monoclonal
      anti-LOXL2 antibody AB0023

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Tyr Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asn Trp Met Asn Phe Asp Tyr Trp Gly Gln Gly Thr Thr Val
            100                 105                 110

Thr Val Ser Ser
        115

<210> SEQ ID NO 15
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(112)
<223> OTHER INFORMATION: variable light chain region of monoclonal
      anti-LOXL2 antibody AB0023

<400> SEQUENCE: 15

Asp Ile Val Met Thr Gln Thr Pro Leu Ser Leu Ser Val Thr Pro Gly
 1               5                  10                  15

Gln Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Phe Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Val Glu Ile Lys
            100                 105                 110

<210> SEQ ID NO 16
<211> LENGTH: 10
<212> TYPE: PRT
<213> ORGANISM: Artificial Sequence
```

```
<220> FEATURE:
<223> OTHER INFORMATION: synthetic construct
<220> FEATURE:
<221> NAME/KEY: DOMAIN
<222> LOCATION: (1)...(10)
<223> OTHER INFORMATION: CDR1 of variable heavy chain region of
      monoclonal anti-LOXL2 antibody AB0023

<400> SEQUENCE: 16

Gly Tyr Ala Phe Thr Tyr Tyr Leu Ile Glu
1               5                   10

<210> SEQ ID NO 17
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(17)
<223> OTHER INFORMATION: CDR2 of variable heavy chain region of
      monoclonal anti-LOXL2 antibody AB0023

<400> SEQUENCE: 17

Val Ile Asn Pro Gly Ser Gly Gly Thr Asn Tyr Asn Glu Lys Phe Lys
1               5                   10                  15
Gly

<210> SEQ ID NO 18
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(7)
<223> OTHER INFORMATION: CDR3 of variable heavy chain region of
      monoclonal anti-LOXL2 antibody AB0023

<400> SEQUENCE: 18

Asn Trp Met Asn Phe Asp Tyr
1               5

<210> SEQ ID NO 19
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(16)
<223> OTHER INFORMATION: CDR1 of variable light chain region of
      monoclonal anti-LOXL2 antibody AB0023

<400> SEQUENCE: 19

Arg Ser Ser Lys Ser Leu Leu His Ser Asn Gly Asn Thr Tyr Leu Tyr
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(7)
```

```
<223> OTHER INFORMATION: CDR2 of variable light chain region of
      monoclonal anti-LOXL2 antibody AB0023

<400> SEQUENCE: 20

Arg Met Ser Asn Leu Ala Ser
 1               5

<210> SEQ ID NO 21
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(9)
<223> OTHER INFORMATION: CDR3 of variable light chain region of
      monoclonal anti-LOXL2 antibody AB0023

<400> SEQUENCE: 21

Met Gln His Leu Glu Tyr Pro Tyr Thr
 1               5

<210> SEQ ID NO 22
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(10)
<223> OTHER INFORMATION: CDR1 of variable heavy chain region of
      monoclonal anti-LOXL2 antibody AB0023

<400> SEQUENCE: 22

Gly Tyr Ala Phe Thr Tyr Tyr Leu Ile Glu
 1               5                  10

<210> SEQ ID NO 23
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(17)
<223> OTHER INFORMATION: CDR2 of variable heavy chain region of
      monoclonal anti-LOXL2 antibody AB0023

<400> SEQUENCE: 23

Val Ile Asn Pro Gly Ser Gly Gly Thr Asn Tyr Asn Glu Lys Phe Lys
 1               5                  10                  15

Gly

<210> SEQ ID NO 24
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(7)
<223> OTHER INFORMATION: CDR3 of variable heavy chain region of
      monoclonal anti-LOXL2 antibody AB0023

<400> SEQUENCE: 24
```

```
Asn Trp Met Asn Phe Asp Tyr
 1               5
```

<210> SEQ ID NO 25
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(16)
<223> OTHER INFORMATION: CDR1 of variable light chain region of
      monoclonal anti-LOXL2 antibody AB0023

<400> SEQUENCE: 25

```
Arg Ser Ser Lys Ser Leu Leu His Ser Asn Gly Asn Thr Tyr Leu Tyr
 1               5                  10                  15
```

<210> SEQ ID NO 26
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(7)
<223> OTHER INFORMATION: CDR2 of variable light chain region of
      monoclonal anti-LOXL2 antibody AB0023

<400> SEQUENCE: 26

```
Arg Met Ser Asn Leu Ala Ser
 1               5
```

<210> SEQ ID NO 27
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(9)
<223> OTHER INFORMATION: CDR3 of variable light chain region of
      monoclonal anti-LOXL2 antibody AB0023

<400> SEQUENCE: 27

```
Met Gln His Leu Glu Tyr Pro Tyr Thr
 1               5
```

<210> SEQ ID NO 28
<211> LENGTH: 219
<212> TYPE: PRT
<213> ORGANISM: Artificial Sequence
<220> FEATURE:
<223> OTHER INFORMATION: synthetically constructed epitope

<400> SEQUENCE: 28

```
Val Arg Leu Arg Gly Gly Ala Tyr Ile Gly Glu Gly Arg Val Glu Val
 1               5                  10                  15

Leu Lys Asn Gly Glu Trp Gly Thr Val Cys Asp Asp Lys Trp Asp Leu
                20                  25                  30

Val Ser Ala Ser Val Val Cys Arg Glu Leu Gly Phe Gly Ser Ala Lys
            35                  40                  45

Glu Ala Val Thr Gly Ser Arg Leu Gly Gln Gly Ile Gly Pro Ile His
        50                  55                  60
```

-continued

```
Leu Asn Glu Ile Gln Cys Thr Gly Asn Glu Lys Ser Ile Ile Asp Cys
 65              70                  75                  80

Lys Phe Asn Ala Glu Ser Gln Gly Cys Asn His Glu Glu Asp Ala Gly
                 85                  90                  95

Val Arg Cys Asn Thr Pro Ala Met Gly Leu Gln Lys Lys Leu Arg Leu
            100             105             110

Asn Gly Gly Arg Asn Pro Tyr Glu Gly Arg Val Glu Val Leu Val Glu
        115             120                 125

Arg Asn Gly Ser Leu Val Trp Gly Met Val Cys Gly Gln Asn Trp Gly
        130             135                 140

Ile Val Glu Ala Met Val Val Cys Arg Gln Leu Gly Leu Gly Phe Ala
145             150                 155                 160

Ser Asn Ala Phe Gln Glu Thr Trp Tyr Trp His Gly Asp Val Asn Ser
                165             170                 175

Asn Lys Val Val Met Ser Gly Val Lys Cys Ser Gly Thr Glu Leu Ser
            180             185                 190

Leu Ala His Cys Arg His Asp Gly Glu Asp Val Ala Cys Pro Gln Gly
        195             200                 205

Gly Val Gln Tyr Gly Ala Gly Val Ala Cys Ser
        210             215
```

CHEMOTHERAPEUTIC METHODS AND COMPOSITIONS

CROSS REFERENCE TO RELATED APPLICATIONS

This application is a divisional of U.S. patent application Ser. No. 12/652,687, filed Jan. 5, 2010, now pending, which claims the benefit of U.S. Provisional Patent Application No. 61/204,480, filed Jan. 6, 2009. The contents of each of these applications are incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 246102007010Seqlist.txt, date recorded: 25 Feb. 2013, size: 13,372 bytes).

INTRODUCTION

Chemotherapeutic and anti-neoplastic treatments often rely on the ability of a drug or macromolecule to kill dividing, or proliferating, cells but spare quiescent cells. Because malignant cells have lost normal control of cell division, these rapidly-proliferating cells are more sensitive to chemotherapeutics and anti-neoplastics than most other cells in the body. However, malignant cells often develop resistance to chemotherapeutic drugs and anti-neoplastic agents, perhaps due to their genetic instability. Accordingly, there is currently a need for methods and compositions that will prevent malignant cells from gaining resistance to chemotherapeutics and anti-neoplastics, and/or that can reverse such resistance if it develops.

The extracellular matrix, and its components, have so far not been investigated as a possible avenue for the development and improvement of anti-neoplastic and chemotherapeutic methods. To the contrary, the role of extracellular matrix proteins in the development of resistance to chemotherapeutics and anti-neoplastic agents remains poorly understood.

SUMMARY

The present disclosure provides methods and compositions for killing malignant cells, methods and compositions for enhancing the cell killing activity of an anti-neoplastic agent, and methods and compositions for reversing the resistance of a malignant cell to an anti-neoplastic agent. In these methods and compositions, a malignant cell that is resistant to an anti-neoplastic agent is grown, or is already growing, in the presence of an extracellular matrix (e.g., collagen), and the malignant cell is contacted with the anti-neoplastic agent and with an inhibitor of a lysyl oxidase-type enzyme. In certain embodiments, the malignant cell is contacted with a composition comprising an anti-neoplastic agent and an inhibitor of a lysyl oxidase-type enzyme. In other embodiments, the malignant cell is contacted separately with an anti-neoplastic agent and with an inhibitor of a lysyl oxidase-type enzyme. The lysyl oxidase-type enzyme can be any one of, or any combination of, lysyl oxidase (LOX), lysyl oxidase-like 1 (LOXL1), lysyl oxidase-like 2 (LOXL2), lysyl oxidase-like 3 (LOXL3) or lysyl oxidase-like 4 (LOXL4).

The methods can be performed in vitro (e.g., in culture) or in situ (e.g., in a patient). In situ treatment can be either local or systemic. For local treatments, the compositions are administered, e.g., to a tumor or to a region of the body in the vicinity of a tumor. Systemic treatments involve, e.g., infusion of the compositions into the circulatory system of a patient with a malignant disorder.

Inhibitors of lysyl oxidase-type enzymes can inhibit any stage of lysyl oxidase expression or activity including alteration of gene structure, transcription, RNA processing, translation and/or post-translational processing of a lysyl oxidase enzyme. Inhibitors of lysyl oxidase-type enzymes include, but are not limited to, small organic molecules (e.g., with a molecular weight less than 1 kD), as may be obtained by organic synthesis or combinatorial chemistry (i.e., "small molecules"); nucleic acids (e.g., siRNAs, shRNAs, antisense RNAs, triple helix-forming oligonucleotides) and proteins (e.g., antibodies).

Screening methods, for identifying molecules that enhance the cell killing activity of an anti-neoplastic agent, are also provided. These methods involve, inter alia, culturing malignant cells in the presence of an extracellular matrix (e.g., culturing the cells on a collagen substrate or on a collagen-containing matrix) and comparing cell viability in the presence of the anti-neoplastic agent with cell viability in the presence of the anti-neoplastic agent and a test molecule. If cell viability is lower in the presence of the test molecule, the test molecule enhances the killing activity of the anti-neoplastic agent. Molecules identified by the disclosed screening assays can be administered to a subject either together with, or separately from, the anti-neoplastic agent.

Exemplary test molecules for use in the disclosed screening assays include small organic molecules (e.g., with a molecular weight less than 1 kD), as may be obtained by organic synthesis or combinatorial chemistry (i.e., "small molecules"); nucleic acids (e.g., siRNAs, shRNAs, antisense RNAs, triple helix-forming oligonucleotides) and proteins (e.g., enzymes, antibodies).

Exemplary anti-neoplastic agents for use in the disclosed methods and compositions include, for example, antibodies and chemotherapeutic agents such as, for example, cisplatin, oxaliplatin, carboplatin, methotrexate, doxorubicin, docetaxel, erlotinib, TAXOL®, TAXOTERE®, paraclitaxel, 5-fluorouracil, and gemcitibine.

Also provided are compositions comprising malignant cells growing in the presence of an extracellular matrix (e.g., collagen), an anti-neoplastic agent, and an inhibitor of a lysyl oxidase-type enzyme. In certain embodiments, the malignant cells are resistant to the cell killing activity of the anti-neoplastic agent. In additional embodiments, said malignant cells are present in a tumor.

In additional embodiments, methods for testing the sensitivity of a malignant cell to a molecule are provided. In these embodiments, the malignant cell is grown in the presence of an extracellular matrix (e.g., on a collagen substrate or on a collagen-containing matrix) and is contacted with a candidate molecule. Lower cell survival in the presence of the candidate molecule than in its absence is indicative of sensitivity of the malignant cell to the candidate molecule. Exemplary candidate molecules include, but are not limited to, small organic molecules (e.g., with a molecular weight less than 1 kD), as may be obtained by organic synthesis or combinatorial chemistry (i.e., "small molecules"); nucleic acids (e.g., siRNAs, shRNAs, antisense RNAs, triple helix-forming oligonucleotides) and proteins (e.g., enzymes, antibodies).

Thus, the present disclosure encompasses, inter alia, the following embodiments:

1. A method for enhancing the cell killing activity of an anti-neoplastic agent, the method comprising contacting the cell with an anti-neoplastic agent and an inhibitor of a lysyl oxidase-type enzyme, wherein the cell is (i) growing in the presence of an extracellular matrix and (ii) is resistant to the anti-neoplastic agent.

2. The method of embodiment 1, wherein the cell is in culture.

3. The method of embodiment 1, wherein the cell is present in a tumor.

4. The method of embodiment 1, wherein the anti-neoplastic agent is a chemotherapeutic drug.

5. The method of embodiment 1, wherein the anti-neoplastic agent is a nucleic acid.

6. The method of embodiment 5, wherein the nucleic acid is a siRNA.

7. The method of embodiment 1, wherein the anti-neoplastic agent is a polypeptide.

8. The method of embodiment 7, wherein the polypeptide is an antibody.

9. The method of embodiment 1, wherein the extracellular matrix comprises a collagen.

10. The method of embodiment 9, wherein the collagen is type I collagen.

11. The method of embodiment 1, wherein the inhibitor of a lysyl oxidase-type enzyme is a low molecular weight (<1 kD) organic molecule.

12. The method of embodiment 1, wherein the inhibitor of a lysyl oxidase-type enzyme is a nucleic acid.

13. The method of embodiment 12, wherein the nucleic acid is a siRNA.

14. The method of embodiment 1, wherein the inhibitor of a lysyl oxidase-type enzyme is a polypeptide.

15. The method of embodiment 14, wherein the polypeptide is an antibody.

16. The method of embodiment 1, wherein the lysyl oxidase-type enzyme is LOXL2.

17. A method for killing a malignant cell, the method comprising contacting the malignant cell with an anti-neoplastic agent and an inhibitor of a lysyl oxidase-type enzyme, wherein the malignant cells is (i) growing in the presence of an extracellular matrix and (ii) is resistant to the anti-neoplastic agent.

18. The method of embodiment 17, wherein the malignant cell is in culture.

19. The method of embodiment 17, wherein the malignant cell is present in a tumor.

20. The method of embodiment 17, wherein the anti-neoplastic agent is a chemotherapeutic drug.

21. The method of embodiment 17, wherein the anti-neoplastic agent is a nucleic acid.

22. The method of embodiment 21, wherein the nucleic acid is a siRNA.

23. The method of embodiment 17, wherein the anti-neoplastic agent is a polypeptide.

24. The method of embodiment 23, wherein the polypeptide is an antibody.

25. The method of embodiment 17, wherein the extracellular matrix comprises a collagen.

26. The method of embodiment 25, wherein the collagen is type I collagen.

27. The method of embodiment 17, wherein the inhibitor of a lysyl oxidase-type enzyme is a low molecular weight (<1 kD) organic molecule.

28. The method of embodiment 17, wherein the inhibitor of a lysyl oxidase-type enzyme is a nucleic acid.

29. The method of embodiment 28, wherein the nucleic acid is a siRNA.

30. The method of embodiment 17, wherein the inhibitor of a lysyl oxidase-type enzyme is a polypeptide.

31. The method of embodiment 30, wherein the polypeptide is an antibody.

32. The method of embodiment 17, wherein the lysyl oxidase-type enzyme is LOXL2.

33. A method for reversing resistance of a malignant cell to an anti-neoplastic agent, the method comprising contacting the malignant cell with an anti-neoplastic agent and an inhibitor of a lysyl oxidase-type enzyme, wherein the malignant cells is (i) growing in the presence of an extracellular matrix and (ii) is resistant to the anti-neoplastic agent.

34. The method of embodiment 33, wherein the malignant cell is in culture.

35. The method of embodiment 33, wherein the malignant cell is present in a tumor.

36. The method of embodiment 33, wherein the anti-neoplastic agent is a chemotherapeutic drug.

37. The method of embodiment 33, wherein the anti-neoplastic agent is a nucleic acid.

38. The method of embodiment 37, wherein the nucleic acid is a siRNA.

39. The method of embodiment 33, wherein the anti-neoplastic agent is a polypeptide.

40. The method of embodiment 39, wherein the polypeptide is an antibody.

41. The method of embodiment 33, wherein the extracellular matrix comprises a collagen.

42. The method of embodiment 41, wherein the collagen is type I collagen.

43. The method of embodiment 33, wherein the inhibitor of a lysyl oxidase-type enzyme is a low molecular weight (<1 kD) organic molecule.

44. The method of embodiment 33, wherein the inhibitor of a lysyl oxidase-type enzyme is a nucleic acid.

45. The method of embodiment 44, wherein the nucleic acid is a siRNA.

46. The method of embodiment 33, wherein the inhibitor of a lysyl oxidase-type enzyme is a polypeptide.

47. The method of embodiment 46, wherein the polypeptide is an antibody.

48. The method of embodiment 33, wherein the lysyl oxidase-type enzyme is LOXL2.

49. A method for identifying a molecule that enhances the cell killing activity of an anti-neoplastic agent, the method comprising providing a cell culture comprising one or more cells, wherein the cells are (i) growing in the presence of an extracellular matrix, and (ii) resistant to the anti-neoplastic agent; contacting the cell culture with the anti-neoplastic agent; optionally contacting the cell culture with a test molecule; and measuring cell viability; wherein lower cell viability in the presence of the test molecule and the anti-neoplastic agent, compared to cell viability in the presence of the anti-neoplastic agent alone, indicates that the test molecule is a molecule that enhances the cell killing activity of the anti-neoplastic agent.

50. The method of embodiment 49, wherein the anti-neoplastic agent is a chemotherapeutic drug.

51. The method of embodiment 50, wherein the chemotherapeutic drug is selected from the group consisting of methotrexate, cisplatin, doxorubicin, docetaxel, erlotinib, TAXOL®, paraclitaxel, TAXOTERE®, 5-fluorouracil and gemcitibine.

52. The method of embodiment 49, wherein the anti-neoplastic agent is a nucleic acid.

53. The method of embodiment 52, wherein the nucleic acid is a siRNA.

54. The method of embodiment 49, wherein the anti-neoplastic agent is a polypeptide.

55. The method of embodiment 54, wherein the polypeptide is an antibody.

56. The method of embodiment 49, wherein the extracellular matrix comprises a collagen.

57. The method of embodiment 56, wherein the collagen is type I collagen.

58. The method of embodiment 49, wherein the test molecule is a low molecular weight (<1 kD) organic molecule.

59. The method of embodiment 49, wherein the test molecule is a nucleic acid.

60. The method of embodiment 59, wherein the nucleic acid is a siRNA.

61. The method of embodiment 49, wherein the test molecule is a polypeptide.

62. The method of embodiment 61, wherein the polypeptide is an antibody.

63. The method of embodiment 49, wherein the test molecule is an inhibitor of a lysyl oxidase-type enzyme.

64. The method of embodiment 63, wherein the lysyl oxidase-type enzyme is LOXL2.

65. The method of embodiment 49, further comprising administering the anti-neoplastic agent and the molecule that enhances the cell killing activity of the anti-neoplastic to a subject with a malignancy or neoplastic disorder.

66. A composition comprising (a) cells growing in the presence of an extracellular matrix, wherein the cells are resistant to an anti-neoplastic agent; (b) the anti-neoplastic agent; and (c) an inhibitor of a lysyl oxidase-type enzyme.

67. The composition of embodiment 66, wherein the cells are in culture.

68. The composition of embodiment 66, wherein the cells are present in a tumor.

69. The composition of embodiment 66, wherein the anti-neoplastic agent is a chemotherapeutic drug.

70. The composition of embodiment 69, wherein the chemotherapeutic drug is selected from the group consisting of methotrexate, cisplatin, doxorubicin, docetaxel, erlotinib, TAXOL®, paraclitaxel, TAXOTERE®, 5-fluorouracil and gemcitibine.

71. The composition of embodiment 66, wherein the anti-neoplastic agent is a nucleic acid.

72. The composition of embodiment 71, wherein the nucleic acid is a siRNA.

73. The composition of embodiment 66, wherein the anti-neoplastic agent is a polypeptide.

74. The composition of embodiment 73, wherein the polypeptide is an antibody.

75. The composition of embodiment 66, wherein the extracellular matrix comprises a collagen.

76. The composition of embodiment 75, wherein the collagen is type I collagen.

77. The composition of embodiment 66, wherein the inhibitor of a lysyl oxidase-type enzyme is a low molecular weight (<1 kD) organic molecule.

78. The composition of embodiment 66, wherein the inhibitor of a lysyl oxidase-type enzyme is a nucleic acid.

79. The composition of embodiment 78, wherein the nucleic acid is a siRNA.

80. The composition of embodiment 66, wherein the inhibitor of a lysyl oxidase-type enzyme is a polypeptide.

81. The composition of embodiment 80, wherein the polypeptide is an antibody.

82. The composition of embodiment 66, wherein the lysyl oxidase-type enzyme is LOXL2.

83. A method for assessing the sensitivity of a malignant cell to a test molecule, the method comprising growing the malignant cell in the presence of an extracellular matrix; optionally contacting the cell with the test molecule; and assaying for cell survival; wherein, if cell survival is lower in the presence of the test molecule than in its absence, the malignant cell is sensitive to the test molecule.

84. The method of embodiment 83, wherein the malignant cell is in culture.

85. The method of embodiment 83, wherein the malignant cell is present in a tumor.

86. The method of embodiment 83, wherein the extracellular matrix comprises a collagen.

87. The method of embodiment 86, wherein the collagen is type I collagen.

88. The method of embodiment 83, wherein the test molecule is a low molecular weight (<1 kD) organic molecule.

89. The method of embodiment 83, wherein the test molecule is a nucleic acid.

90. The method of embodiment 89, wherein the nucleic acid is a siRNA.

91. The method of embodiment 83, wherein the test molecule is a polypeptide.

92. The method of embodiment 91, wherein the polypeptide is an antibody.

93. The method of embodiment 83, wherein the test molecule is an inhibitor of a lysyl oxidase-type enzyme.

94. The method of embodiment 93, wherein the lysyl oxidase-type enzyme is LOXL2.

95. The method of embodiment 83, further comprising growing the malignant cell in the presence of an anti-neoplastic agent.

96. The method of embodiment 95, wherein the anti-neoplastic agent is a chemotherapeutic drug.

97. The method of embodiment 96, wherein the chemotherapeutic drug is selected from the group consisting of methotrexate, cisplatin, doxorubicin, docetaxel, erlotinib, TAXOL®, paraclitaxel, TAXOTERE®, 5-fluorouracil and gemcitibine.

98. The method of embodiment 95, wherein the anti-neoplastic agent is a nucleic acid.

99. The method of embodiment 98, wherein the nucleic acid is a siRNA.

100. The method of embodiment 95, wherein the anti-neoplastic agent is a polypeptide.

101. The method of embodiment 100, wherein the polypeptide is an antibody.

102. The method of embodiment 93, wherein the inhibitor of a lysyl oxidase-type enzyme is a low molecular weight (<1 kD) organic molecule.

103. The method of embodiment 93, wherein the inhibitor of a lysyl oxidase-type enzyme is a nucleic acid.

104. The method of embodiment 103, wherein the nucleic acid is a siRNA.

105. The method of embodiment 93, wherein the inhibitor of a lysyl oxidase-type enzyme is a polypeptide.

106. The method of embodiment 105, wherein the polypeptide is an antibody.

DETAILED DESCRIPTION

Figure 1:
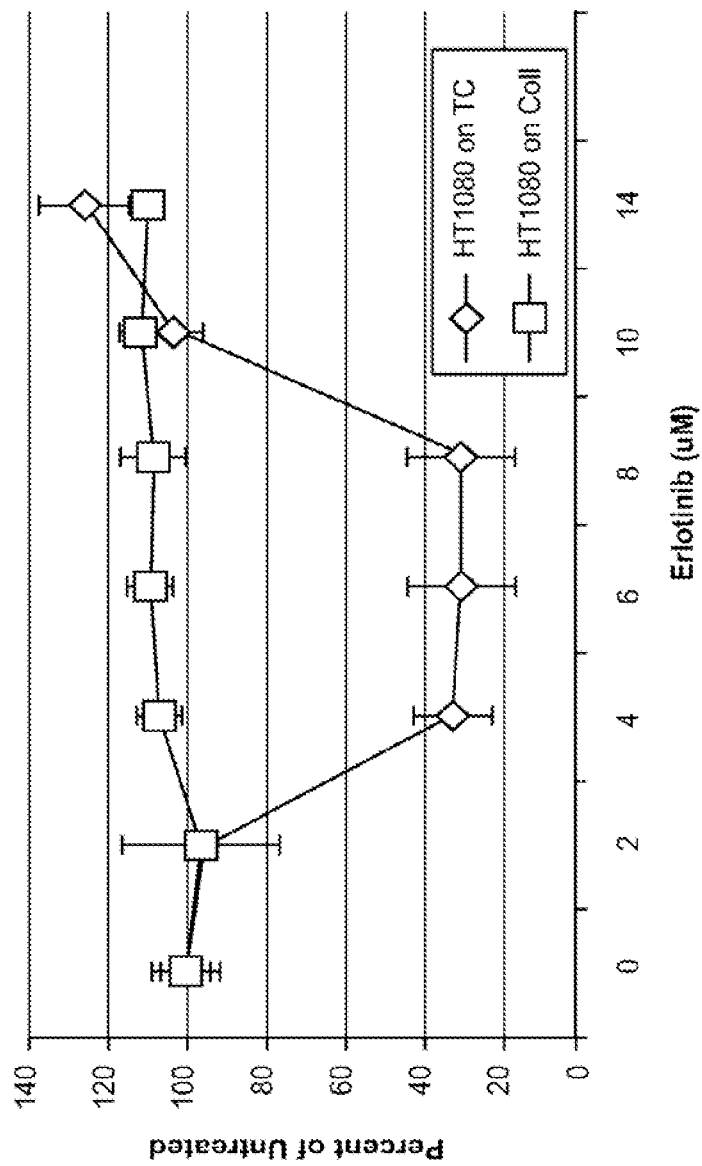
FIG. 1 shows the effect of increasing concentrations of erlotinib on the survival of HT1080 cells, expressed as percentage of viable cells compared to control cultures not exposed to the drug. Cells were cultured either in standard tissue culture plastic wells (diamonds) or in collagen-coated wells (squares).
Figure 2:
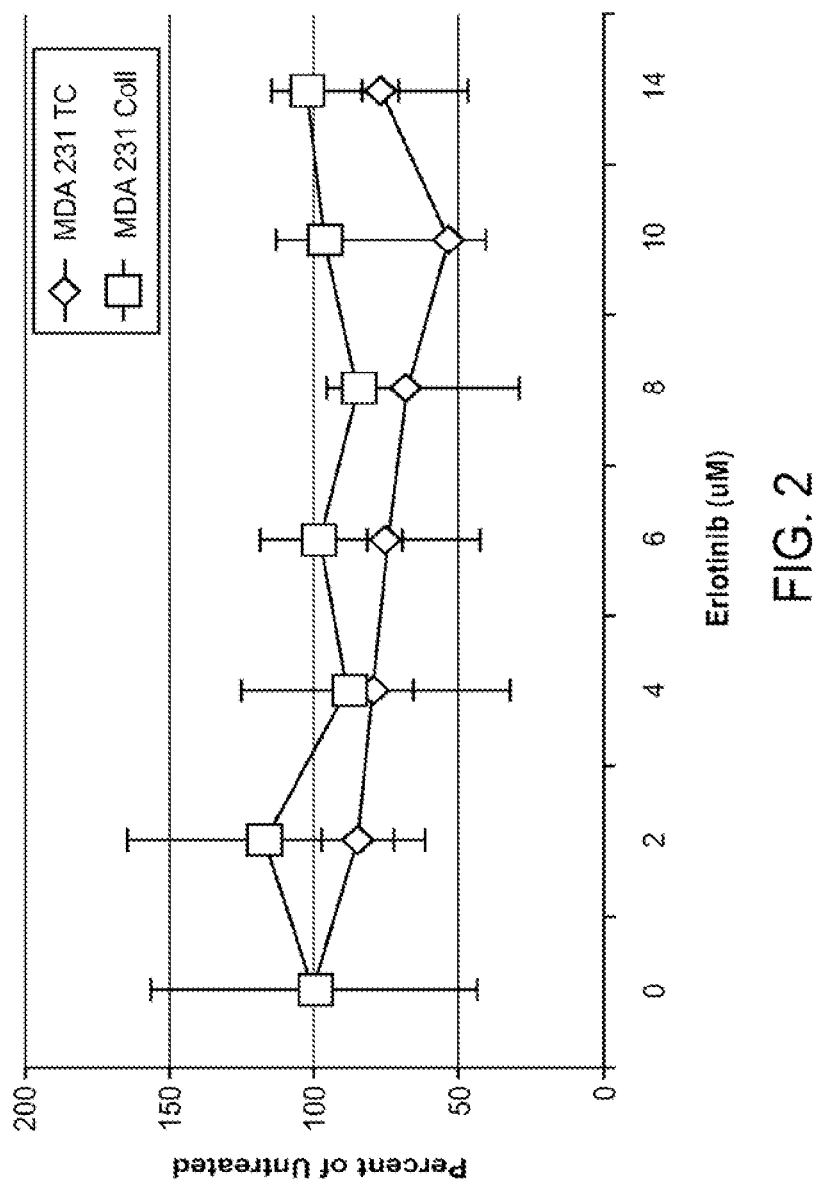
FIG. 2 shows the effect of increasing concentrations of erlotinib on the survival of MDA 231 cells. Cells were cultured either in standard tissue culture plastic wells (diamonds) or in collagen-coated wells (squares).
Figure 3:
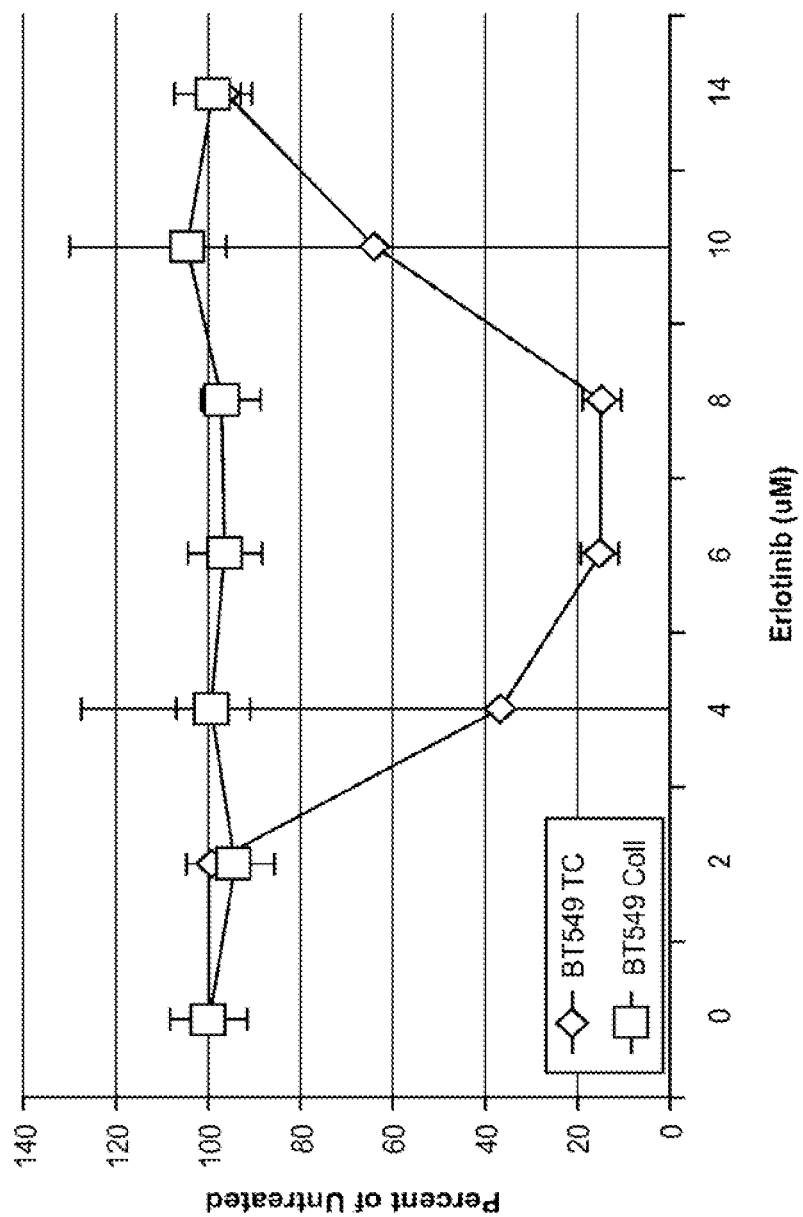
FIG. 3 shows the effect of increasing concentrations of erlotinib on the survival of BT549 cells. Cells were cultured either in standard tissue culture plastic wells (diamonds) or in collagen-coated wells (squares).
Figure 4:
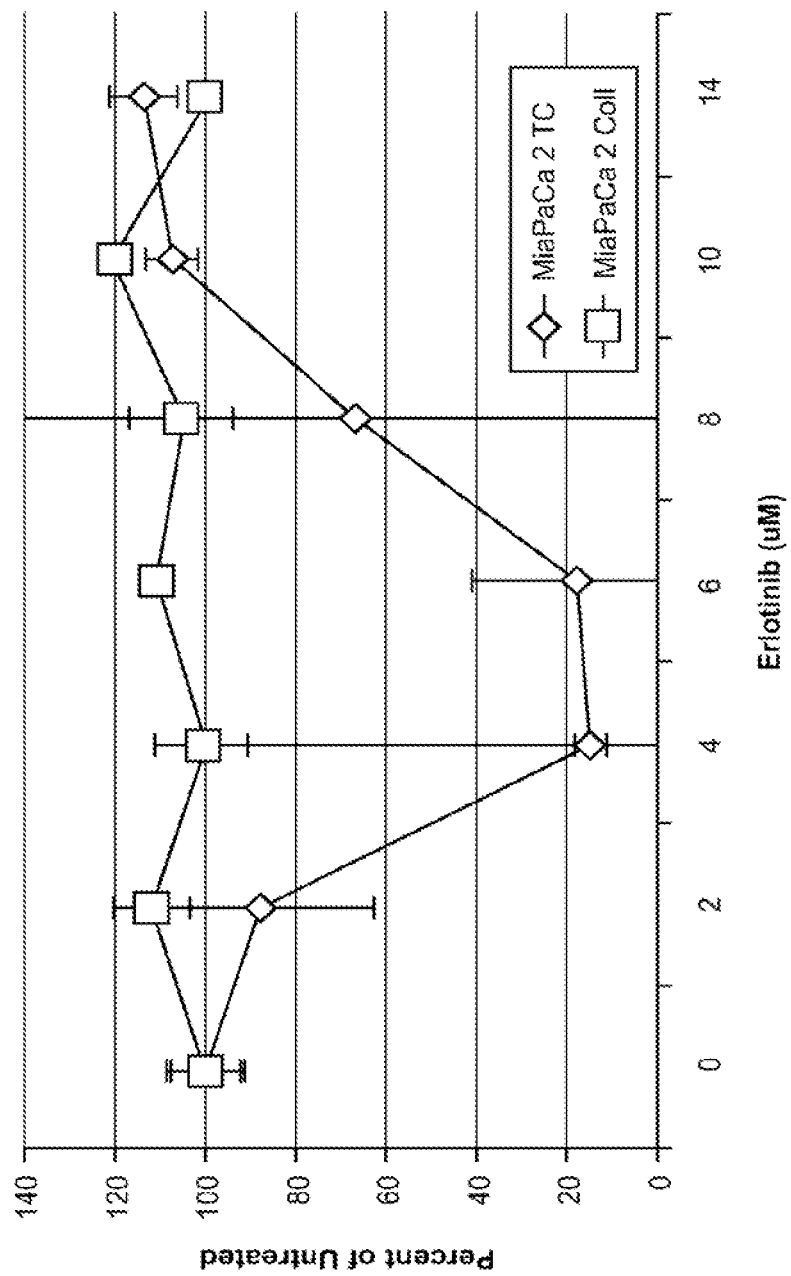
FIG. 4 shows the effect of increasing concentrations of erlotinib on the survival of MiaPaCa2 cells. Cells were cultured either in standard tissue culture plastic wells (diamonds) or in collagen-coated wells (squares).
Figure 5:
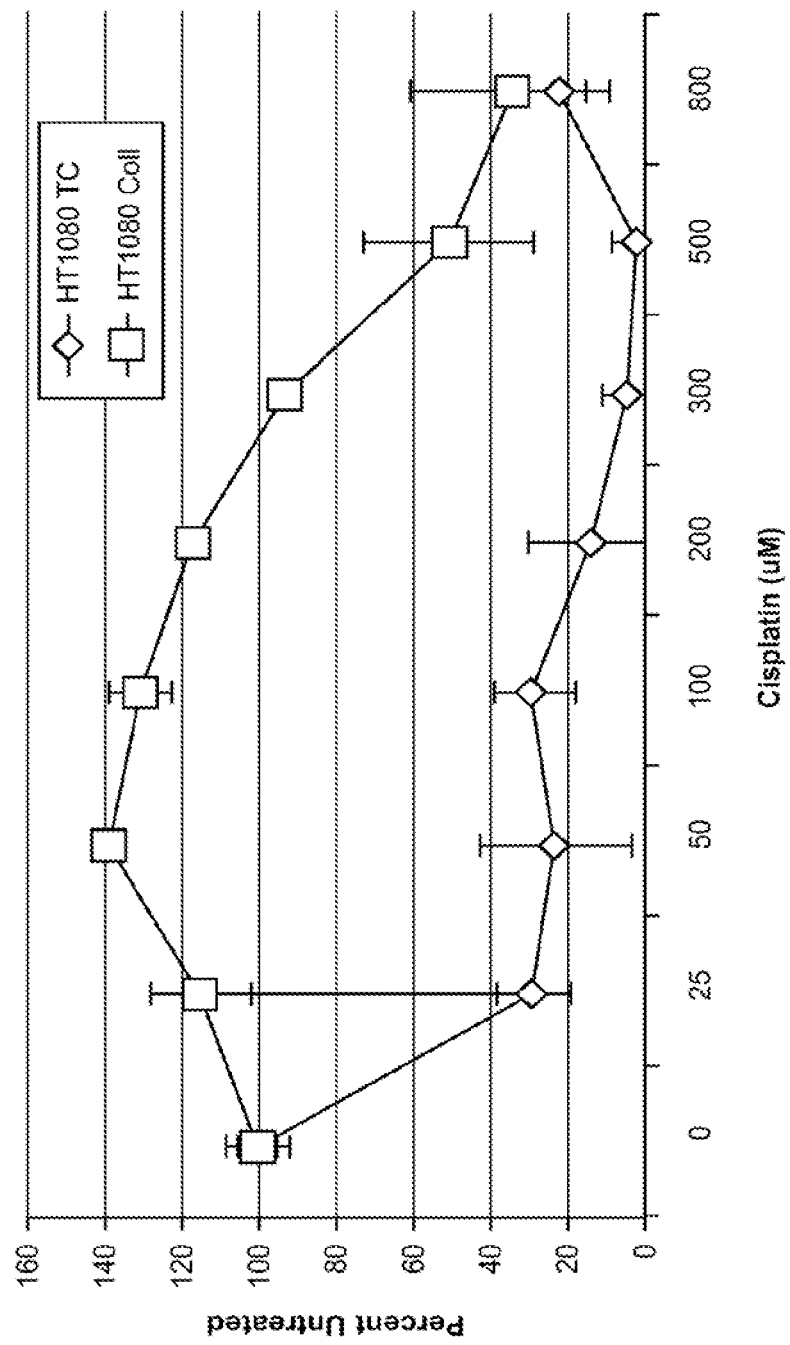
FIG. 5 shows the effect of increasing concentrations of cisplatin on the survival of HT1080 cells. Cells were cultured either in standard tissue culture plastic wells (diamonds) or in collagen-coated wells (squares).
Figure 6:
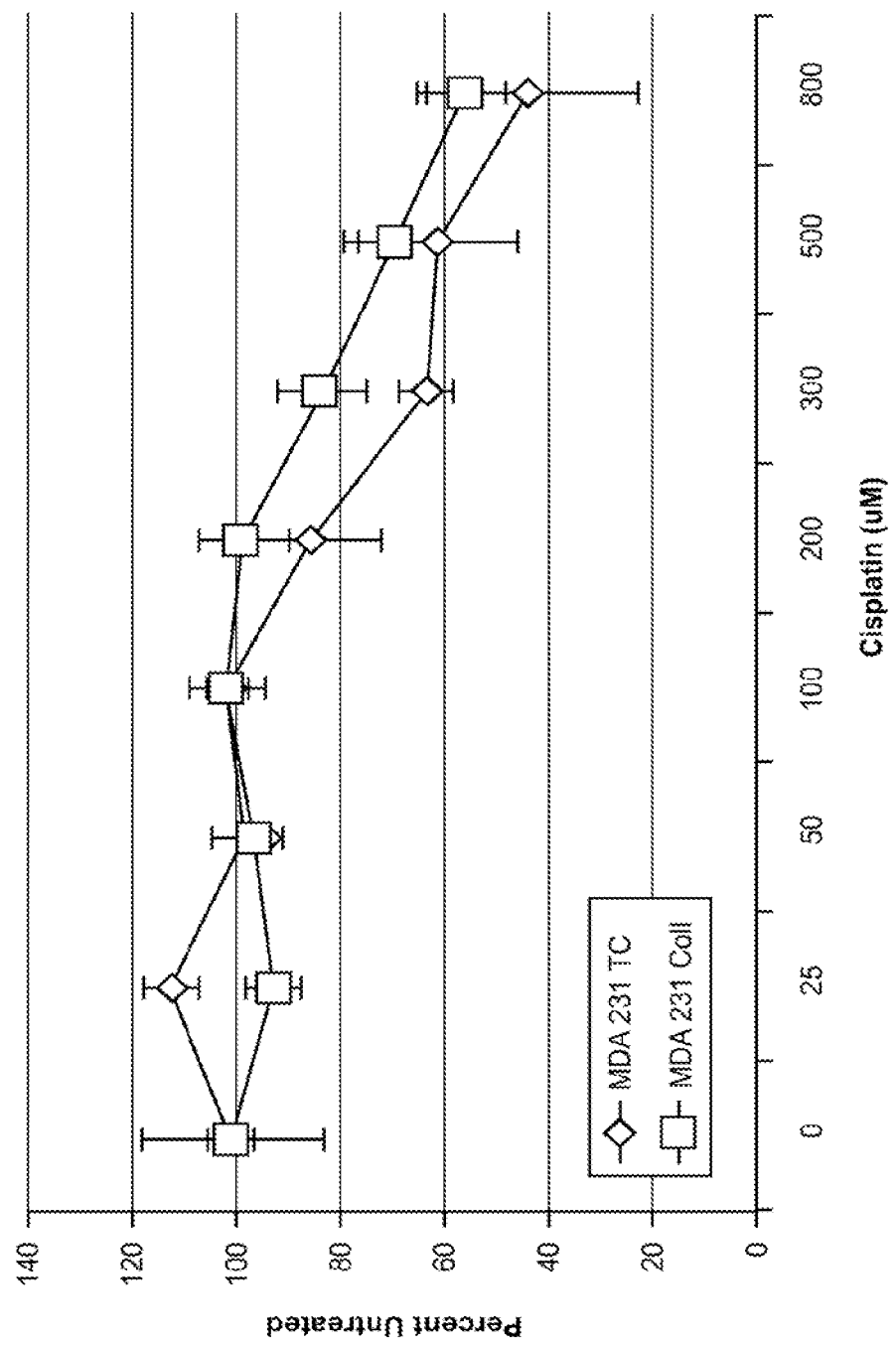
FIG. 6 shows the effect of increasing concentrations of cisplatin on the survival of MDA 231 cells. Cells were cultured either in standard tissue culture plastic wells (diamonds) or in collagen-coated wells (squares).
Figure 7:
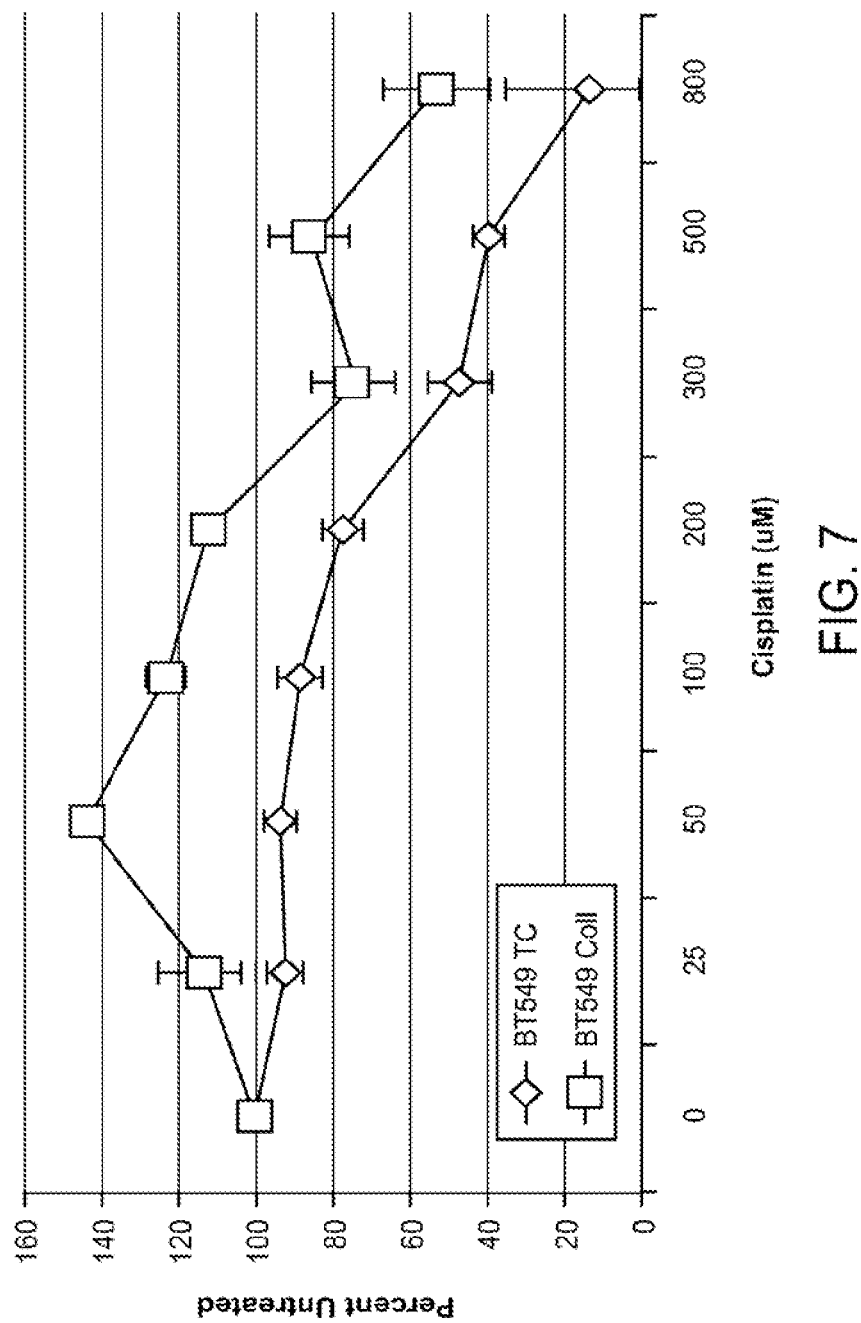
FIG. 7 shows the effect of increasing concentrations of cisplatin on the survival of BT549 cells. Cells were cultured either in standard tissue culture plastic wells (diamonds) or in collagen-coated wells (squares).
Figure 8:
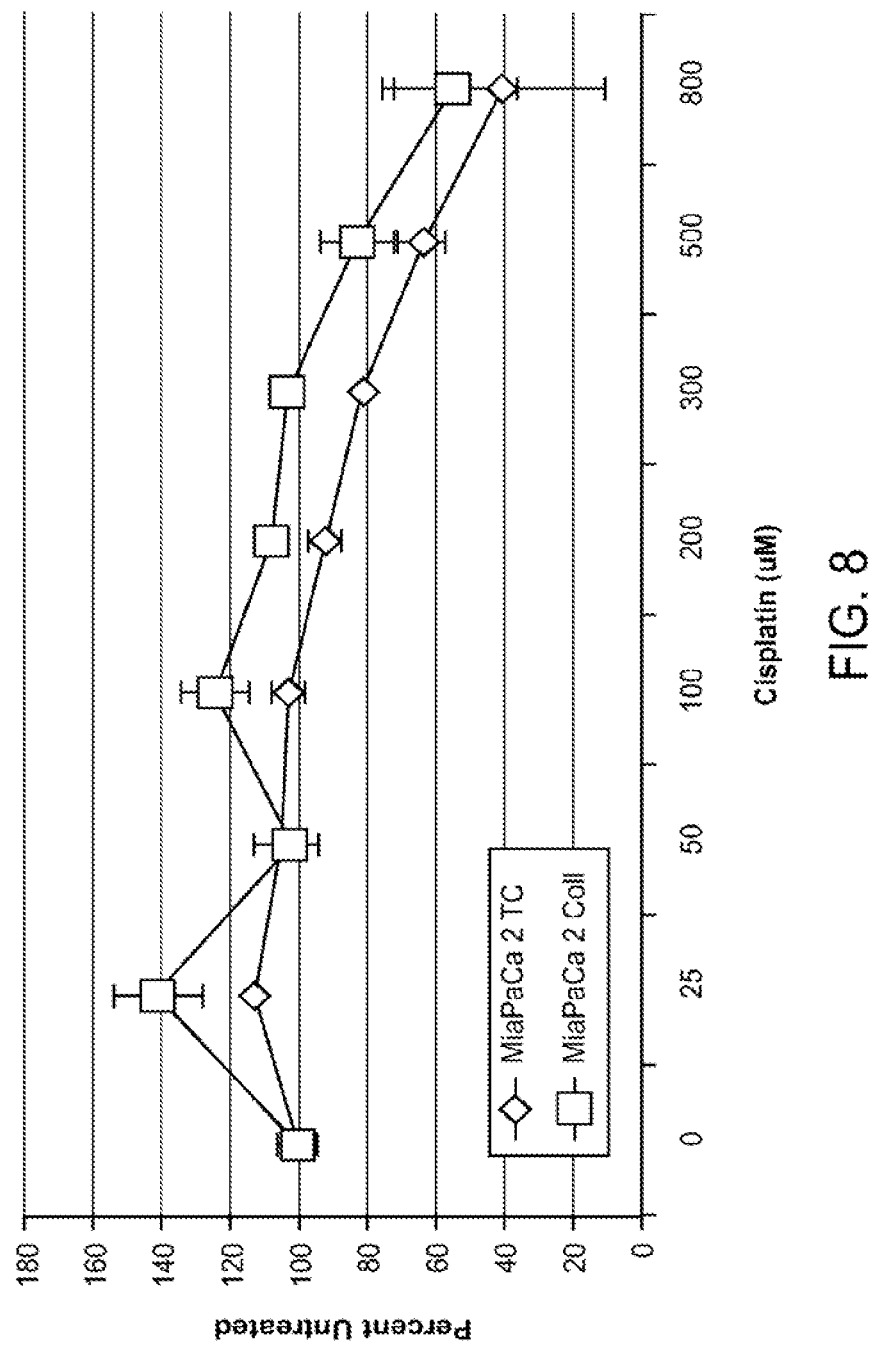
FIG. 8 shows the effect of increasing concentrations of cisplatin on the survival of MiaPaCa2 cells. Cells were cultured either in standard tissue culture plastic wells (diamonds) or in collagen-coated wells (squares).
Figure 9:
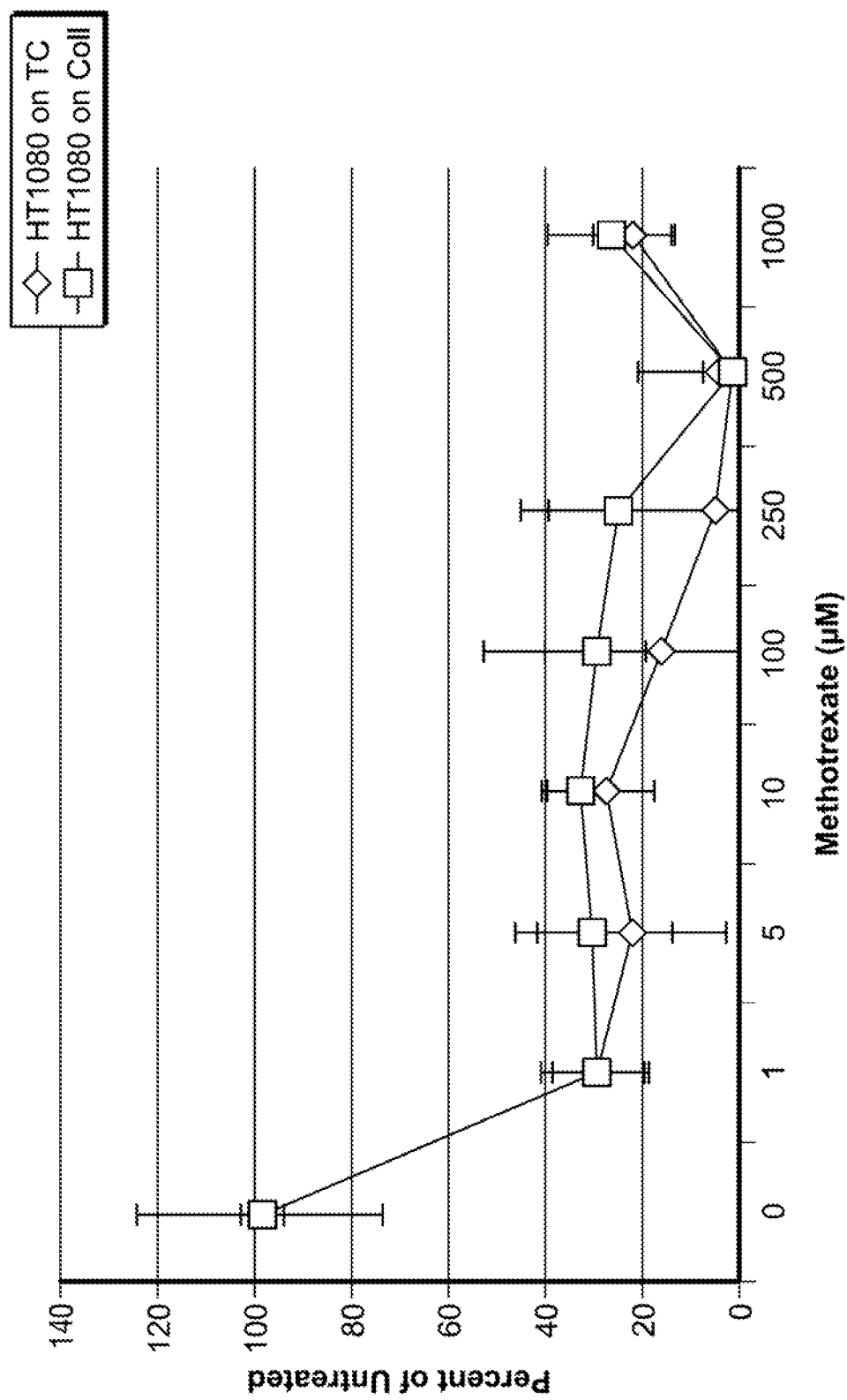
FIG. 9 shows the effect of increasing concentrations of methotrexate on the survival of HT1080 cells. Cells were cultured either in standard tissue culture plastic wells (diamonds) or in collagen-coated wells (squares).
Figure 10:
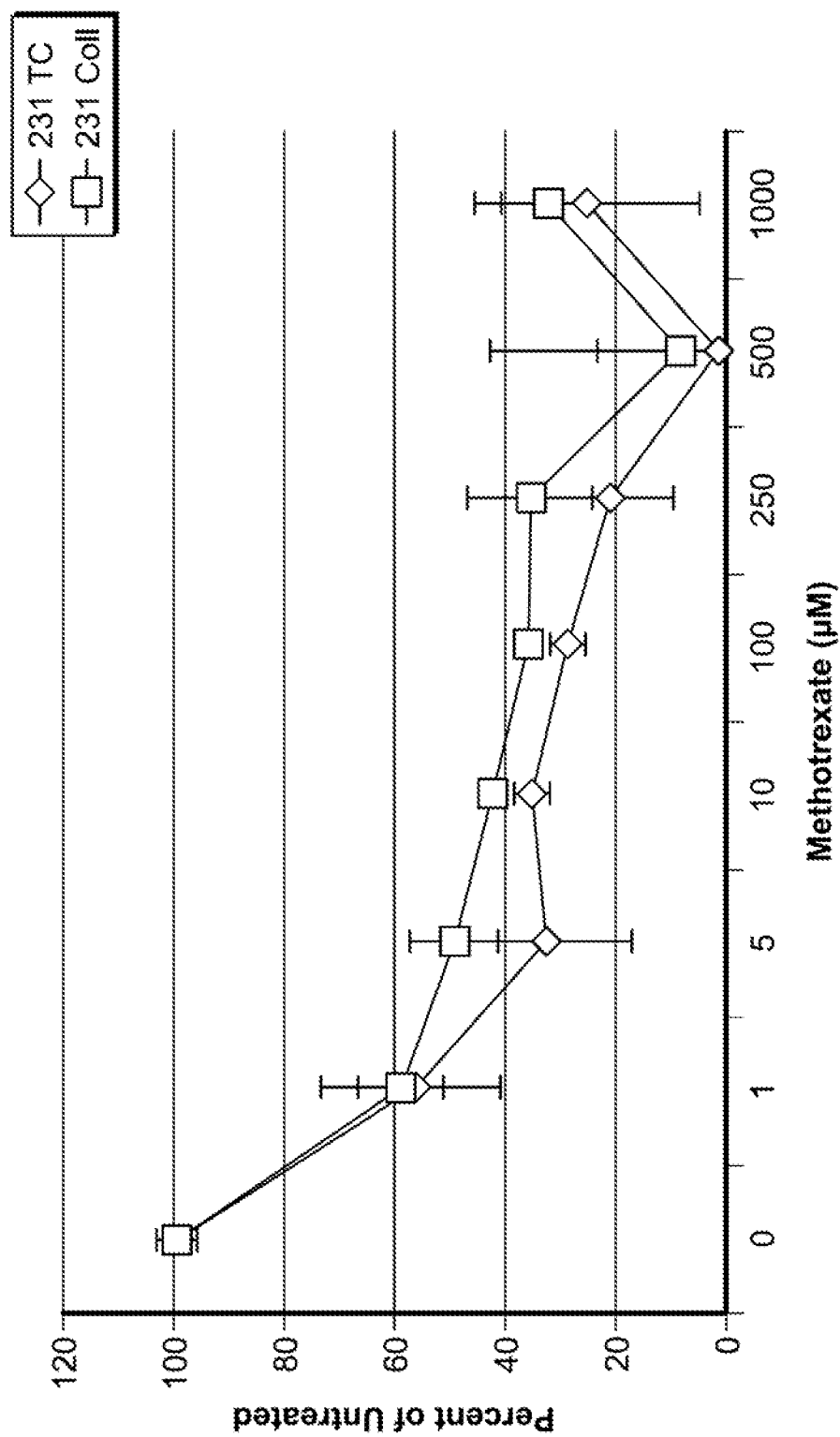
FIG. 10 shows the effect of increasing concentrations of methotrexate on the survival of MDA 231 cells. Cells were cultured either in standard tissue culture plastic wells (diamonds) or in collagen-coated wells (squares).
Figure 11:
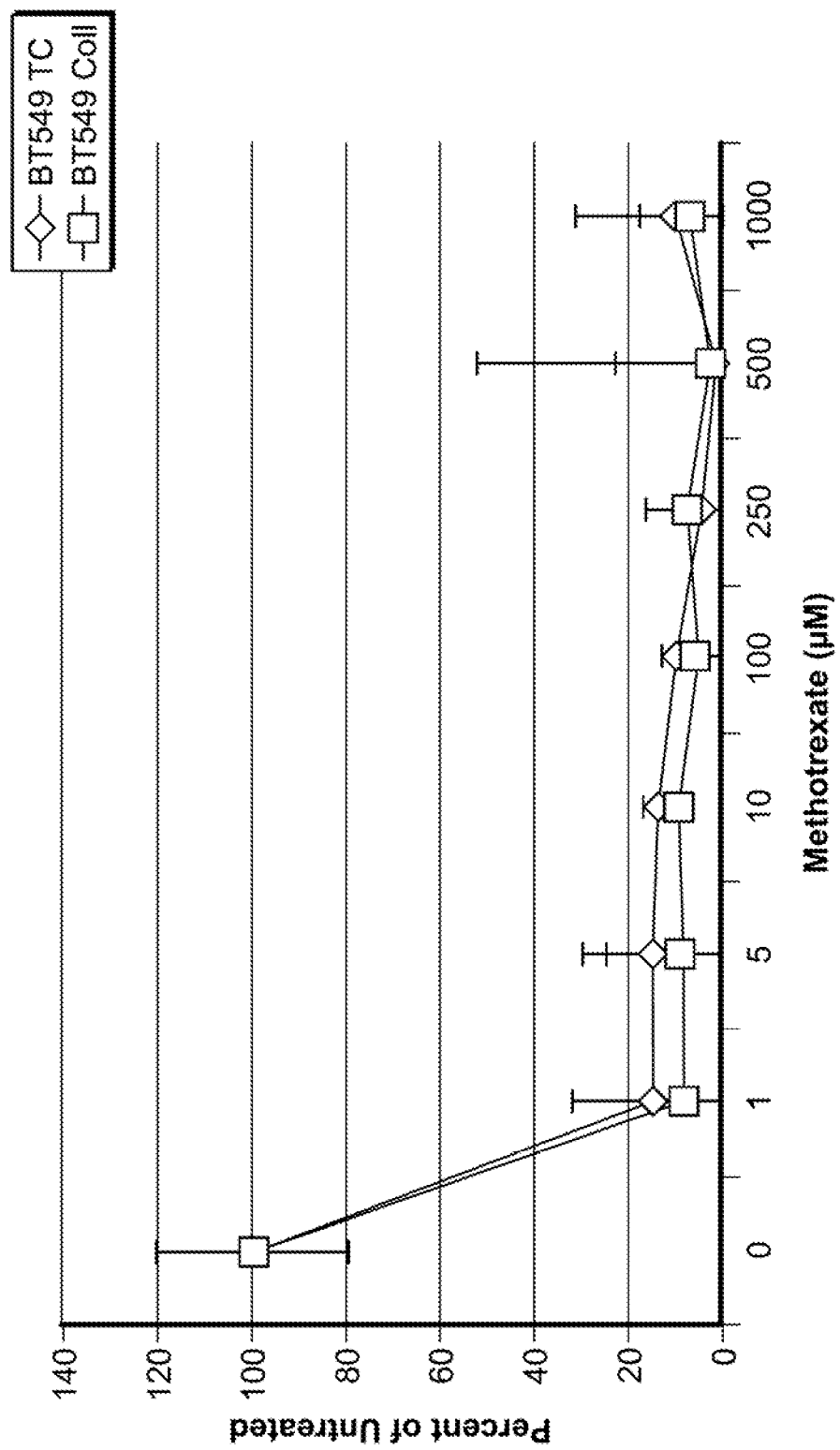
FIG. 11 shows the effect of increasing concentrations of methotrexate on the survival of BT549 cells. Cells were cultured either in standard tissue culture plastic wells (diamonds) or in collagen-coated wells (squares).
Figure 12:
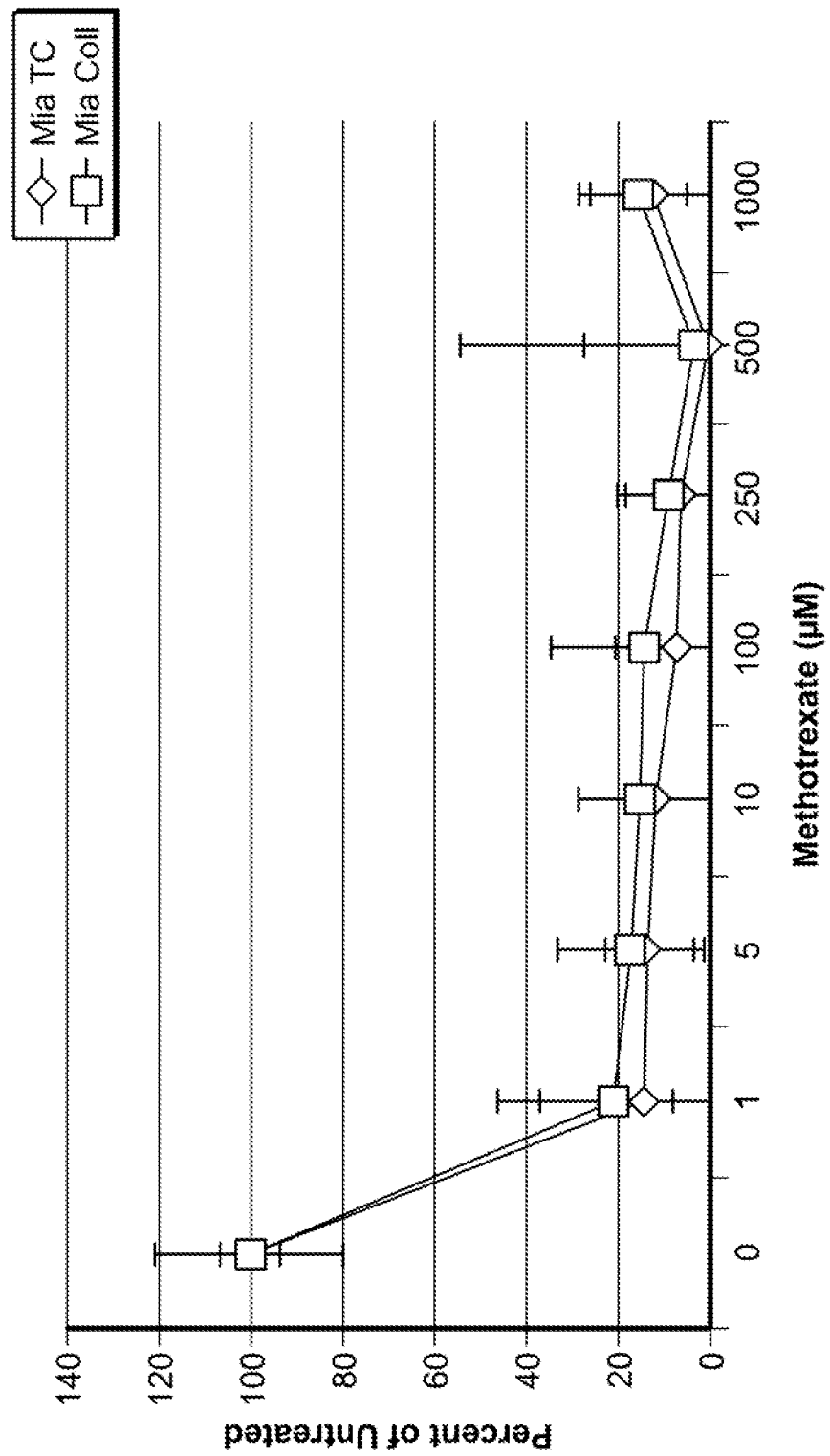
FIG. 12 shows the effect of increasing concentrations of methotrexate on the survival of MiaPaCa2 cells. Cells were cultured either in standard tissue culture plastic wells (diamonds) or in collagen-coated wells (squares).

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5" edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R.I., "Culture of Animal Cells: A Manual of Basic Technique," $4^{th}$ edition, John Wiley & Sons, Somerset, N.J., 2000; and the series "Methods in Enzymology," Academic Press, San Diego, Calif.

The inventors have discovered that traditional cell culture methods do not always accurately predict the sensitivity of a malignant cell to an anti-neoplastic agent. For example, malignant cells grown in standard plastic tissue culture vessels often exhibit sensitivity to certain drugs but, when the same cells are grown on an extracellular matrix (e.g., Type I collagen), they are resistant to the drug. In addition, the inventors have discovered that drug resistance of malignant cells grown in the presence of extracellular matrix (e.g., collagen) can depend on the activity of one or more lysyl oxidase-type enzymes. Further, the inventors have discovered that resistance of malignant cells to anti-neoplastic agents can be reversed by inhibiting the production and/or activity of one or more lysyl oxidase-type enzymes.

Cells Grown on an Extracellular Matrix Acquire Resistance to Anti-neoplastic Agents Malignant cell lines can be used as model systems for the identification of chemotherapeutic and anti-neoplastic agents. Conventionally, these cell lines are grown in tissue culture, a test molecule is added to the culture medium, and the growth of the cells is monitored. Substances that slow or block growth of the malignant cell line are identified as candidate anti-neoplastic agents.

One problem with this approach is that cells often develop resistance to chemotherapeutic and anti-neoplastic agents identified in this way. In the body, most cells grow in the presence of an extracellular matrix made up of collagen fibers embedded in a ground substance containing hyaluronic acid and proteoglycans. Therefore, it is possible that standard tissue culture conditions, in which cells are grown on a plastic surface, are not sufficiently representative of conditions in vivo. In support of this idea, the inventors have discovered that cells that exhibit sensitivity to known chemotherapeutic agents in standard tissue culture conditions, are resistant to the same agents when grown on a collagen substrate (see Example 1).

Accordingly, the present disclosure provides improved methods for identifying chemotherapeutic and anti-neoplastic agents, and methods for assessing the sensitivity of a malignant cell to a test molecule, by contacting malignant cells with a test molecule while the cells are growing in tissue culture in the presence of an extracellular matrix or matrix component (e.g., collagen). Cell survival is assayed in the absence and in the presence of the test molecule, and those test molecules that reduce cell survival are identified as anti-neoplastic agents.

The collagen can be of any type (there are 42 known human genes that encode different types of collagen), and can be present alone, as a mixture of different types of collagen, or as part of a collagen-containing matrix. If a single collagen type or a mixture of different collagens is used, they can be applied to the surface of a tissue culture vessel by a number of methods known in the art. Collagen-containing matrices are commercially available (e.g., Matrigel™, BD Biosciences, San Jose, Calif.; Cultrex® basement membrane extract, R&D Systems, Minneapolis, Minn.) or can be prepared by growing cells in tissue culture, then removing the cells (e.g., by trypsinization or EDTA), leaving a matrix elaborated by the cells on the surface of the culture vessel.

Reduction of cell survival can result from any process that slows the rate of cell division or proliferation of malignant cells, or that facilitates the death of malignant cells (e.g., by apoptosis or necrosis). Cell survival can be measured by any means known in the art. Exemplary methods for assessing cell survival include colony formation, Trypan Blue exclusion, incorporation of thymidine or bromodeoxyuridine as a measure of DNA replication, measurement of metabolic activity, measurement of ATP levels, and measurement of lactate dehydrogenase (LDH) levels.

Sensitivity of Malignant Cells Growing in the Presence of Collagen is Enhanced by Inhibitors of Lysyl Oxidase The inventors have also discovered that resistance to the effects of anti-neoplastic agents exhibited by malignant cells growing on an extracellular matrix (e.g., in the presence of collagen) can be reversed by inhibition of lysyl oxidase-type enzymes. Resistance to an anti-neoplastic agent occurs when the growth and/or survival of malignant cells is blocked upon initial contact with the anti-neoplastic agent but, over time, their growth and/or survival is restored in whole or in part.

Accordingly, the present disclosure provides methods and compositions for killing malignant cells, methods and compositions for enhancing the cell killing activity of anti-neoplastic agents, methods and compositions for reversing resistance of malignant cells to anti-neoplastic agents, methods and compositions for identifying molecules that enhance the cell killing activity of anti-neoplastic agents, and methods and compositions for assessing the sensitivity of a malignant cell to a test molecule. The methods and compositions utilize malignant cells growing in the presence of an extracellular matrix (e.g., collagen). In certain embodiments, the disclosed methods and compositions also include an inhibitor of a lysyl oxidase-type enzyme. However, it will be clear from the disclosure that methods and compositions that enhance killing of malignant cells by an anti-neoplastic agent, reverse resistance to anti-neoplastic agents, etc. can include molecules other that inhibitors of lysyl oxidase activity, inasmuch as methods for obtaining such molecules are provided.

Malignant cells, as used in the methods and compositions disclosed herein, can be in culture (e.g., in vitro, ex vivo) or can be present in situ (i.e., in a tumor). Inasmuch as the claimed methods can be practiced in situ, they can be used as methods of treatment for a number of neoplastic disorders (see below). Inhibitors of lysyl oxidase activity and/or other molecules that enhance the cell killing activity of an anti-neoplastic agent, can be administered to a subject alone or in conjunction with the anti-neoplastic agent.

An anti-neoplastic agent, as used in the disclosed methods and compositions, is any molecule that is used in the treatment of cancer, for example, a low molecular weight organic compound (i.e., a "small molecule" chemotherapeutic), a protein (e.g., a therapeutic antibody) or a nucleic acid (e.g., an antisense RNA or siRNA). Further description and examples of anti-neoplastic agents are provided in the specification infra.

In those embodiments in which an inhibitor of a lysyl oxidase-type enzyme is included, the inhibitor can be any type of molecule, including but not limited to a low molecular weight organic compound (i.e., "small molecule"), nucleic acid (e.g., triplex-forming oligonucleotide, antisense RNA, siRNA, micro RNA), polypeptide (e.g., antibody, peptide mimetic), polysaccharide, or glycoprotein. Means for the identification of inhibitors of a lysyl oxidase-type enzyme, and various exemplary inhibitors of a lysyl oxidase-type enzyme are disclosed in the present specification infra.

Inhibition of a lysyl oxidase-type enzyme, e.g., inhibition of lysyl oxidase activity, can be accomplished by any means known in the art, including, but not limited to, mutagenesis of a gene encoding a lysyl oxidase-type enzyme and/or of sequences regulating its expression; inhibition of transcription of a gene encoding a lysyl oxidase-type enzyme; alteration of a mRNA encoding a lysyl oxidase-type enzyme; inhibition of translation of a mRNA encoding a lysyl oxidase-type enzyme; and/or inhibition of the enzymatic activity of a lysyl oxidase-type enzyme.

Mutagenesis refers to changes in nucleotide sequence including insertion, deletion, inversion and/or substitution (i.e., replacement of one or more nucleotides with an equal number of different nucleotides or nucleotide analogues). Inhibition of transcription includes, but is not limited to, reduction in the frequency of transcription initiation (including reduction in RNA polymerase binding and the binding of transcription factors, or increased binding of transcriptional repressors); increase in the frequency of premature transcription termination and/or reduction in the rate of transcriptional elongation. Alteration of a mRNA includes, but is not limited to, changes in its primary sequence and/or its secondary structure, induction of errors in RNA processing; and/or cleavage of an intact mRNA, either endonucleolytically or exonucleolytically. Inhibition of translation includes, but is not limited to, reduction in the frequency of ribosome binding and/or translational initiation; reduction in frequency of initiation factor binding; increase in the frequency of premature translational termination and/or reduction in the rate of translation.

Inhibition of the enzymatic activity of a lysyl oxidase enzyme can be achieved using molecules that bind to a lysyl oxidase enzyme; e.g., low molecular weight organic compounds (i.e. "small molecules") and/or antibodies. Other exemplary inhibitors include nucleic acids, polypeptides and peptidomimetics. In certain embodiments, non-competitive inhibitors of a lysyl oxidase enzyme are used. Inhibition of lysyl oxidase activity can also be achieved by inhibiting the activity or production of enzymes that are involved in the synthesis of a lysyl oxidase enzyme or by inhibiting enzymes involved in the synthesis of a substrate of a lysyl oxidase enzyme or a precursor of said substrate.

Collagens

Collagen fibers are a major structural component of the extracellular matrix. There are 42 known genes in the human genome that encode collagen α-chains, and approximately 27 different types of collagen protein (some containing more than one collagen chain) have been identified. Fibril-forming collagens include Types I, II, III, V and XI; and a certain collagen type is often associated with a particular tissue type. Accordingly, the type of malignant cell under investigation (and its tissue origin) may suggest the use of a particular type of collagen in the methods and compositions disclosed herein. Other collagen types include the fibril-associated collagens type IX and XII, network-forming collagen type IV; collagen type VII, which forms anchoring fibrils; transmembrane collagen type XVII and collagen type XVIII, which serves as a core protein of a proteoglycan in the basal lamina. In certain cases, a particular collagen type can be associated with a disease state; for example, the extracellular matrix surrounding a tumor is often rich in Type I collagen, while healthy tissue often comprises an extracellular matrix rich in Type IV collagen. In certain embodiments of the present disclosure, cells are grown in the presence of one or more non-fibril-forming collagens together with one or more fibrillar collagens.

Lysyl Oxidase-type Enzymes

As used herein, the term "lysyl oxidase-type enzyme" refers to a member of a family of proteins that catalyzes oxidative deamination of ε-amino groups of lysine and hydroxylysine residues, resulting in conversion of peptidyl lysine to peptidyl-α-aminoadipic-δ-semialdehyde (allysine) and the release of stoichiometric quantities of ammonia and hydrogen peroxide:

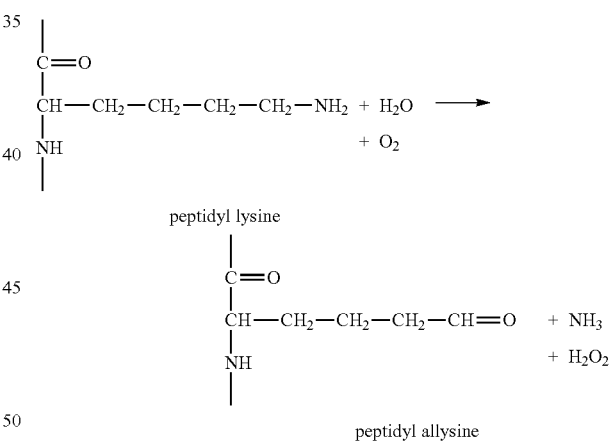

This reaction most often occurs extracellularly, on lysine residues in collagen and elastin. The aldehyde residues of allysine are reactive and can spontaneously condense with other allysine and lysine residues, resulting in crosslinking of collagen molecules to form collagen fibrils.

Lysyl oxidase-type enzymes have been purified from chicken, rat, mouse, bovines and humans. All lysyl oxidase-type enzymes contain a common catalytic domain, approximately 205 amino acids in length, located in the carboxy-terminal portion of the protein and containing the active site of the enzyme. The active site contains a copper-binding site which includes a conserved amino acid sequence containing four histidine residues which coordinate a Cu(II) atom. The active site also contains a lysyltyrosyl quinone (LTQ) cofactor, formed by intramolecular covalent linkage between a lysine and a tyrosine residue (corresponding to lys314 and tyr349 in rat lysyl oxidase, and to lys320 and tyr355 in human lysyl oxidase). The sequence surrounding the tyrosine residue that forms the LTQ cofactor is also conserved among lysyl oxidase-type enzymes. The catalytic domain also contains ten conserved cysteine residues, which participate in the formation of five disulfide bonds. The catalytic domain also includes a fibronectin binding domain. Finally, an amino acid sequence similar to a growth factor and cytokine receptor domain, containing four cysteine residues, is present in the catalytic domain.

The first member of this family of enzymes to be isolated and characterized was lysyl oxidase (EC 1.4.3.13); also known as protein-lysine 6-oxidase, protein-L-lysine:oxygen 6-oxidoreductase (deaminating), or LOX. See, e.g., Harris et al., *Biochim. Biophys. Acta* 341:332-344 (1974); Rayton et al., *J. Biol. Chem.* 254:621-626 (1979); Stassen, *Biophys. Acta* 438:49-60 (1976).

Additional lysyl oxidase-type enzymes were subsequently discovered. These proteins have been dubbed "LOX-like," or "LOXL." They all contain the common catalytic domain described above and have similar oxidative lysine deaminase enzymatic activity. Currently, five different lysyl oxidase-type enzymes are known to exist in both humans and mice: LOX and the four LOX related, or LOX-like proteins LOXL1 (also denoted "lysyl oxidase-like," "LOXL" or "LOL"), LOXL2 (also denoted "LOR-1"), LOXL3, and LOXL4. Each of the five lysyl oxidase-type enzymes reside on a different chromosome. See, for example, Molnar et al. (2003) *Biochim Biophys Acta.* 1647:220-224; Csiszar (2001) *Prog. Nucl. Acid Res.* 70:1-32; WO 01/83702 published on Nov. 8, 2001, and U.S. Pat. No. 6,300,092, all of which are incorporated by reference herein. A LOX-like protein termed LOXC, with some similarity to LOXL4 but with a different expression pattern, has been isolated from a murine EC cell line. Ito et al. (2001) *J. Biol. Chem.* 276:24023-24029. Two lysyl oxidase-type enzymes, DmLOXL-1 and DmLOXL-2, have been isolated from *Drosophila*.

Although all lysyl oxidase-type enzymes share a common catalytic domain, they also differ from one another, particularly within their amino-terminal regions. The four LOXL proteins have amino-terminal extensions, compared to LOX. Thus, while human preproLOX (i.e., the primary translation product prior to signal sequence cleavage, see below) contains 417 amino acid residues; LOXL1 contains 574, LOXL2 contains 638, LOXL3 contains 753 and LOXL4 contains 756.

Within their amino-terminal regions, LOXL2, LOXL3 and LOXL4 contain four repeats of the scavenger receptor cysteine-rich (SRCR) domain. These domains are not present in LOX or LOXL1. SRCR domains are found in secreted, transmembrane, or extracellular matrix proteins, and are known to mediate ligand binding in a number of secreted and receptor proteins. Hoheneste et al. (1999) *Nat. Struct. Biol.* 6:228-232; Sasaki et al. (1998) *EMBO J.* 17:1606-1613. In addition to its SRCR domains, LOXL3 contains a nuclear localization signal in its amino-terminal region. A proline-rich domain appears to be unique to LOXL1. Molnar et al. (2003) *Biochim. Biophys. Acta* 1647:220-224. The various lysyl oxidase-type enzymes also differ in their glycosylation patterns.

Tissue distribution also differs among the lysyl oxidase-type enzymes. Human LOX mRNA is highly expressed in the heart, placenta, testis, lung, kidney and uterus, but marginally in the brain and liver. mRNA for human LOXL1 is expressed in the placenta, kidney, muscle, heart, lung, and pancreas and, similar to LOX, is expressed at much lower levels in the brain and liver. Kim et al. (1995) *J. Biol. Chem.* 270:7176-7182. High levels of LOXL2 mRNA are expressed in the uterus, placenta, and other organs, but as with LOX and LOXL, low levels are expressed in the brain and liver. Jourdan Le-Saux et al. (1999) *J. Biol. Chem.* 274:12939-12944. LOXL3 mRNA is highly expressed in the testis, spleen, and prostate, moderately expressed in placenta, and not expressed in the liver, whereas high levels of LOXL4 mRNA are observed in the liver Huang et al. (2001) *Matrix Biol.* 20:153-157; Maki and Kivirikko (2001) *Biochem. J.* 355:381-387; Jourdan Le-Saux et al. (2001) *Genomics* 74:211-218; Asuncion et al. (2001) *Matrix Biol.* 20:487-491.

The expression and/or involvement of the different lysyl oxidase-type enzymes in diseases may also vary. See, for example, Kagen (1994) *Pathol. Res. Pract.* 190:910-919; Murawaki et al. (1991) *Hepatology* 14:1167-1173; Siegel et al. (1978) *Proc. Natl. Acad. Sci. USA* 75:2945-2949; Jourdan Le-Saux et al. (1994) *Biochem. Biophys. Res. Comm.* 199: 587-592; and Kim et al. (1999) *J. Cell Biochem.* 72:181-188. Lysyl oxidase-type enzymes have also been implicated in a number of cancers, including head and neck cancer, bladder cancer, colon cancer, esophageal cancer and breast cancer. See, for example, Wu et al. (2007) *Cancer Res.* 67:4123-4129; Gorough et al. (2007) *J. Pathol.* 212:74-82; Csiszar (2001) *Prog. Nucl. Acid Res.* 70:1-32 and Kirschmann et al. (2002) *Cancer Res.* 62:4478-4483.

Thus, although the lysyl oxidase-type enzymes exhibit some overlap in structure and function, each appears to have distinct functions as well. For example, targeted deletion of LOX appears to be lethal at parturition in mice, whereas LOXL1 deficiency causes no severe developmental phenotype. Hornstra et al. (2003) J. Biol. Chem. 278:14387-14393; Bronson et al. (2005) Neurosci. Lett. 390:118-122.

Although the most widely documented activity of lysyl oxidase-type enzymes is the oxidation of specific lysine residues in collagen and elastin outside of the cell, there is evidence that lysyl oxidase-type enzymes also participate in a number of intracellular processes. For example, there are reports that some lysyl oxidase-type enzymes regulate gene expression. Li et al. (1997) *Proc. Natl. Acad. Sci. USA* 94:12817-12822; Giampuzzi et al. (2000) *J. Biol. Chem.* 275: 36341-36349. In addition, LOX has been reported to oxidize lysine residues in histone H1. Additional extracellular activities of LOX include the induction of chemotaxis of monocytes, fibroblasts and smooth muscle cells. Lazarus et al. (1995) *Matrix Biol.* 14:727-731; Nelson et al. (1988) *Proc. Soc. Exp. Biol. Med.* 188:346-352. Expression of LOX itself is induced by a number of growth factors and steroids such as TGF-$\beta$, TNF-$\alpha$, and interferon. Csiszar (2001) *Prog. Nucl. Acid Res.* 70:1-32. Recent studies have attributed other roles to LOX in diverse biological functions such as developmental regulation, tumor suppression, cell motility, and cellular senescence.

Examples of lysyl oxidase (LOX) proteins from various sources include enzymes having an amino acid sequence substantially identical to a polypeptide expressed or translated from one of the following sequences: EMBL/GenBank accessions: M94054; AAA59525.1—mRNA; S45875; AAB23549.1—mRNA; 578694; AAB21243.1—mRNA; AF039291; AAD02130.1—mRNA; BC074820; AAH74820.1—mRNA; BC074872; AAH74872.1—mRNA; M84150; AAA59541.1—Genomic DNA. One embodiment of LOX is human lysyl oxidase (hLOX) preproprotein.

Exemplary disclosures of sequences encoding lysyl oxidase-like enzymes are as follows: LOXL1 is encoded by mRNA deposited at GenBank/EMBL BC015090; AAH15090.1; LOXL2 is encoded by mRNA deposited at GenBank/EMBL U89942; LOXL3 is encoded by mRNA deposited at GenBank/EMBL AF282619; AAK51671.1; and LOXL4 is encoded by mRNA deposited at GenBank/EMBL AF338441; AAK71934.1.

The primary translation product of the LOX protein, known as the prepropeptide, contains a signal sequence extending from amino acids 1-21. This signal sequence is released intracellularly by cleavage between Cys21 and Ala22, in both mouse and human LOX, to generate a 46-48 kDa propeptide form of LOX, also referred to herein as the full-length form. The propeptide is N-glycosylated during passage through the Golgi apparatus to yield a 50 kDa protein, then secreted into the extracellular environment. At this stage, the protein is catalytically inactive. A further cleavage, between Gly168 and Asp169 in mouse LOX, and between Gly174 and Asp175 in human LOX, generates the mature, catalytically active, 30-32 kDA enzyme, releasing a 18 kDa propeptide. This final cleavage event is catalyzed by the metalloendoprotease procollagen C-proteinase, also known as bone morphogenetic protein-1 (BMP-1). Interestingly, this enzyme also functions in the processing of LOX's substrate, collagen. The N-glycosyl units are subsequently removed.

Potential signal peptide cleavage sites have been predicted at the amino termini of LOXL, LOXL2, LOXL3, and LOXL4. The predicted signal cleavage sites are between Gly25 and Gln26 for LOXL, between Ala25 and Gln26, for LOXL2, between Gly25 and Ser26 for LOXL3 and between Arg23 and Pro24 for LOXL4.

A BMP-1 cleavage site in the LOXL (LOXL1) protein has been identified between Ser354 and Asp355. Borel et al. (2001) J. Biol. Chem.276:48944-48949. Potential BMP-1 cleavage sites in other lysyl oxidase-type enzymes have been predicted, based on the consensus sequence for BMP-1 cleavage in procollagens and pro-LOX being at an Ala/Gly-Asp sequence, often followed by an acidic or charged residue. A predicted BMP-1 cleavage site in LOXL3 is located between Gly447 and Asp448; processing at this site may yield a mature peptide of similar size to mature LOX. A potential cleavage site for BMP-1 was also identified within LOXL4, between residues Ala569 and Asp570. Kim et al. (2003) J. Biol. Chem. 278:52071-52074. LOXL2 may also be proteolytically cleaved analogously to the other members of the LOXL family and secreted. Akiri et al. (2003) Cancer Res. 63:1657-1666.

For the purposes of the present disclosure, the term "lysyl oxidase-type enzyme" encompasses all five of the lysine oxidizing enzymes discussed above, and also encompasses functional fragments and/or derivatives of LOX, LOXL1, LOXL2, LOXL3 and LOXL4 that substantially retain enzymatic activity; e.g., the ability to catalyze deamination of lysyl residues. Typically, a functional fragment or derivative retains at least 50% of its lysine oxidation activity. In some embodiments, a functional fragment or derivative retains at least 60%, at least 70%, at least 80%, at least 90%, at least 95%, at least 99% or 100% of its lysine oxidation activity.

It is also intended that a functional fragment of a lysyl oxidase-type enzyme can include conservative amino acid substitutions (with respect to the native polypeptide sequence) that do not substantially alter catalytic activity. The term "conservative amino acid substitution" refers to grouping of amino acids on the basis of certain common structures and/or properties. With respect to common structures, amino acids can be grouped into those with non-polar side chains (glycine, alanine, valine, leucine, isoleucine, methionine, proline, phenylalanine and tryptophan), those with uncharged polar side chains (serine, threonine, asparagine, glutamine, tyrosine and cysteine) and those with charged polar side chains (lysine, arginine, aspartic acid, glutamic acid and hsitidine). A group of amino acids containing aromatic side chains includes phenylalanine, tryptophan and tyrosine. Heterocyclic side chains are present in proline, tryptophan and histidine. Within the group of amino acids containing non-polar side chains, those with short hydrocarbon side chains (glycine, alanine, valine. leucine, isoleucine) can be distinguished from those with longer, non-hydrocarbon side chains (methionine, proline, phenylalanine, tryptophan). Within the group of amino acids with charged polar side chains, the acidic amino acids (aspartic acid, glutamic acid) can be distinguished from those with basic side chains (lysine, arginine and histidine).

A functional method for defining common properties of individual amino acids is to analyze the normalized frequencies of amino acid changes between corresponding proteins of homologous organisms (Schulz, G. E. and R. H. Schirmer, Principles of Protein Structure, Springer-Verlag, 1979). According to such analyses, groups of amino acids can be defined in which amino acids within a group are preferentially substituted for one another in homologous proteins, and therefore have similar impact on overall protein structure (Schulz, G. E. and R. H. Schirmer, Principles of Protein Structure, Springer-Verlag, 1979). According to this type of analysis, the following groups of amino acids that can be conservatively substituted for one another can be identified:

(i) amino acids containing a charged group, consisting of Glu, Asp, Lys, Arg and His, (ii) amino acids containing a positively-charged group, consisting of Lys, Arg and His, (iii) amino acids containing a negatively-charged group, consisting of Glu and Asp, (iv) amino acids containing an aromatic group, consisting of Phe, Tyr and Trp, (v) amino acids containing a nitrogen ring group, consisting of His and Trp, (vi) amino acids containing a large aliphatic non-polar group, consisting of Val, Leu and Ile, (vii) amino acids containing a slightly-polar group, consisting of Met and Cys, (viii) amino acids containing a small-residue group, consisting of Ser, Thr, Asp, Asn, Gly, Ala, Glu, Gln and Pro, (ix) amino acids containing an aliphatic group consisting of Val, Leu, Be, Met and Cys, and (x) amino acids containing a hydroxyl group consisting of Ser and Thr.

Thus, as exemplified above, conservative substitutions of amino acids are known to those of skill in this art and can be made generally without altering the biological activity of the resulting molecule. Those of skill in this art also recognize that, in general, single amino acid substitutions in non-essential regions of a polypeptide do not substantially alter biological activity. See, e.g., Watson, et al., "Molecular Biology of the Gene," 4th Edition, 1987, The Benjamin/Cummings Pub. Co., Menlo Park, Calif., p. 224.

For additional information regarding lysyl oxidase-type enzymes, see, e.g., Rucker et al. (1998) Am. J. Clin. Nutr. 67:996 S-1002S and Kagan et al. (2003) J. Cell. Biochem 88:660-672. See also co-owned United States patent application publications No. US 2009/0053224 (Feb. 26, 2009) and US 2009/0104201 (Apr. 23, 2009); the disclosures of which are incorporated by reference herein.

Modulators of Lysyl Oxidase-type Enzymes

Modulators of lysyl oxidase-type enzymes include both activators (agonists) and inhibitors (antagonists), and can be selected by using a variety of screening assays. In one embodiment, modulators can be identified by determining if a test compound binds to a lysyl oxidase-type enzyme;

wherein, if binding has occurred, the compound is a candidate modulator. Optionally, additional tests can be carried out on such a candidate modulator. Alternatively, a candidate compound can be contacted with a lysyl oxidase-type enzyme, and a biological activity of the enzyme can be assayed; a compound that alters the biological activity of the lysyl oxidase-type enzyme is a modulator of a lysyl oxidase-type enzyme. Generally, a compound that reduces a biological activity of a lysyl oxidase-type enzyme is an inhibitor of the enzyme. In certain embodiments, the biological activity is deamination.

Other methods of identifying modulators of lysyl oxidase-type enzymes include incubating a candidate compound in a cell culture containing one or more lysyl oxidase-type enzymes and assaying one or more biological activities or characteristics of the cells. Compounds that alter the biological activity or characteristic of the cells in the culture are potential modulators of lysyl oxidase-type enzymes. Biological activities that can be assayed include, for example, lysyl oxidase enzymatic activity (e.g., deamination), levels of lysyl oxidase-type enzyme, levels of mRNA encoding a lysyl oxidase-type enzyme, and/or one or more functions specific to a lysyl oxidase-type enzyme. In additional embodiments of the aforementioned assay, in the absence of contact with the candidate compound, the one or more biological activities or cell characteristics are correlated with levels or activity of a lysyl oxidase-type enzyme. For example, the biological activity can be cell viability or a cellular function such as migration, chemotaxis, epithelial-to-mesenchymal transition, or mesenchymal-to-epithelial transition, and the change is detected by comparison with one or more control or reference sample(s). For example, negative control samples can include a culture with decreased levels of a lysyl oxidase-type enzyme to which the candidate compound is added; or a culture with the same amount of lysyl oxidase-type enzyme as the test culture, but without addition of candidate compound. In some embodiments, separate cultures containing different levels of a lysyl oxidase-type enzyme are contacted with a candidate compound. If a change in biological activity is observed, and if the change is greater in the culture having higher levels of lysyl oxidase-type enzyme, the compound is identified as a modulator of a lysyl oxidase-type enzyme. Determination of whether the compound is an activator or an inhibitor of a lysyl oxidase-type enzyme may be apparent from the phenotype induced by the compound, or may require further assay, such as a test of the effect of the compound on lysyl oxidase enzymatic activity.

Methods for obtaining lysysl oxidase-type enzymes, either biochemically or recombinantly, as well as methods for cell culture and enzymatic assay to identify modulators of lysyl oxidase-type enzymes as described above, are known in the art.

The enzymatic activity of a lysyl oxidase-type enzyme can be assayed by a number of different methods. For example, lysyl oxidase enzymatic activity can be assessed by detecting and/or quantitating production of hydrogen peroxide, ammonium ion, and/or aldehyde, by assaying lysine oxidation and/or collagen crosslinking, or by measuring cellular invasive capacity, cell adhesion, cell growth or metastatic growth. See, for example, Trackman et al. (1981) *Anal. Biochem.* 113:336-342; Kagan et al. (1982) *Meth. Enzymol.* 82A:637-649; Palamakumbura et al. (2002) *Anal. Biochem.* 300:245-251; Albini et al. (1987) *Cancer Res.* 47:3239-3245; Kamath et al. (2001) *Cancer Res.* 61:5933-5940; U.S. Pat. No. 4,997,854 and U.S. patent application publication No. 2004/0248871.

Test compounds include, but are not limited to, small organic compounds (e.g., organic molecules having a molecular weight between about 50 and about 2,500 Da), nucleic acids or proteins, for example. The compound or plurality of compounds may be chemically synthesized or microbiologically produced and/or comprised in, for example, samples, e.g., cell extracts from, e.g., plants, animals or microorganisms. Furthermore, the compound(s) may be known in the art but hitherto not known to be capable of modulating a lysyl oxidase-type enzyme. The reaction mixture for assaying for a modulator of a lysyl oxidase-type enzyme can be a cell-free extract or can comprise a cell culture or tissue culture. A plurality of compounds can be, e.g., added to a reaction mixture, added to a culture medium, introduced into a cell or administered to a transgenic animal. The cell or tissue employed in the assay can be, for example, a bacterial cell, a fungal cell, an insect cell, a vertebrate cell, a mammalian cell, a primate cell, a human cell or can comprise or be obtained from a non-human transgenic animal.

Several methods are known to the person skilled in the art for producing and screening large libraries to identify compounds having specific affinity for a target, such as a lysyl oxidase-type enzyme. These methods include the phage-display method in which randomized peptides are displayed from phage and screened by affinity chromatography using an immobilized receptor. See, e.g., WO 91/17271, WO 92/01047, and U.S. Pat. No. 5,223,409. In another approach, combinatorial libraries of polymers immobilized on a solid support (e.g., a "chip") are synthesized using photolithography. See, e.g., U.S. Pat. No. 5,143,854, WO 90/15070 and WO 92/10092. The immobilized polymers are contacted with a labeled receptor (e.g., a lysyl oxidase-type enzyme) and the support is scanned to determine the location of label, to thereby identify polymers binding to the receptor.

The synthesis and screening of peptide libraries on continuous cellulose membrane supports that can be used for identifying binding ligands of a polypeptide of interest (e.g., a lysyl oxidase-type enzyme) is described, for example, in Kramer (1998) Methods Mol. Biol. 87: 25-39. Ligands identified by such an assay are candidate modulators of the protein of interest, and can be selected for further testing. This method can also be used, for example, for determining the binding sites and the recognition motifs in a protein of interest. See, for example Rudiger (1997) EMBO J. 16:1501-1507 and Weiergraber (1996) FEBS Lett. 379:122-126.

WO 98/25146 describes additional methods for screening libraries of complexes for compounds having a desired property, e.g., the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with a lysyl oxidase-type enzyme are, for example, in vitro screening with a phage display system, filter binding assays, and "real time" measuring of interaction using, for example, the BIAcore apparatus (Pharmacia).

All these methods can be used in accordance with the present disclosure to identify activators/agonists and inhibitors/antagonists of lysyl oxidase-type enzymes or related polypeptides.

Another approach to the synthesis of modulators of lysyl oxidase-type enzymes is to use mimetic analogs of peptides. Mimetic peptide analogues can be generated by, for example, substituting stereoisomers, i.e. D-amino acids, for naturally-occurring amino acids; see e.g., Tsukida (1997) J. Med.

Chem. 40:3534-3541. Furthermore, pro-mimetic components can be incorporated into a peptide to reestablish conformational properties that may be lost upon removal of part of the original polypeptide. See, e.g., Nachman (1995) Regul. Pept. 57:359-370.

Another method for constructing peptide mimetics is to incorporate achiral-amino acid residues into a peptide, resulting in the substitution of amide bonds by polymethylene units of an aliphatic chain. Banerjee (1996) Biopolymers 39:769-777. Superactive peptidomimetic analogues of small peptide hormones in other systems have been described. Zhang (1996) Biochem. Biophys. Res. Commun. 224:327-331.

Peptide mimetics of a modulator of a lysyl oxidase-type enzyme can also be identified by the synthesis of peptide mimetic combinatorial libraries through successive amide alkylation, followed by testing of the resulting compounds, e.g., for their binding and immunological properties. Methods for the generation and use of peptidomimetic combinatorial libraries have been described. See, for example, Ostresh, (1996) *Methods in Enzymology* 267:220-234 and Dorner (1996) *Bioorg. Med. Chem.* 4:709-715. Furthermore, a three-dimensional and/or crystallographic structure of one or more lysyl oxidase enzymes can be used for the design of peptide mimetic inhibitors of lysyl oxidase activity. Rose (1996) *Biochemistry* 35:12933-12944; Rutenber (1996) *Bioorg. Med. Chem.* 4:1545-1558.

The structure-based design and synthesis of low-molecular-weight synthetic molecules that mimic the activity of native biological polypeptides is further described in, e.g., Dowd (1998) Nature Biotechnol. 16:190-195; Kieber-Emmons (1997) Current Opinion Biotechnol. 8:435-441; Moore (1997) Proc. West Pharmacol. Soc. 40:115-119; Mathews (1997) Proc. West Pharmacol. Soc. 40:121-125; and Mukhija (1998) European J. Biochem. 254:433-438.

It is also well known to the person skilled in the art that it is possible to design, synthesize and evaluate mimetics of small organic compounds that, for example, can act as a substrate or ligand of a lysyl oxidase-type enzyme. For example, it has been described that D-glucose mimetics of hapalosin exhibited similar efficiency as hapalosin in antagonizing multidrug resistance assistance-associated protein in cytotoxicity. Dinh (1998) J. Med. Chem. 41:981-987.

The structure of one or more lysyl oxidase-type enzymes can be investigated to guide the selection of modulators such as, for example, small molecules, peptides, peptide mimetics and antibodies. Structural properties of lysyl oxidase-type enzymes can help to identify natural or synthetic molecules that bind to, or function as a ligand, substrate, binding partner or the receptor of, a lysyl oxidase-type enzyme. See, e.g., Engleman (1997) *J. Clin. Invest.* 99:2284-2292. For example, folding simulations and computer redesign of structural motifs of lysyl oxidase-type enzymes can be performed using appropriate computer programs. Olszewski (1996) *Proteins* 25:286-299; Hoffman (1995) *Comput. Appl. Biosci.* 11:675-679. Computer modeling of protein folding can be used for the conformational and energetic analysis of detailed peptide and protein structure. Monge (1995) *J. Mol. Biol.* 247:995-1012; Renouf (1995) *Adv. Exp. Med. Biol.* 376:37-45. Appropriate programs can be used for the identification of sites, on lysyl oxidase-type enzymes, that interact with ligands and binding partners, using computer assisted searches for complementary peptide sequences. Fassina (1994) *Immunomethods* 5:114-120. Additional systems for the design of protein and peptides are described, for example in Berry (1994) *Biochem. Soc. Trans.* 22:1033-1036; Wodak (1987), *Ann. N.Y. Acad. Sci.* 501:1-13; and Pabo (1986) *Biochemistry* 25:5987-5991. The results obtained from the above-described structural analyses can be used for, e.g., the preparation of organic molecules, peptides and peptide mimetics that function as modulators of the activity of a lysyl oxidase-type enzyme.

An inhibitor of a lysyl oxidase-type enzyme can be a competitive inhibitor, an uncompetitive inhibitor, a mixed inhibitor or a non-competitive inhibitor. Competitive inhibitors often bear a structural similarity to substrate, usually bind to the active site, and are more effective at lower substrate concentrations. The apparent $K_M$ is increased in the presence of a competitive inhibitor. Uncompetitive inhibitors generally bind to the enzyme-substrate complex or to a site that becomes available after substrate is bound at the active site and may distort the active site. Both the apparent $K_M$ and the $V_{max}$ are decreased in the presence of an uncompetitive inhibitor, and substrate concentration has little or no effect on inhibition. Mixed inhibitors are capable of binding both to free enzyme and to the enzyme-substrate complex and thus affect both substrate binding and catalytic activity. Non-competitive inhibition is a special case of mixed inhibition in which the inhibitor binds enzyme and enzyme-substrate complex with equal avidity, and inhibition is not affected by substrate concentration. Non-competitive inhibitors generally bind to enzyme at a region outside the active site. For additional details on enzyme inhibition see, for example, Voet et al. (2008) supra.

Antibodies

In certain embodiments, a modulator of a lysyl oxidase-type enzyme is an antibody. In additional embodiments, an antibody is an inhibitor of the activity of a lysyl oxidase-type enzyme.

As used herein, the term "antibody" means an isolated or recombinant polypeptide binding agent that comprises peptide sequences (e.g., variable region sequences) that specifically bind an antigenic epitope. The term is used in its broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and Fab$_2$, so long as they exhibit the desired biological activity. The term "human antibody" refers to antibodies containing sequences of human origin, except for possible non-human CDR regions, and does not imply that the full structure of an immunoglobulin molecule be present, only that the antibody has minimal immunogenic effect in a human (i.e., does not induce the production of antibodies to itself).

An "antibody fragment" comprises a portion of an full-length antibody, for example, the antigen binding or variable region of a full-length antibody. Examples of antibody fragments include Fab, Fab', F(ab')$_2$, and Fv fragments; diabodies; linear antibodies (Zapata et al. (1995) *Protein Eng.* 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or an isolated $V_H$ or $V_L$ region comprising only three of the six CDRs specific for an antigen) has the ability to recognize and bind antigen, although at a lower affinity than does the entire $F_v$ fragment.

The "$F_{ab}$" fragment also contains, in addition to heavy and light chain variable regions, the constant domain of the light chain and the first constant domain (CHO of the heavy chain. Fab fragments were originally observed following papain digestion of an antibody. Fab' fragments differ from Fab fragments in that Fab' fragments contain several additional residues at the carboxy terminus of the heavy chain $CH_1$ domain, including one or more cysteines from the antibody hinge region. F(ab')$_2$ fragments contain two Fab fragments joined, near the hinge region, by disulfide bonds, and were originally observed following pepsin digestion of an antibody. Fab'-SH is the designation herein for Fab' fragments in which the cysteine residue(s) of the constant domains bear a free thiol group. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to five major classes: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun, in *The Pharmacology of Monoclonal Antibodies*, vol. 113 (Rosenburg and Moore eds.) Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain, thereby creating two antigen-binding sites. Diabodies are additionally described, for example, in EP 404,097; WO 93/11161 and Hollinger et al. (1993) Proc. Natl. Acad. Sci. USA 90:6444-6448.

An "isolated" antibody is one that has been identified and separated and/or recovered from a component of its natural environment. Components of its natural environment may include enzymes, hormones, and other proteinaceous or non-proteinaceous solutes. In some embodiments, an isolated antibody is purified (1) to greater than 95% by weight of antibody as determined by the Lowry method, for example, more than 99% by weight, (2) to a degree sufficient to obtain at least 15 residues of N-terminal or internal amino acid sequence, e.g., by use of a spinning cup sequenator, or (3) to homogeneity by gel electrophoresis (e.g., SDS-PAGE) under reducing or nonreducing conditions, with detection by Coomassie blue or silver stain. The term "isolated antibody" includes an antibody in situ within recombinant cells, since at least one component of the antibody's natural environment will not be present. In certain embodiments, isolated antibody is prepared by at least one purification step.

In some embodiments, an antibody is a humanized antibody or a human antibody. Humanized antibodies include human immununoglobulins (recipient antibody) in which residues from a complementary determining region (CDR) of the recipient are replaced by residues from a CDR of a non-human species (donor antibody) such as mouse, rat or rabbit having the desired specificity, affinity and capacity. Thus, humanized forms of non-human (e.g., murine) antibodies are chimeric immunoglobulins which contain minimal sequence derived from non-human immunoglobulin. The non-human sequences are located primarily in the variable regions, particularly in the complementarity-determining regions (CDRs). In some embodiments, Fv framework residues of the human immunoglobulin are replaced by corresponding non-human residues. Humanized antibodies can also comprise residues that are found neither in the recipient antibody nor in the imported CDR or framework sequences. In certain embodiments, a humanized antibody comprises substantially all of at least one, and typically two, variable domains, in which all or substantially all of the CDRs correspond to those of a non-human immunoglobulin and all or substantially all of the framework regions are those of a human immunoglobulin consensus sequence. For the purposes of the present disclosure, humanized antibodies can also include immunoglobulin fragments, such as Fv, Fab, Fab', F(ab')$_2$ or other antigen-binding subsequences of antibodies.

The humanized antibody can also comprise at least a portion of an immunoglobulin constant region (Fc), typically that of a human immunoglobulin. See, for example, Jones et al. (1986) *Nature* 321:522-525; Riechmann et al. (1988) *Nature* 332:323-329; and Presta (1992) *Curr. Op. Struct. Biol.* 2:593-596.

Methods for humanizing non-human antibodies are known in the art. Generally, a humanized antibody has one or more amino acid residues introduced into it from a source that is non-human. These non-human amino acid residues are often referred to as "import" or "donor" residues, which are typically obtained from an "import" or "donor" variable domain. For example, humanization can be performed essentially according to the method of Winter and co-workers, by substituting rodent CDRs or CDR sequences for the corresponding sequences of a human antibody. See, for example, Jones et al., supra; Riechmann et al., supra and Verhoeyen et al. (1988) *Science* 239:1534-1536. Accordingly, such "humanized" antibodies include chimeric antibodies (U.S. Pat. No. 4,816,567), wherein substantially less than an intact human variable domain has been substituted by the corresponding sequence from a non-human species. In certain embodiments, humanized antibodies are human antibodies in which some CDR residues and optionally some framework region residues are substituted by residues from analogous sites in rodent antibodies (e.g., murine monoclonal antibodies).

Human antibodies can also be produced, for example, by using phage display libraries. Hoogenboom et al. (1991) *J. Mol. Biol,* 227:381; Marks et al. (1991) *J. Mol. Biol.* 222:581. Other methods for preparing human monoclonal antibodies are described by Cole et al. (1985) "Monoclonal Antibodies and Cancer Therapy," Alan R. Liss, p. 77 and Boerner et al. (1991) J. Immunol. 147:86-95.

Human antibodies can be made by introducing human immunoglobulin loci into transgenic animals (e.g., mice) in which the endogenous immunoglobulin genes have been partially or completely inactivated. Upon immunological challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al. (1992) Bio/Technology 10:779-783 (1992); Lonberg et al. (1994) *Nature* 368: 856-859; Morrison (1994) *Nature* 368: 812-813; Fishwald et al. (1996) *Nature Biotechnology* 14:845-851; Neuberger (1996) *Nature Biotechnology* 14:826; Lonberg et al. (1995) *Intern. Rev. Immunol.* 13:65-93.

Antibodies can be affinity matured using known selection and/or mutagenesis methods as described above. In some embodiments, affinity matured antibodies have an affinity which is five times or more, ten times or more, twenty times or more, or thirty times or more than that of the starting antibody (generally murine, rabbit, chicken, humanized or human) from which the matured antibody is prepared.

An antibody can also be a bispecific antibody. Bispecific antibodies are monoclonal, and may be human or humanized antibodies that have binding specificities for at least two different antigens. In the present case, the two different binding specificities can be directed to two different lysyl oxidase-type enzymes, or to two different epitopes on a single lysyl oxidase-type enzyme.

An antibody as disclosed herein can also be an immunoconjugate. Such immunoconjugates comprise an antibody (e.g., an antibody to a lysyl oxidase-type enzyme) conjugated to a second molecule, such as a reporter An immunoconjugate can also comprise an antibody conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

An antibody that "specifically binds to" or is "specific for" a particular polypeptide or an epitope on a particular polypeptide is one that binds to that particular polypeptide or epitope without substantially binding to any other polypeptide or polypeptide epitope. In some embodiments, an antibody of the present disclosure specifically binds to its target with a dissociation constant ($K_d$) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM; in the form of monoclonal antibody, scFv, Fab, or other form of antibody measured at a temperature of about 4° C., 25° C., 37° C. or 42° C.

In certain embodiments, an antibody of the present disclosure binds to one or more processing sites (e.g., sites of proteolytic cleavage) in a lysyl oxidase-type enzyme, thereby effectively blocking processing of the proenzyme or preproenzyme to the catalytically active enzyme, thereby reducing the activity of the lysyl oxidase-type enzyme.

In certain embodiments, an antibody according to the present disclosure binds to human LOX with a greater binding affinity, for example, at least 10 times, at least 100 times, or even at least 1000 times greater, than its binding affinity to other lysyl oxidase-type enzymes, e.g., LOXL1, LOXL2, LOXL3, and LOXL4.

In additional embodiments, an antibody according to the present disclosure binds to human LOXL2 with a greater binding affinity, for example, at least 10 times, at least 100 times, or even at least 1000 times greater, than its binding affinity to other lysyl oxidase-type enzymes, e.g., LOX, LOXL1, LOXL3, and LOXL4.

Optionally, an antibody according to the present disclosure not only binds to a lysyl oxidase-type enzyme but also reduces or inhibits uptake or internalization of the lysyl oxidase-type enzyme, e.g., via integrin beta 1 or other cellular receptors or proteins. Such an antibody could, for example, bind to extracellular matrix proteins, cellular receptors, and/or integrins.

Exemplary antibodies that recognize lysyl oxidase-type enzymes, and additional disclosure relating to antibodies to lysyl oxidase enzymes, is provided in co-owned U.S. Patent Application Publication No. US 2009/0053224 (Feb. 26, 2009), the disclosure of which is incorporated by reference.

Polynucleotides for Modulating Expression of Lysyl Oxidase-type Enzymes

Antisense

Modulation (generally inhibition) of a lysyl oxidase-type enzyme can be effected by down-regulating expression of the lysyl oxidase-type enzyme at either the transcriptional or translational level. One such method of modulation involves the use of antisense oligo- or polynucleotides capable of sequence-specific binding with a mRNA transcript encoding a lysyl oxidase-type enzyme.

Binding of an antisense oligonucleotide (or antisense oligonucleotide analogue) to a target mRNA molecule can lead to the enzymatic cleavage of the hybrid by intracellular RNase H. In certain cases, formation of an antisense RNA-mRNA hybrid can interfere with correct splicing. In both cases, the number of intact, functional target mRNAs, suitable for translation, is reduced or eliminated. In other cases, binding of an antisense oligonucleotide or oligonucleotide analogue to a target mRNA can prevent (e.g., by steric hindrance) ribosome binding, thereby preventing translation of the mRNA.

Antisense oligonucleotides can comprise any type of nucleotide subunit, e.g., they can be DNA, RNA, analogues such as peptide nucleic acids (PNA), or mixtures of the preceding. RNA oligonucleotides form a more stable duplex with a target mRNA molecule, but the unhybridized oligonucleotides are less stable intracellularly than other types of oligonucleotides and oligonucleotide analogues. This can be counteracted by expressing RNA oligonucleotides inside a cell using vectors designed for this purpose. This approach may be used, for example, when attempting to target a mRNA that encodes an abundant and long-lived protein.

Additional considerations can be taken into account when designing antisense oligonucleotides, including: (i) sufficient specificity in binding to the target sequence; (ii) solubility in water; (iii) stability against intra- and extracellular nucleases; (iv) ability to penetrate the cell membrane; and (v) when used to treat an organism, low toxicity.

Algorithms for identifying oligonucleotide sequences with the highest predicted binding affinity for their target mRNA, based on a thermodynamic cycle that accounts for the energy of structural alterations in both the target mRNA and the oligonucleotide, are available. For example, Walton et al. (1999) *Biotechnol. Bioeng.* 65:1-9 used such a method to design antisense oligonucleotides directed to rabbit-globin (RBG) and mouse tumor necrosis factor-(TNF) transcripts. The same research group has also reported that the antisense activity of rationally selected oligonucleotides against three model target mRNAs (human lactate dehydrogenase A and B and rat gp130) in cell culture proved effective in almost all cases. This included tests against three different targets in two cell types with phosphodiester and phosphorothioate oligonucleotide chemistries.

In addition, several approaches for designing and predicting efficiency of specific oligonucleotides using an in vitro system are available. See, e.g., Matveeva et al. (1998) *Nature Biotechnology* 16:1374-1375.

An antisense oligonucleotide according to the present disclosure includes a polynucleotide or a polynucleotide analogue of at least 10 nucleotides, for example, between 10 and 15, between 15 and 20, at least 17, at least 18, at least 19, at least 20, at least 22, at least 25, at least 30, or even at least 40 nucleotides. Such a polynucleotide or polynucleotide analogue is able to anneal or hybridize (i.e., form a double-stranded structure on the basis of base complementarity) in vivo, under physiological conditions, with a mRNA encoding a lysyl oxidase-type enzyme.

Antisense oligonucleotides according to the present disclosure can be expressed from a nucleic acid construct administered to a cell or tissue. Optionally, expression of the antisense sequences is controlled by an inducible promoter, such that expression of antisense sequences can be switched on and off in a cell or tissue. Alternatively antisense oligonucleotides can be chemically synthesized and administered directly to a cell or tissue, as part of, for example, a pharmaceutical composition.

Antisense technology has led to the generation of highly accurate antisense design algorithms and a wide variety of oligonucleotide delivery systems, thereby enabling those of ordinary skill in the art to design and implement antisense approaches suitable for downregulating expression of known sequences. For additional information relating to antisense technology, see, for example, Lichtenstein et al., "Antisense Technology: A Practical Approach," Oxford University Press, 1998.

Small RNA and RNAi

Another method for inhibition of a lysyl oxidase-type enzyme is RNA interference (RNAi), an approach which utilizes double-stranded small interfering RNA (siRNA) molecules that are homologous to a target mRNA and lead to its degradation. Carthew (2001) Curr. Opin. Cell. Biol. 13:244-248.

RNA interference is typically a two-step process. In the first step, which is termed as the initiation step, input dsRNA is digested into 21-23 nucleotide (nt) small interfering RNAs (siRNAs), probably by the action of Dicer, a member of the RNase III family of double-strand-specific ribonucleases, which cleaves double-stranded RNA in an ATP-dependent manner. Input RNA can be delivered, e.g., directly or via a transgene or a virus. Successive cleavage events degrade the RNA to 19-21 by duplexes (siRNA), each with 2-nucleotide 3' overhangs. Hutvagner et al. (2002) Curr. Opin. Genet. Dev. 12:225-232; Bernstein (2001) Nature 409:363-366.

In the second, effector step, siRNA duplexes bind to a nuclease complex to form the RNA-induced silencing complex (RISC). An ATP-dependent unwinding of the siRNA duplex is required for activation of the RISC. The active RISC (containing a single siRNA and an RNase) then targets the homologous transcript by base pairing interactions and typically cleaves the mRNA into fragments of approximately 12 nucleotides, starting from the 3' terminus of the siRNA. Hutvagner et al., supra; Hammond et al. (2001) Nat. Rev. Gen. 2:110-119; Sharp (2001) Genes. Dev. 15:485-490.

RNAi and associated methods are also described in Tuschl (2001) Chem. Biochem. 2:239-245; Cullen (2002) Nat. Immunol. 3:597-599; and Brantl (2002) Biochem. Biophys. Acta. 1575:15-25.

An exemplary strategy for synthesis of RNAi molecules suitable for use with the present disclosure, as an inhibitor of one or more lysyl oxidase-type enzymes, is to scan the appropriate mRNA sequence downstream of the start codon for AA dinucleotide sequences. Each AA, plus the downstream (i.e., 3' adjacent) 19 nucleotides, is recorded as a potential siRNA target site. Target sites in coding regions are preferred, since proteins that bind in untranslated regions (UTRs) of a mRNA, and/or translation initiation complexes, may interfere with binding of the siRNA endonuclease complex. Tuschl (2001) supra. It will be appreciated though, that siRNAs directed at untranslated regions can also be effective, as has been demonstrated in the case wherein siRNA directed at the 5' UTR of the GAPDH gene mediated about 90% decrease in cellular GAPDH mRNA and completely abolished protein level (www.ambion.com/techlib/tn/91/912.html). Once a set of potential target sites is obtained, as described above, the sequences of the potential targets are compared to an appropriate genomic database (e.g., human, mouse, rat etc.) using a sequence alignment software, (such as the BLAST software available from NCBI at www.ncbi.nlm.nih.gov/BLAST/). Potential target sites that exhibit significant homology to other coding sequences are rejected.

Qualifying target sequences are selected as templates for siRNA synthesis. Selected sequences can include those with low G/C content as these have been shown to be more effective in mediating gene silencing, compared to those with G/C content higher than 55%. Several target sites can be selected along the length of the target gene for evaluation. For better evaluation of the selected siRNAs, a negative control is used in conjunction. Negative control siRNA can include a sequence with the same nucleotide composition as a test siRNA, but lacking significant homology to the genome. Thus, for example, a scrambled nucleotide sequence of the siRNA may be used, provided it does not display any significant homology to any other gene.

The siRNA molecules of the present disclosure can be transcribed from expression vectors which can facilitate stable expression of the siRNA transcripts once introduced into a host cell. These vectors are engineered to express small hairpin RNAs (shRNAs), which are processed in vivo into siRNA molecules capable of carrying out gene-specific silencing. See, for example, Brummelkamp et al. (2002) Science 296:550-553; Paddison et al (2002) Genes Dev. 16:948-958; Paul et al. (2002) Nature Biotech. 20:505-508; Yu et al. (2002) Proc. Natl. Acad. Sci. USA 99:6047-6052.

Small hairpin RNAs (shRNAs) are single-stranded polynucleotides that form a double-stranded, hairpin loop structure. The double-stranded region is formed from a first sequence that is hybridizable to a target sequence, such as a polynucleotide encoding a lysyl oxidase-type enzyme (e.g., a LOX or LOXL mRNA) and a second sequence that is complementary to the first sequence. The first and second sequences form a double stranded region; while the un-base-paired linker nucleotides that lie between the first and second sequences form a hairpin loop structure. The double-stranded region (stem) of the shRNA can comprise a restriction endonuclease recognition site.

A shRNA molecule can have optional nucleotide overhangs, such as 2-bp overhangs, for example, 3' UU-overhangs. While there may be variation, stem length typically ranges from approximately 15 to 49, approximately 15 to 35, approximately 19 to 35, approximately 21 to 31 bp, or approximately 21 to 29 bp, and the size of the loop can range from approximately 4 to 30 bp, for example, about 4 to 23 bp.

For expression of shRNAs within cells, plasmid vectors can be employed that contain a promoter (e.g., the RNA Polymerase III H1-RNA promoter or the U6 RNA promoter), a cloning site for insertion of sequences encoding the shRNA, and a transcription termination signal (e.g., a stretch of 4-5 adenine-thymidine base pairs). Polymerase III promoters generally have well-defined transcriptional initiation and termination sites, and their transcripts lack poly(A) tails. The termination signal for these promoters is defined by the polythymidine tract, and the transcript is typically cleaved after the second encoded uridine. Cleavage at this position generates a 3' UU overhang in the expressed shRNA, which is similar to the 3' overhangs of synthetic siRNAs. Additional methods for expressing shRNA in mammalian cells are described in the references cited above.

An example of a suitable shRNA expression vector is pSUPER™ (Oligoengine, Inc., Seattle, Wash.), which includes the polymerase-III H1-RNA gene promoter with a well defined transcriptional startsite and a termination signal consisting of five consecutive adenine-thymidine pairs. Brummelkamp et al., supra. The transcription product is cleaved at a site following the second uridine (of the five encoded by the termination sequence), yielding a transcript which resembles the ends of synthetic siRNAs, which also contain nucleotide overhangs. Sequences to be transcribed into shRNA are cloned into such a vector such that they will generate a transcript comprising a first sequence complementary to a portion of a mRNA target (e.g., a mRNA encoding a lysyl oxidase-type enzyme), separated by a short spacer from a second sequence comprising the reverse complement of the first sequence. The resulting transcript folds back on itself to form a stem-loop structure, which mediates RNA interference (RNAi).

Another suitable siRNA expression vector encodes sense and antisense siRNA under the regulation of separate pol III promoters. Miyagishi et al. (2002) Nature Biotech. 20:497-500. The siRNA generated by this vector also includes a five thymidine (T5) termination signal.

siRNAs, shRNAs and/or vectors encoding them can be introduced into cells by a variety of methods, e.g., lipofection. Vector-mediated methods have also been developed. For example, siRNA molecules can be delivered into cell using retroviruses. Delivery of siRNA using retroviruses can provide advantages in certain situations, since retroviral delivery can be efficient, uniform and immediately selects for stable "knock-down" cells. Devroe et al. (2002) BMC Biotechnol. 2:15.

Recent scientific publications have validated the efficacy of such short double stranded RNA molecules in inhibiting target mRNA expression and thus have clearly demonstrated the therapeutic potential of such molecules. For example, RNAi has been utilized for inhibition in cells infected with hepatitis C virus (McCaffrey et al. (2002) Nature 418:38-39), HIV-1 infected cells (Jacque et al. (2002) Nature 418:435-438), cervical cancer cells (Jiang et al. (2002) Oncogene 21:6041-6048) and leukemic cells (Wilda et al. (2002) Oncogene 21:5716-5724).

Methods for Modulating Expression of Lysyl Oxidase-type Enzymes

Another method of modulating the activity of a lysyl oxidase-type enzyme is to modulate the expression of its encoding gene, leading to lower levels of activity if gene expression is repressed, and higher levels if gene expression is activated. Modulation of gene expression in a cell can be achieved by a number of methods.

For example, oligonucleotides that bind genomic DNA (e.g., regulatory regions of a gene encoding a lysyl oxidase-type enzyme) by strand displacement or by triple helix-formation can block transcription, thereby preventing expression of a lysyl oxidase-type enzyme. In this regard, the use of so-called "switch back" chemical linking, in which an oligonucleotide recognizes a polypurine stretch on one strand on one strand of its target and a homopurine sequence on the other strand, has been described. Triple helix formation can also be obtained using oligonucleotides containing artificial bases, thereby extending binding conditions with regard to ionic strength and pH.

Modulation of transcription of a gene encoding a lysyl oxidase-type enzyme can also be achieved, for example, by introducing into the cell a fusion protein comprising a functional domain and a DNA-binding domain, or a nucleic acid encoding such a fusion protein. A functional domain can be, for example, a transcriptional activation domain or a transcriptional repression domain. Exemplary transcriptional activation domains include VP16, VP64 and the p65 subunit of NF-κB; exemplary transcriptional repression domains include KRAB, KOX and v-erbA.

In certain embodiments, the DNA-binding domain portion of such a fusion protein is a sequence-specific DNA-binding domain that binds in or near a gene encoding a lysyl oxidase-type enzyme, or that binds in or near a regulatory region of such a gene. The DNA-binding domain can either naturally bind to a sequence at or near a gene encoding a lysyl oxidase-type enzyme (or its regulatory region), or can be engineered to so bind. For example, the DNA-binding domain can be obtained from a naturally-occurring protein that regulates expression of a gene encoding a lysyl oxidase-type enzyme. Alternatively, the DNA-binding domain can be engineered to bind to a sequence of choice in or near the gene or its regulatory region.

In this regard, the zinc finger DNA-binding domain is useful, inasmuch as it is possible to engineer zinc finger proteins to bind to any DNA sequence of choice. A zinc finger binding domain comprises one or more zinc finger structures. Miller et al. (1985) EMBO J. 4:1609-1614; Rhodes (1993) Scientific American, February: 56-65; U.S. Pat. No. 6,453,242. Typically, a single zinc finger is about 30 amino acids in length and contains four zinc-coordinating amino acid residues. Structural studies have demonstrated that the canonical $(C_2H_2)$ zinc finger motif contains two beta sheets (held in a beta turn which generally contains two zinc-coordinating cysteine residues) packed against an alpha helix (generally containing two zinc coordinating histidine residues).

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and C4 zinc fingers (those in which the zinc ion is coordinated by four cysteine residues). Non-canonical zinc fingers can also include those in which an amino acid other than cysteine or histidine is substituted for one of these zinc-coordinating residues. See e.g., WO 02/057293 (Jul. 25, 2002) and US 2003/0108880 (Jun. 12, 2003).

Zinc finger binding domains can be engineered to have a novel binding specificity, compared to a naturally-occurring zinc finger protein; thereby allowing the construction of zinc finger binding domains engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. Engineering methods include, but are not limited to, rational design and various types of empirical selection methods.

Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,030,215; 7,067,617; U.S. Patent Application Publication Nos. 2002/0165356; 2004/

0197892; 2007/0154989; 2007/0213269; and International Patent Application Publication Nos. WO 98/53059 and WO 2003/016496.

Exemplary selection methods, including phage display, interaction trap, hybrid selection and two-hybrid systems, are disclosed in U.S. Pat. Nos. 5,789,538; 5,925,523; 6,007,988; 6,013,453; 6,140,466; 6,200,759; 6,242,568; 6,410,248; 6,733,970; 6,790,941; 7,029,847 and 7,297,491; as well as U.S. Patent Application Publication Nos. 2007/0009948 and 2007/0009962; WO 98/37186; WO 01/60970 and GB 2,338,237.

Enhancement of binding specificity for zinc finger binding domains has been described, for example, in U.S. Pat. No. 6,794,136 (Sep. 21, 2004). Additional aspects of zinc finger engineering, with respect to inter-finger linker sequences, are disclosed in U.S. Pat. No. 6,479,626 and U.S. Patent Application Publication No. 2003/0119023. See also Moore et al. (2001a) Proc. Natl. Acad. Sci. USA 98:1432-1436; Moore et al. (2001b) Proc. Natl. Acad. Sci. USA 98:1437-1441 and WO 01/53480.

Further details on the use of fusion proteins comprising engineered zinc finger DNA-binding domains are found, for example, in U.S. Pat. Nos. 6,534,261; 6,607,882; 6,824,978; 6,933,113; 6,979,539; 7,013,219; 7,070,934; 7,163,824 and 7,220,719.

Additional methods for modulating the expression of a lysyl oxidase-type enzyme include targeted mutagenesis, either of a gene encoding the lysyl oxidase-type enzyme, or of a regulatory region that controls expression of the gene. Exemplary methods for targeted mutagenesis using fusion proteins comprising a nuclease domain and an engineered DNA-binding domain are provided, for example, in U.S. patent application publications 2005/0064474; 2007/0134796; and 2007/0218528.

Anti-neoplastic Agents

For the purposes of the present disclosure, an "anti-neoplastic agent" is any substance used to treat cancer. This includes treatments to a primary tumor (e.g., to inhibit tumor growth), treatments to reduce invasiveness of a primary tumor, and treatments to inhibit metastasis. Anti-neoplastic agents include chemotherapeutic agents (e.g., small organic molecules, generally with a molecular weight less than 1 kDa), therapeutic proteins (e.g., antibodies, restriction enzyme, tumor suppressor protein) and therapeutic nucleic acids (e.g., DNAs (e.g., triplex-forming olignucleeotide, cDNA encoding an anti-neoplastic agent (e.g., an antibody)) and RNAs (e.g., siRNA, antisense RNA, ribozyme)). Anti-neoplastic agents often, though not exclusively, block one or more aspects of cell growth and/or proliferation (e.g., they can be cytostatic and/or cytotoxic).

The term neoplastic is understood to mean of, relating to, or having the characteristics of a neoplasm. A neoplasm (literally "new growth") is a cell or group of cells that is not subject to normal cellular growth controls. Neoplasms can include benign and malignant tumors, as well as myeloproliferative disorders, in which the neoplastic cells can be dispersed, rather than clustered in a benign mass or tumor. Similarly, neoplasia is the abnormal state characterized by the initiation, growth, development and spread (e.g., metastasis) of a tumor.

As used herein the term "chemotherapeutic agent" or "chemotherapeutic" (or "chemotherapy", in the case of treatment with a chemotherapeutic agent) is meant to encompass any non-proteinaceous (i.e., non-peptidic), non-nucleic acid chemical compound useful in the treatment of cancer.

Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (e.g., bullatacin and bullatacinone); camptothecin (including synthetic analogues topotecan and irinotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phiI1, see, e.g., Angew, Chem. Intl. Ed. Engl., 33: 183--186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubincin (AdramycinTM) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofiran; spirogermanium; tenuazonic acid; triaziquone; 2,2',2"-trichlorotriethylamine; trichothecenes (e.g., T-2 toxin, verracurin A, roridin A and anguidine); urethane; vindesine; dacarbazine; mannomustine; mitobronitol; mitolactol; pipobroman; gacytosine; cytosine arabinoside ("Ara-C"); cyclophosphamide; thiopeta; taxoids, e.g. paclitaxel (TAXOL®, Bristol Meyers Squibb Oncology, Princeton, N.J.) and docetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin (DDP) and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluromethylornithine (DMFO); retinoids such as retinoic acid; capecitabine; and pharmaceutically acceptable salts, acids or derivatives of any of the above.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

In some embodiments, an anti-neoplastic agent is a tyrosine kinase inhibitor. For example, ZD1839 (Iressa™ of AstraZeneca K.K.) shows a competitive effect for ATP in ATP binding site of EGFR (epidermal growth factor receptor) tyrosine kinase, and inhibits tyrosine kinase activity by inhibiting autophosphorylation of tyrosine kinase. Another inhibitor of EGFR tyrosine kinase activity is erlotinib (N-(3-ethynylphenyl)-6,7-bis(2-methoxyethoxy)quinazolin-4-amine). Imatinib mesylate (GLEEVEC™, formerly STI-571) can inhibit the tyrosine kinase activity of both BCR-Abl and c-kit. Sorafenib (Nexavar™) is a small molecular inhibitor of Raf kinase, PDGF (platelet-derived growth factor) VEGF receptor 2 & 3 kinases and c-Kit.

Anti-neoplastic agents can also include therapeutic antibodies, including those raised against tumor antigens or antigens associated with myelodysplasia. Therapeutic antibodies include antibody fragments, as discussed above, monoclonal antibodies, chimeric antibodies and humanized antibodies. Exemplary therapeutic antibodies include the following. IMC-C225 or cetuximab (Erbitux™), is an EGFR-targeted monoclonal antibody that recognizes the receptor portion of EGFR on the cell surface and inhibits the autophosphorylation of EGFR; thereby inhibiting its tyrosine kinase activity. Herceptin (trastuzumab) is a monoclonal antibody directed against the Her2/Neu protein (which is homologous to EGFR and whose overexpression is associated with more aggressive disease and poorer prognosis, particularly in breast cancers). Rituximab (RITUXAN™) is an antibody raised against the CD20 protein on lymphoma cells and which selectively depletes normal and malignant $CD20^+$ pre-B and mature B cells. Alemtuzumab (CAMPATH™) is a monoclonal antibody that specifically targets the CD52 antigen found on B and T lymphocytes; it is used for the treatment of chronic lymphocytic leukemia (CLL) and lymphoma. Gemtuzumab zogamicin (MYLOTARG™) is an antibody conjugate that combines a specific antibody directed against CD33 with a chemotherapeutic drug (zogamicin), and is indicated for the treatment of relapsed adult acute myelocytic leukemia.

Formulations, Kits and Routes of Administration

Therapeutic compositions comprising compounds identified as modulators of one or more lysyl oxidase-type enzymes are also provided. Such compositions typically comprise the modulator and a pharmaceutically acceptable carrier. Supplementary active compounds can also be incorporated into the compositions. Modulators, particularly inhibitors, of lysyl oxidase-type enzymes are useful, for example, in combination with an anti-neoplastic agent, to reduce or eliminate resistance of a malignant cell to the anti-neoplastic agent and for enhancing the cell killing activity of an anti-neoplastic agent. Accordingly, therapeutic compositions as disclosed herein can contain both a modulator of one or more lysyl oxidase-type enzymes and an anti-neoplastic agent. In additional embodiments, therapeutic compositions comprise a therapeutically effective amount of a modulator of one or more lysyl oxidase-type enzymes, but do not contain an anti-neoplastic agent, and the compositions are administered separately from the anti-neoplastic agent. The latter composition can also be used in combination with non-chemotherapeutic treatments such as, for example radiation and surgery.

As used herein, the term "therapeutically effective amount" or "effective amount" refers to an amount of a therapeutic agent that when administered alone or in combination with another therapeutic agent to a cell, tissue, or subject (e.g., a mammal such as a human or a non-human animal such as a primate, rodent, cow, horse, pig, sheep, etc.) is effective to prevent or ameliorate the disease condition or the progression of the disease. A therapeutically effective dose further refers to that amount of the compound sufficient to result in full or partial amelioration of symptoms, e.g., treatment, healing, prevention or amelioration of the relevant medical condition, or an increase in rate of treatment, healing, prevention or amelioration of such conditions. A therapeutically effective amount of, for example, an inhibitor of a lysyl oxidase-type enzyme varies with the type of disease or disorder, extensiveness of the disease or disorder, and size of the mammal suffering from the disease or disorder.

The therapeutic compositions disclosed herein are useful for, inter alia, killing malignant cells and for enhancing the cell killing activity of an anti-neoplastic agent. Accordingly, a "therapeutically effective amount" of a modulator (e.g., inhibitor) of a lysyl oxidase-type enzyme is an amount that results in enhanced cell killing when administered in conjunction with an anti-neoplastic agent. For example, when the inhibitor of a lysyl oxidase-type enzyme is an antibody and the antibody is administered in vivo, normal dosage amounts may vary from about 10 ng/kg to up to 100 mg/kg of mammal body weight or more per day, for example, about 1 g/kg/day to 50 mg/kg/day, optionally about 100 g/kg/day to 20 mg/kg/day, 500 g/kg/day to 10 mg/kg/day, or 1 mg/kg/day to 10 mg/kg/day, depending upon, e.g., body weight, route of administration, severity of disease, etc.

When a modulator of a lysyl oxidase-type enzyme is used in combination with an anti-neoplastic agent, one can also refer to the therapeutically effective dose of the combination, which is the combined amounts of the modulator and the anti-neoplastic agent that result in the killing of malignant cells or reversal of resistance to the anti-neoplastic agent, whether administered in combination, serially or simultaneously. More than one combination of concentrations can be therapeutically effective.

Various pharmaceutical compositions and techniques for their preparation and use are known to those of skill in the art in light of the present disclosure. For a detailed listing of suitable pharmacological compositions and techniques for their administration one may refer to the detailed teachings herein, which may be further supplemented by texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The disclosed therapeutic compositions further include pharmaceutically acceptable materials, compositions or vehicle, such as a liquid or solid filler, diluent, excipient, solvent or encapsulating material, i.e., carriers. These carriers are involved in transporting the subject chemical from one organ, or region of the body, to another organ, or region of the body. Each carrier should be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Another aspect of the present disclosure relates to kits for carrying out the combined administration of a modulator of one or more lysyl oxidase-type enzymes and an anti-neoplastic agent. In one embodiment, the kit comprises an inhibitor of a lysyl oxidase-type enzyme formulated in a pharmaceutical carrier, and at least one anti-neoplastic agent that is not an inhibitor of a lysyl oxidase-type enzyme, formulated as appropriate, in one or more separate pharmaceutical preparations.

The formulation and delivery methods are generally adapted according to the site(s) of malignancy and the type of malignancy to be treated. Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non-systemically, for example, to a tumor or metastasis, reducing the body burden of the composition as compared to systemic delivery. Such local delivery may be achieved through the use of various medically implanted devices including, but not limited to, stents and catheters, or can be achieved by injection or surgery. Methods for coating, implanting, embedding, and otherwise attaching desired agents to medical devices such as stents and catheters are established in the art and contemplated herein.

Implanted stents have been used to carry medicinal agents, such as thrombolytic agents. U.S. Pat. No. 5,163,952 discloses a thermal memoried expanding plastic stent device formulated to carry a medicinal agent in the material of the stent itself. U.S. Pat. No. 5,092,877 discloses a stent of a polymeric material which can have a coating associated with the delivery of compounds. Other patents which are directed to devices of the class utilizing bio-degradable and bio-sorbable polymers include U.S. Pat. No. 4,916,193 and U.S. Pat. No. 4,994,071. By way of example, U.S. Pat. No. 5,304,121 discloses a coating applied to a stent consisting of a hydrogel polymer and a preselected compound such as a cell growth inhibitor or heparin. Methods of making a coated intravascular stent carrying a therapeutic material are described in U.S. Pat. No. 5,464,650 wherein a polymer coating material is dissolved in a solvent and the therapeutic material dispersed in the solvent. The solvent is then evaporated after application.

U.S. Pat. No. 6,120,536 describes additional types of coatings for use with a wide variety of prosthetic devices, including stents. Examples of additional medical or prosthetic devices that are useful for administration of the compositions described herein include, but are not limited to, blood exchanging devices, vascular access ports, central venous catheters, cardiovascular catheters, extracorpeal circuits, vascular grafts, pumps, heart valves, and cardiovascular sutures.

The use of devices coated with the compositions described herein, including stents and catheters, allows the compositions to be delivered to specific or localized sites. Such site-specific delivery can provide a means for use of drugs, and/or dosages thereof, that are not otherwise amenable to systemic delivery due to solubility, systemic toxicity concerns, or other issues. By way of example, β-aminopropionitrile (BAPN) is known to be useful as an inhibitor of lysyl oxidase-type enzymes, but this compound is highly toxic, presenting problems for its effective use when administered systemically. The use of a stent, catheter, or other medical device for delivery of an active agent or compound such as BAPN permits use of the compound at effective dosages in a targeted or localized manner, thus decreasing the systemic toxic effects associated with such compounds.

Indications

The pharmaceutical formulations according to the present disclosure may be used for the prevention and/or treatment of a wide variety of diseases; particularly cancers and malignant disorders, particularly cancers and malignant disorders involving cells that are present in an environment in which a lysyl oxidase-type enzyme is present (e.g., LOX, LOXL2). Both benign and malignant tumors, as well as metastases of a primary tumor, can be treated.

As used herein, "prevention" includes prophylaxis, delay of onset of symptoms or blocking onset of symptoms altogether. As used herein, "treatment," refers to inhibition of progression of a neoplastic disease or malignant disorder, stasis of symptoms, prolongation of survival, partial or full amelioration of symptoms, and partial or full eradication of a neoplastic condition, disease or disorder.

Thus, treatment includes partial or total alleviation of symptoms, or reduction of signs or symptoms of illness, and specifically includes, without limitation, prolongation of survival. The expected progression-free survival times may be measured in months to years, depending on prognostic factors including the number of relapses, stage of disease, and other factors. Prolongation of survival includes without limitation an increase in survival time of at least 1 month, about at least 2 months, about at least 3 months, about at least 4 months, about at least 6 months, about at least 1 year, about at least 2 years, about at least 3 years, or more. Overall survival can also be measured in months to years. The patient's symptoms may remain static or may decrease.

Non-limiting indications that can be treated using the pharmaceutical formulations of the present disclosure include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, liver fibrosis, kidney fibrosis, lung fibrosis, scleroderma, atherosclerosis, repetitive motion disorders, disorders of tissues that are not highly vascularized, and proliferative responses associated with organ transplants.

Generally, cells in a benign tumor retain some or all of their differentiated features and do not divide in a completely uncontrolled manner. A benign tumor is usually localized and nonmetastatic. Specific types of benign tumors that can be treated using the present disclosure include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise in a particular tissue and remain in that tissue (i.e., they remain in situ). A secondary tumor, or metastasis, is a tumor which originates in one region of the body and spreads to another region. Common routes for metastasis of a malignant cell are direct growth into adjacent structures, dissemination through the vascular or lymphatic systems, and tracking along tissue planes and body spaces (peritoneal fluid, cerebrospinal fluid, etc.).

Primary and metastatic tumors that can be treated by the methods disclosed herein include, but are not limited to, lung cancer (including, but not limited to, lung adenocarcinoma, squamous cell carcinoma, large cell carcinoma, bronchioloalveolar carcinoma, non-small-cell carcinoma, small cell carcinoma, mesothelioma); breast cancer (including, but not limited to, ductal carcinoma, lobular carcinoma, inflammatory breast cancer, clear cell carcinoma, mucinous carcinoma); colorectal cancer (including, but not limited to, colon cancer, rectal cancer); anal cancer; pancreatic cancer (including, but not limited to, pancreatic adenocarcinoma, islet cell carcinoma, neuroendocrine tumors); prostate cancer; ovarian carcinoma (including, but not limited to, ovarian epithelial carcinoma or surface epithelial-stromal tumour including serous tumour, endometrioid tumor and mucinous cystadenocarcinoma, sex-cord-stromal tumor); liver and bile duct carcinoma (including, but not limited to, hepatocelluar carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); multiple myeloma; testicular cancer; germ cell tumors; neuroendocrine tumors; cervical cancer; carcinoids of the gastrointestinal tract, breast, and other organs; and signet ring cell carcinoma.

Mesenchymal tumors include, but are not limited to, sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, and leiomysarcoma.

Specific types of cancers or malignant tumors, either primary or secondary, that can be treated using compositions disclosed herein also include, but are not limited to, skin cancer, bone cancer, brain cancer, cancer of the larynx, gall bladder, pancreas, parathyroid, thyroid, adrenal, neural tissue, head and neck, bronchi, basal cell carcinoma, squamous cell carcinoma of both ulcerating and papillary type, metastatic skin carcinoma, osteosarcoma, Ewing's sarcoma, veticulum cell sarcoma, myeloma, giant cell tumor, small-cell lung tumor, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcomas, malignant hypercalcemia, renal cell tumor, polycythermia vera, adenocarcinoma, glioblastoma multiforme, leukemias, lymphomas, malignant melanomas and epidermoid carcinomas.

Hematologic disorders include abnormal growth of blood cells which can lead to dysplastic changes in blood cells and hematologic malignancies such as various leukemias. Examples of hematologic disorders include but are not limited to acute myeloid leukemia (AML), acute promyelocytic leukemia (APML), acute lymphoblastic leukemia (ALL), chronic myelogenous leukemia (CML), the myelodysplastic syndromes (MDS), and sickle cell anemia.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Use of the disclosed methods and compositions for treatment of abnormal cell proliferation due to insults to body tissue during surgery is also contemplated, for a variety of surgical procedures including joint surgery, bowel surgery, and keloid scarring. Diseases that produce fibrotic tissue include emphysema. Repetitive motion disorders that can be treated using the present disclosure include carpal tunnel syndrome.

Proliferative responses associated with organ transplantation that, for example, contribute to transplant rejection and associated complications can also be treated using the methods and compositions of the present disclosure. Specifically, these proliferative responses can occur during transplantation of organs such as the heart, lung, liver, and kidney; as well as following bone marrow or other hematopoietic cell transplantations.

Compositions

Also provided are compositions comprising one or more cells growing in the presence of an extracellular matrix, an anti-neoplastic agent, and, optionally, a test molecule. In certain embodiments, the cells are malignant. In additional embodiments, growth of the malignant cells is resistant to the antiproliferative activity of the anti-neoplastic agent. In additional embodiments, the test molecule is an inhibitor of a lysyl oxidase-type enzyme. In yet additional embodiments, the lysyl oxidase-type enzyme is LOX. In further embodiments, the lysyl oxidase-type enzyme is LOXL2. Such compositions are useful, e.g., for identifying substances that reverse the resistance of the cells to the activity of the anti-neoplastic agent, and for identifying inhibitors of a lysyl oxidase-type enzyme.

The cells can be any type of cell or cell line, including non-human cells or cell lines, either in culture or in situ (e.g., in a primary tumor or metastasis, e.g., in a non-human animal). Malignant cell lines include, for example, HT 1080, a human fibro sarcoma cell line; BT-549, a human breast carcinoma line; MDA-MB435, a human breast adenocarcinoma line; Panc-1, a pancreatic adenocarcinoma cell line; Capan-1, a pancreatic adenocarcinoma cell line; BxPC-3, a pancreatic tumor cell line; HT29, a human colon adenocarcinoma cell line; SKOV3, a human ovarian adenocarcinoma cell line; MDA MB 231, a human breast adenocarcinoma cell line; BT549, a human breast carcinoma cell line; A549, a human lung carcinoma cell line; OVCAR3, a human ovarian adenocarcinoma cell line and MiaPaCa 2, a human pancreatic carcinoma cell line. Exemplary tumor cells are disclosed supra.

Exemplary extracellular matrices and extracellular matrix molecules (e.g., collagen), as well as exemplary anti-neoplastic agents, are disclosed supra. Exemplary test molecules can comprise small organic molecules (e.g., chemotherapeutics), nucleic acids (e.g., siRNA) and polypeptides (e.g., antibodies), for example.

Screening Methods

Also provided herein are methods for assessing the sensitivity of a cell to a test molecule, the methods comprising growing the cell in the presence of an extracellular matrix, contacting the cell with the test molecule, and assaying for cell survival. In certain embodiments, the cell is malignant. In additional embodiments, the extracellular matrix comprises a collagen. In further embodiments, the cell is grown in the presence of an anti-neoplastic agent. In additional embodiments, growth of the cell is resistant to the antiproliferative activity of the anti-neoplastic agent.

In certain embodiments the test molecule is an inhibitor of a lysyl oxidase-type enzyme. In additional embodiments, the lysyl oxidase-type enzyme is LOX. In further embodiments, the lysyl oxidase-type enzyme is LOXL2.

The cells can be any type of cell or cell line, either in culture or in situ (e.g., in a primary tumor or metastasis). Malignant cell lines include, for example, HT 1080, a human fibrosarcoma cell line; BT-549, a human breast carcinoma cell line; MDA-MB435, a human breast adenocarcinoma line; Panc-1, a pancreatic adenocarcinoma cell line; Capan-1, a pancreatic adenocarcinoma cell line; BxPC-3, a pancreatic tumor cell line; HT29, a human colon adenocarcinoma cell line; SKOV3, a human ovarian adenocarcinoma cell line; MDA MB 231, a human breast adenocarcinoma cell line; BT549, a human breast carcinoma cell line; A549, a human lung carcinoma cell line; OVCAR3, a human ovarian adenocarcinoma cell line and MiaPaCa 2, a human pancreatic carcinoma cell line. Exemplary tumor cells are disclosed supra.

Exemplary extracellular matrices and extracellular matrix molecules (e.g., collagen), as well as exemplary anti-neoplastic agents, are disclosed supra. Exemplary test molecules can comprise small organic molecules (e.g., chemotherapeutics), nucleic acids (e.g., siRNA) and polypeptides (e.g., antibodies), for example.

EXAMPLES

Example 1

Sensitivity of Tumor Cells to Chemotherapeutic Agents

This example shows that a number of tumor cell lines are sensitive to various chemotherapeutic agents when grown on standard tissue culture plates. However, when the same cells are grown on tissue culture plates coated with collagen, their sensitivity to the chemotherapeutics is reduced.

Preparation of Collagen-coated Cell Culture Vessels 96-well tissue culture plates coated with collagen Type I were obtained from VWR International (West Chester, Pa.). Alternatively, a 0.5 mg/ml solution of collagen Type I is prepared in 1 mM acetic acid and is filtered through a 0.22 micron membrane. Thirty-three microliters of the collagen solution is added to each well of a 96-well plate. After 30 min, the solution is removed aseptically, and the plate is left to dry in a sterile environment. Plates are stored at 4° C. until use.

Chemotherapeutic Agents

Erlotinib is a small molecule chemotherapeutic that targets Epidermal Growth Factor Receptor 1 (HER1) and that is used for the treatment of non-small cell lung cancer and pancreatic cancer. Cisplatin (cis-diaminedichloroplatinum(II); DDP) causes DNA crosslinks and blocks mitosis and cell division. Methotrexate inhibits dihydrofolate reductase, blocking production of folic acid, a nucleotide precursor and thereby blocking nucleotide synthesis and DNA replication.

Cell Lines and Cell Culture

HT 1080 is a human fibrosarcoma cell line. MDA MB 231 is a human breast adenocarcinoma cell line. BT549 is a human breast carcinoma cell line. MiaPaCa 2 is a human pancreatic carcinoma cell line.

Measurement of Cell Viability in the Presence of Chemotherapeutic Agents

Cells from each of the four aforementioned lines were seeded at 3,000 cells per well in 96-well plates (VWR International, West Chester, Pa.), and cultured in Dulbecco's Modified Eagle's Medium supplemented with 10% fetal bovine serum (DMEM/FBS) at 37° C., 5% $CO_2$ and atmospheric oxygen. Cells were cultured either in untreated wells or in collagen-coated wells, obtained or prepared as described above. Twenty-four hours later, medium was replaced with fresh medium containing various concentrations of erlotinib (LC Laboratories, Woburn, Mass.), cisplatin (Calbiochem, Gibbstown, N.J.) or methotrexate (Calbiochem, Gibbstown, N.J.). After 5 days' culture in the presence of the drug, live cell numbers were determined using the Cell Titer-Glo® luminescent cell viability assay (Promega, San Luis Obispo, Calif.) according to the manufacturer's instructions. For each cell line, three samples were assayed at each drug concentration.

The results are shown in FIGS. 1-12. For all four cell types tested and for three different chemotherapeutic agents, cell viability was sensitive to the chemotherapeutic agents. However, when cultured on collagen-coated tissue culture vessels, the cells were more resistant to killing by all of the chemotherapeutic agents tested. (The apparent resistance of cells cultured on non-collagen-coated wells to high concentrations of certain of the drugs is believed to be due to precipitation of the drug at these higher concentrations.)

Example 2

Effect of siRNA-mediated Reduction of LOX or LOXL2 Levels on Sensitivity of Tumor Cells to Chemotherapeutic Agents This example shows that the resistance to chemotherapeutics, exhibited by tumor cells cultured on collagen, is reversed by reducing levels of LOX or LOXL2 in these cells, using siRNA.

A short RNA molecule, homologous to sequences in the regions near the 3' end of LOX mRNA, was obtained from Invitrogen (Carlsbad, Calif.). The sequence of this LOX siRNA was:

```
ACAGGGAUUGAGUCCUGGCUGUUAU    (SEQ ID NO.: 1)
```

A siRNA homologous to the second SRCR domain of LOXL2 was obtained from Invitrogen (Carlsbad, Calif.) and had the following sequence:

```
UCAACGAAUUGUCAAAUUUGAACCC    (SEQ ID NO.: 2)
```

A control siRNA, containing a proprietary sequence that is represented to be non-homologous to any sequence in the vertebrate trascriptome, was obtained from Invitrogen (Carlsbad, Calif.).

MDA231 cells were seeded at 7,500 cells per well in 96-well plates (VWR International, West Chester, Pa.) in DMEM/FBS at 37° C., 5% $CO_2$ and atmospheric oxygen. Cells were transfected at the time of seeding with 20 µM RNA oligonucleotide, using the Dharmafect transfection reagent according to the manufacturer's instructions (Thermo Scientific, Lafayette, Colo.). Twenty-four hours later, the medium was replaced with medium containing various concentrations of erlotinib (LC Laboratories, Woburn, Mass.). After 5 days continuous exposure to drug, live cell number was determined as described in Example 1. For each condition, (LOX siRNA, LOXL2 siRNA, or non-targeting siRNA), three samples were assayed at each drug concentration. In addition, levels of mRNAs encoding LOX and LOXL 2 were determined in the in the samples transfected with the LOX- and LOXL2-targeted siRNAs, and normalized to levels of RPL19 mRNA (which encodes a ribosomal protein).

For RNA analysis, mRNA was harvested using an RNEasy Mini kit (Qiagen, Valencia, Calif.) according to the manufacturer's instructions. A quantitative PCR reaction was assembled using the Brilliant II Core reagent kit according to the manufacturer's instructions (Agilent Technologies, Cedar Creek, Tex.). The quantitative PCR reaction cycle was as follows: 30 min at 50° C., 10 min at 95° C. and 40 cycles of 15 sec at 95° C. in combination with 1 min at 60° C.

The primer and probe sequences are as follows:

```
                             (SEQ ID NO: 3)
LOXL2 Forward    GGGGTTTGTCCACAGAGCTG (SEQ ID NO: 4)
LOXL2 Reverse    ACGTGTCACTGGAGAAGAGC (SEQ ID NO: 5)
LOXL2 probe      TGGAGCAGCACCAAGAGCCAGTCT (SEQ ID NO: 6)
LOX Forward      CTTGACTGGGGAAGGGTCTG (SEQ ID NO: 7)
LOX Reverse      AAAACGGGGCTCAAATCACG (SEQ ID NO: 8)
LOX Probe        ATCCCACCCTTGGCATTGCTTGGT (SEQ ID NO: 9)
RPL19 Forward    CCGGCTGCTCAGAAGATAC (SEQ ID NO: 10)
RPL19 Reverse    TTCAGGTACAGGCTGTGATACAT (SEQ ID NO: 11)
RPL19 Probe      TGGCGATCGATCTTCTTAGATTCACG
```

Figure 13:
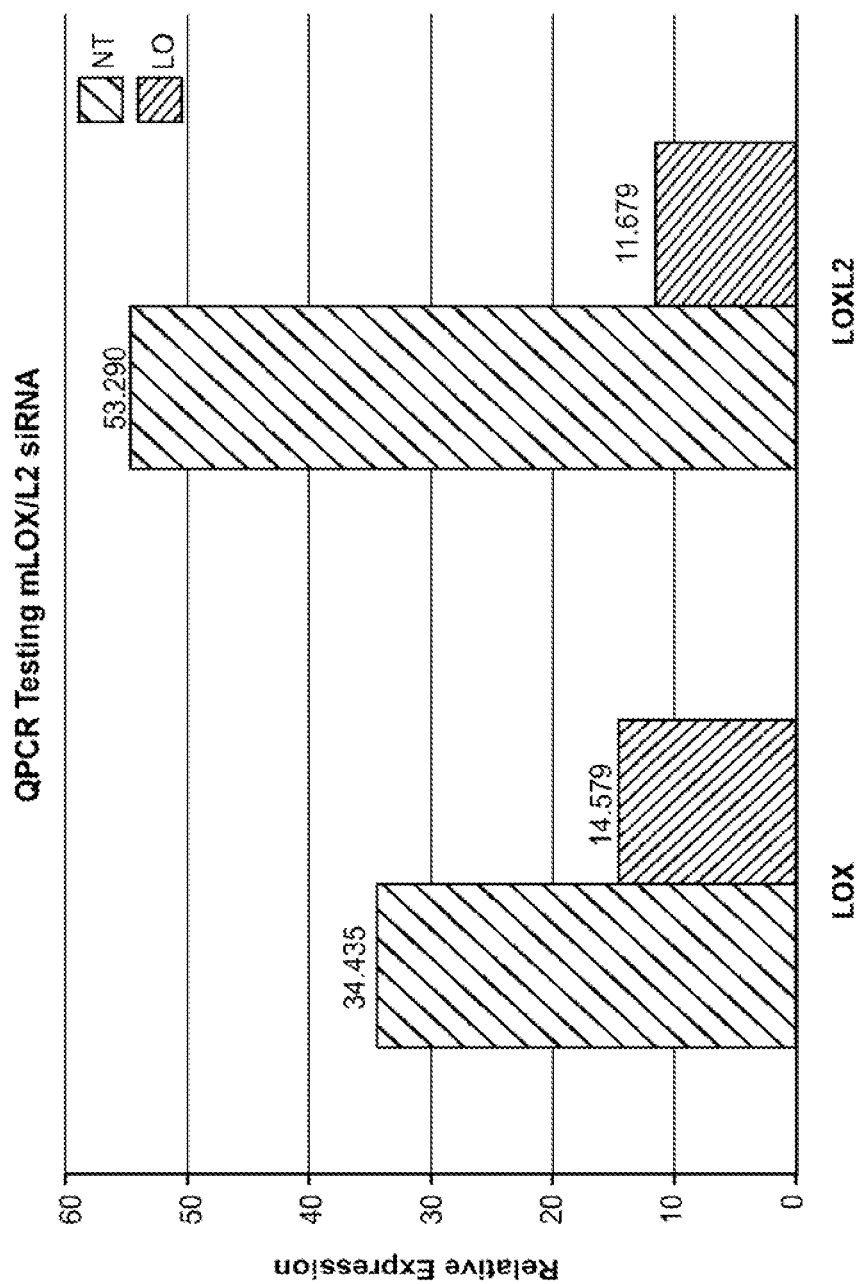
FIG. 13 shows reduction in levels of LOX and LOXL2 mRNA in cells that had been transfected with siRNAs. RNA was purified from MDA 231 cells transfected with a non-targeting siRNA ("NT," left-most of each pair of bars) and from MDA 231 cells that had been transfected ("LO," right-most of each pair of bars) with siRNA targeted to either LOX (left pair of bars) or LOXL2 (right pair of bars). Levels of LOX, LOXL2 and ribosomal protein L19 (RPL19) mRNA were determined by quantitative PCR, and LOX and LOXL2 mRNA levels are expressed relative to RPL19 mRNA levels.
Figure 14:
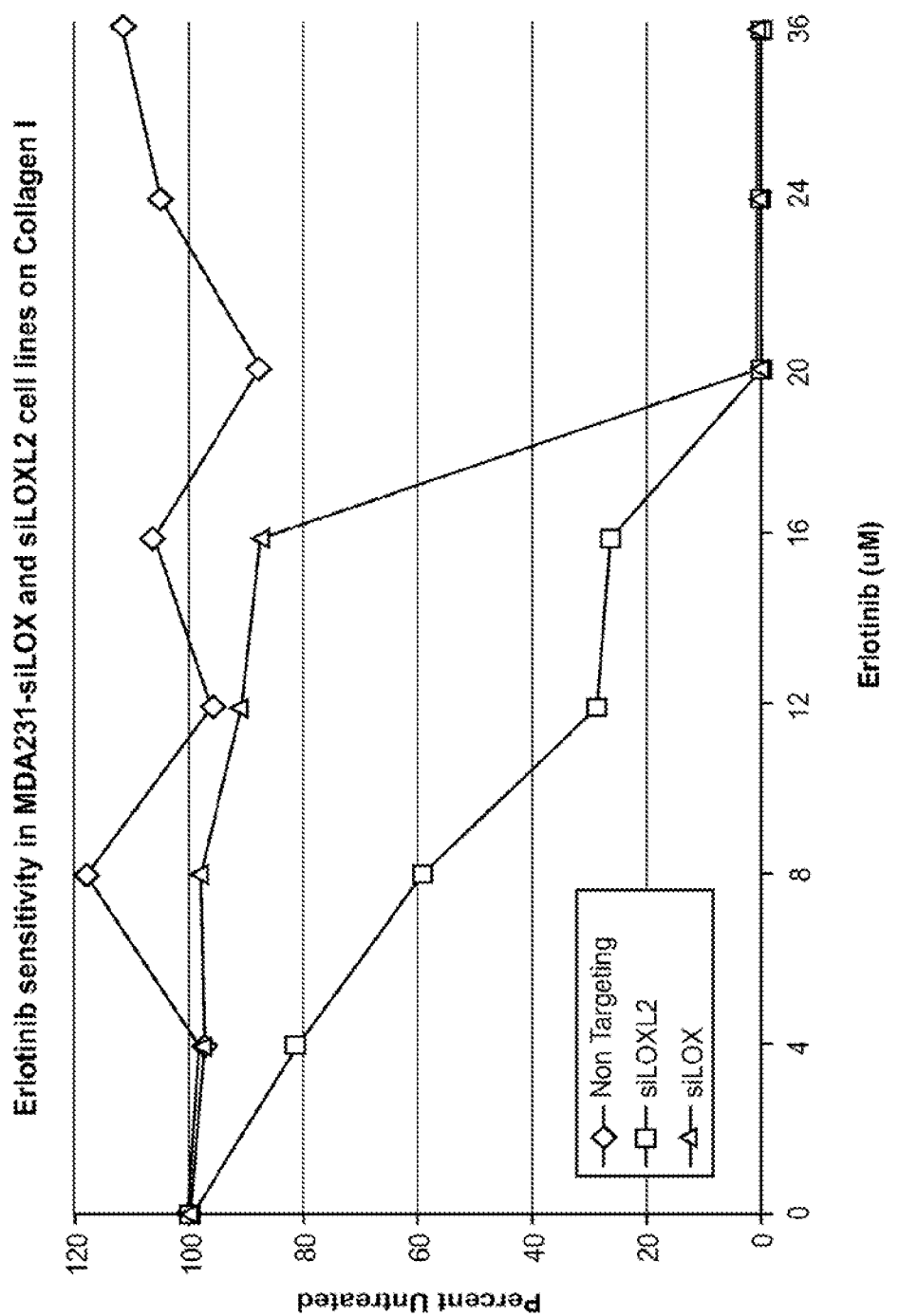
FIG. 14 shows the effect of increasing concentrations of erlotinib on the survival of MDA231 cells cultured in collagen-coated plastic wells. Prior to exposure to erlotinib, cells were transfected with siRNA targeted to LOX (triangles), siRNA targeted to LOXL2 (squares) or with a control siRNA that was not complementary to either LOX or LOXL2 (diamonds).

The results are shown in FIGS. 13 and 14. FIG. 13 shows that levels of LOX mRNA were reduced by over two-fold, and levels of LOXL2 mRNA reduced by almost five-fold, in MDA 231 cells transfected with LOX- and LOXL2-targeted siRNAs, respectively (compared to cells transfected with a non-targeting siRNA). The data shown in FIG. 14 confirms the previous result that MDA 231 cells grown on a collagen matrix (and, in this experiment, transfected with a siRNA that was nonhomologous to LOX or LOXL2) were resistant to killing by erlotinib; and also shows that transfection with siRNA targeted to either LOX or LOXL2, which reduced levels of mRNAs for these proteins (FIG. 13), greatly increased sensitivity of the cells to the drug.

In separate experiments, it was shown that siRNAs targeted to LOX or LOXL2 had little or no effect on sensitivity of MDA 231 cells to erlotinib, when the cells were grown on tissue culture plastic.

These results indicate that cells grown on a collagen substrate are resistant to chemotherapeutic agents, by way of a mechanism that depends on the activity of a lysyl oxidase-type enzyme, and that such resistance can be overcome by inhibiting one or more lysyl oxidase-type enzymes.

Example 3

Inhibition of Lysyl Oxidase-type Enzymes Reverses the Resistance of Breast Carcinoma Cells to Chemotherapeutic Agents This example shows that the resistance to chemotherapeutics, exhibited by BT549 breast carcinoma cells cultured on collagen, is reversed by reducing activity of LOX or LOXL2 in these cells, using antibodies to LOX and LOXL2.

Antibodies to LOX and LOXL2

Monoclonal anti-LOX antibodies M64 and M11 are described in co-owned U.S. Patent Application Publication No. US 2009/0053224 (Feb. 26, 2009), the disclosure of which is incorporated by reference for the purpose of describing these antibodies, their preparation and use.

Monoclonal anti-LOXL2 antibody M20 is described in co-owned U.S. Patent Application Publication No. US 2009/0053224 (Feb. 26, 2009), the disclosure of which is incorporated by reference for the purpose of describing this antibody, its preparation and use. US 2009/0053224 discloses that M20 (also known as AB0023) binds to the SRCR3-4 domain of LOXL2, that M20 is a non-competitive inhibitor of LOXL2 enzymatic activity, and that M20 is a partial inhibitor of LOXL2 enzymatic activity. Also disclosed in US 2009/

0053224 is an antibody having a variable heavy chain region of AB0023: MEWSRVFIFLLSVTAGVHSQVQLQQS-GAELVRPGTSVKVSCKASGYAFTYYLIEWVKQRP GQGLEWIGVINPGSGGTNYNEKFKGKATLTADKSSS TAYMQLSSLTSDDSAVYFCARNWMNFDYWGQGT TLTVSS(SEQ ID NO: 12; sequences of CDR1, CDR2, and CDR3 are underlined and designated SEQ ID NOs: 16-18, respectively). In some embodiments, the antibody has a heavy chain variable region having an amino acid sequence with at least 75% sequence identity to the amino acid sequence set forth in SEQ ID NO: 12. In some embodiments, the antibody is an antibody having a variable light chain region of AB0023: MRCLAEFLGLLVLWIPGAIGDI-VMTQAAPSVSVTPGESVSISCRSSKSLLHSNGNTYLY WFLQRPGQSPQFLIYRMSNLASGVPDRFSGSGSGTA FTLRISRVEAEDVGVYYCMQHLEYPYTFGGGTKLE IK(SEQ ID NO: 13, sequences of CDR1, CDR2, and CDR3 are underlined and designated SEQ ID NOs: 19-21, respectively). In some embodiments, the antibody has a light chain variable region having an amino acid sequence with at least 75% sequence identity to the amino acid sequence set forth in SEQ ID NO: 13. In one embodiment, the antibody is an antibody having the variable heavy chain region set forth in: QVQLVQSGAEVKKPGASVKVSCKASGYAFTYYLIE WVRQAPGQGLEWIGVINPGSGGTNYNEKFKGRATI T ADKSTSTAYMELSSLRSEDTAVYFCARNWMNFDY WGQGTTVTVSS (SEQ ID NO: 14, with the sequences of CDR1, CDR2, and CDR3 are underlined and designated SEQ ID NOs: 22-24, respectively). In some embodiments, the antibody has a heavy chain variable region having an amino acid sequence with at least 75% sequence identity to the amino acid sequence set forth in SEQ ID NO: 14. In some embodiments, the antibody is an antibody having a variable light chain region set forth in: DIVMTQTPLSLSVTPGQPA-SISCRSSKSLLHSNGNTYLYWFLQKPGQSPQFLIY RMSNLASG VPDRFSGSGSGTDFTLKISRVEAED-VGVYYCMQHLEYPYTFGGGTKVEIK (SEQ ID NO: 15, sequences of CDR1, CDR2, and CDR3 are underlined and designated SEQ ID NOs: 25-27, respectively). In some embodiments, the antibody has a light chain variable region having an amino acid sequence with at least 75% sequence identity to the amino acid sequence set forth in SEQ ID NO: 15. In other embodiments, the antibody specifically binds to an epitope having an amino acid sequence set forth as SEQ ID NO: 28 (VRLRGGAYIGEGRVEVLKNGEWGTVCD-DKWDLVSASVVCRELGFGSAKEAVTGSRLGQ GIG-PIHLNEIQCTGNEKSIIDCKFNAESQGC-NHEEDAGVRCNTPAMGLQKKLRLNGGRNPY EGRVEVLVERNGSLVWGMVCGQN-WGIVEAMVVCRQLGLGFASNAFQETWYWHGDVNS NKVVMSGVKCSGTELSLAHCRHDGED-VACPQGGVQYGAGVACS).

Sensitivity of Breast Carcinoma Cells to Chemotherapeutics in the Presence of Lysyl Oxidase Inhibitors One hundred microliters of BT549 cells (a breast carcinoma cell line) were mixed with 250 µg of antibody, seeded at 7,500 cells per well in 96-well plates (VWR International, West Chester, Pa.) and cultured in DMEM/FBS at 37oC and 5% $CO_2$. Twenty-four hours later, the medium was replaced with antibody-containing medium also containing various concentrations of cisplatin (Calbiochem, Gibbstown, N.J.). After a further 5 days, live cell number was determined as described in Example 1. For each cell line and antibody concentration, three samples were assayed at each drug concentration.

Figure 15:
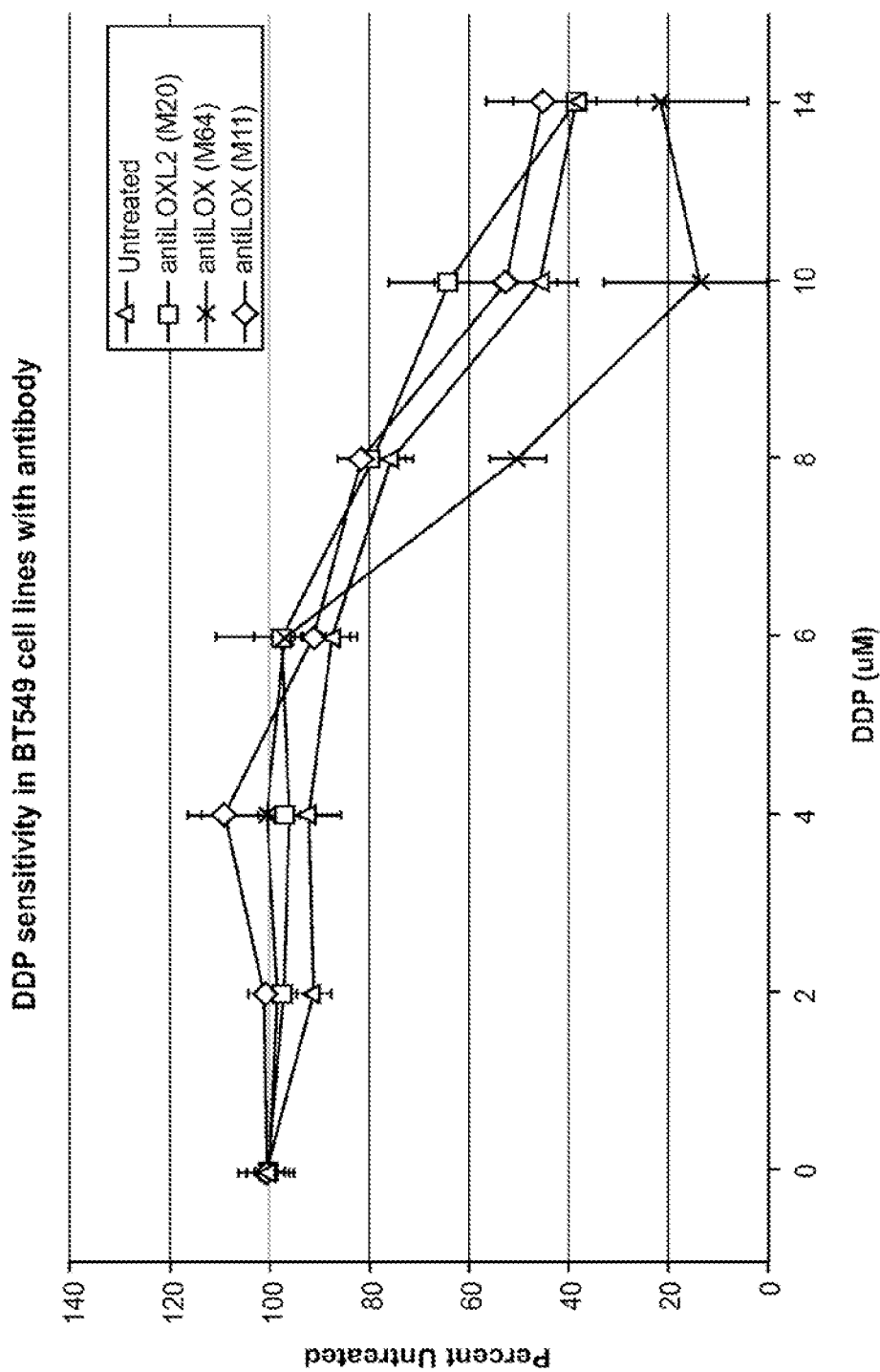
FIG. 15 shows the effect of increasing concentrations of cisplatin (DDP) on the survival of BT549 cells grown on standard tissue culture plastic. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.
Figure 16:
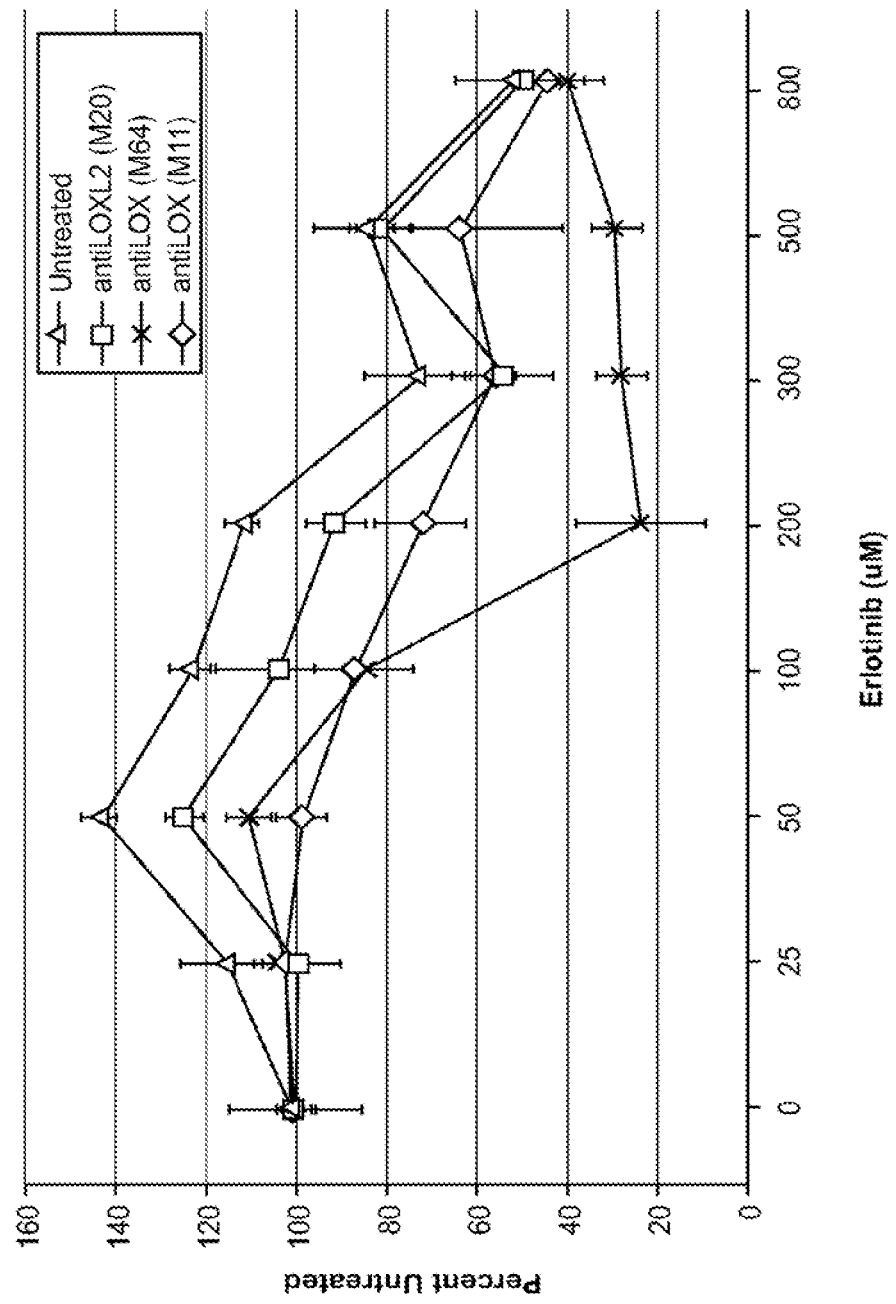
FIG. 16 shows the effect of increasing concentrations of cisplatin (DDP) on the survival of BT549 cells grown on collagen-coated plastic wells. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.

Results are shown in FIGS. 15 and 16. FIG. 15 shows little to no differential sensitivity to cisplatin (DDP) of BT549 cells exposed to anti-LOX or anti-LOXL2 antibodies, compared to control cells, when the cells were grown on standard tissue culture plastic. FIG. 16 shows that, when the cells were grown on collagen, their sensitivity to cisplatin (DDP) in the presence of anti-LOX or anti-LOXL2 antibodies was greater at all cisplatin concentration tested. These results confirm that resistance to chemotherapeutics can be reversed by inhibition of one or more lysyl oxidase-type enzymes.

Example 4

Inhibition of Lysyl Oxidase-type Enzymes Reverses the Resistance of Fibrosarcoma Cells to Chemotherapeutic Agents This example shows that the resistance to chemotherapeutics, exhibited by HT1080 fibrosarcoma cells cultured on collagen, is reversed by reducing activity of LOX or LOXL2 in these cells, using antibodies to LOX and LOXL2.

Antibodies to LOX and LOXL2

Monoclonal anti-LOX antibodies M64 and M11, and monoclonal anti-LOXL2 antibody M20 are described in co-owned U.S. Patent Application Publication No. US 2009/0053224 (Feb. 26, 2009), the disclosure of which is incorporated by reference for the purpose of describing these antibodies, their preparation and use.

Sensitivity of Fibrosarcoma Cells to Chemotherapeutics in the Presence of Lysyl Oxidase Inhibitors One hundred microliters of HT 1080 cells (a fibro sarcoma cell line) were mixed with 250 µg of antibody, seeded at 7,500 cells per well in 96-well plates (VWR International, West Chester, Pa.) and cultured in DMEM/FBS at 37° C. and 5% $CO_2$. Twenty-four hours later, the medium was replaced with antibody-containing medium also containing various concentrations of cisplatin (Calbiochem, Gibbstown, N.J.). After a further 5 days, live cell number was determined as described in Example 1. For each cell line and antibody concentration, three samples were assayed at each drug concentration.

Figure 17:
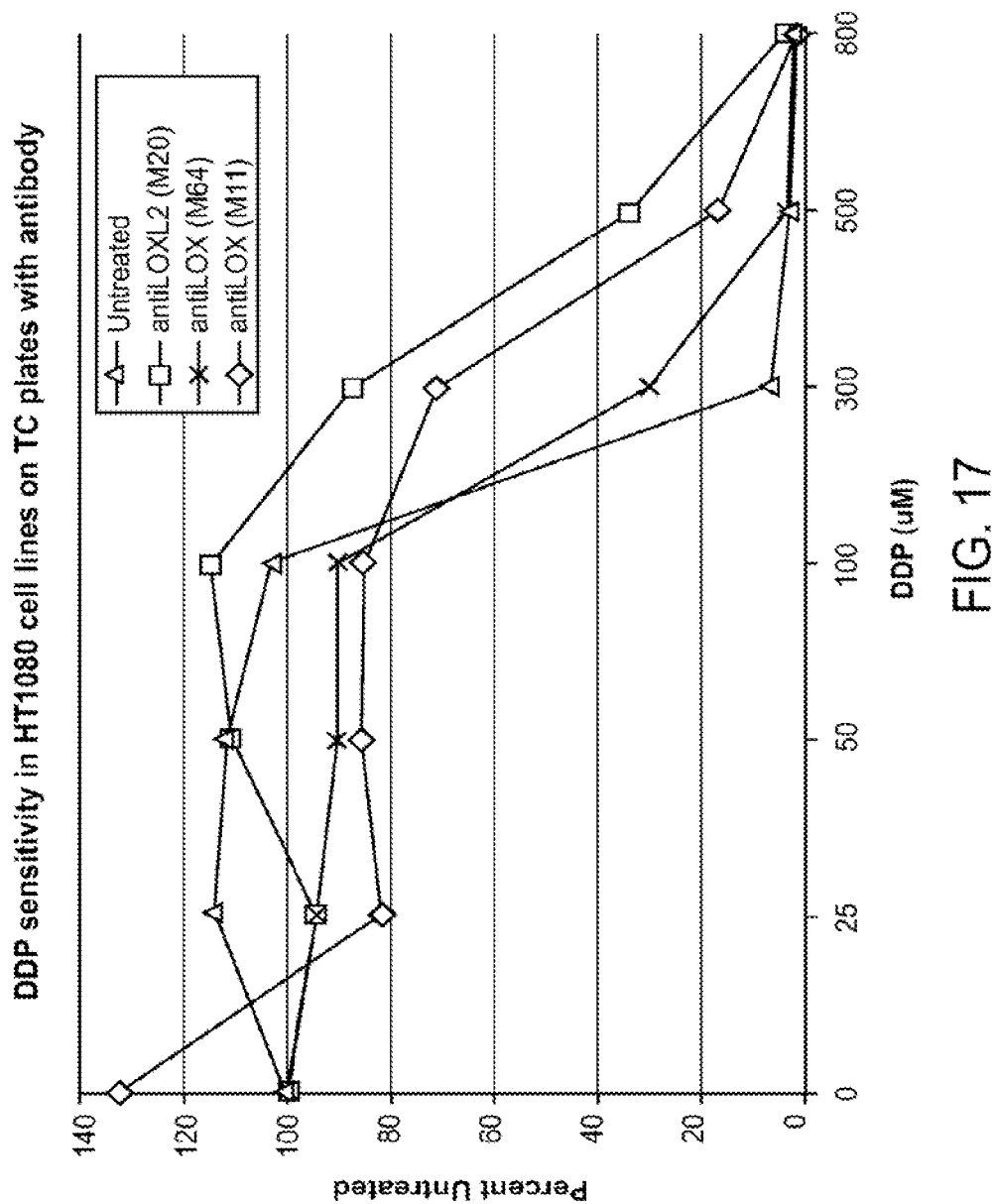
FIG. 17 shows the effect of increasing concentrations of cisplatin (DDP) on the survival of HT1080 cells grown on standard tissue culture plastic. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.
Figure 18:
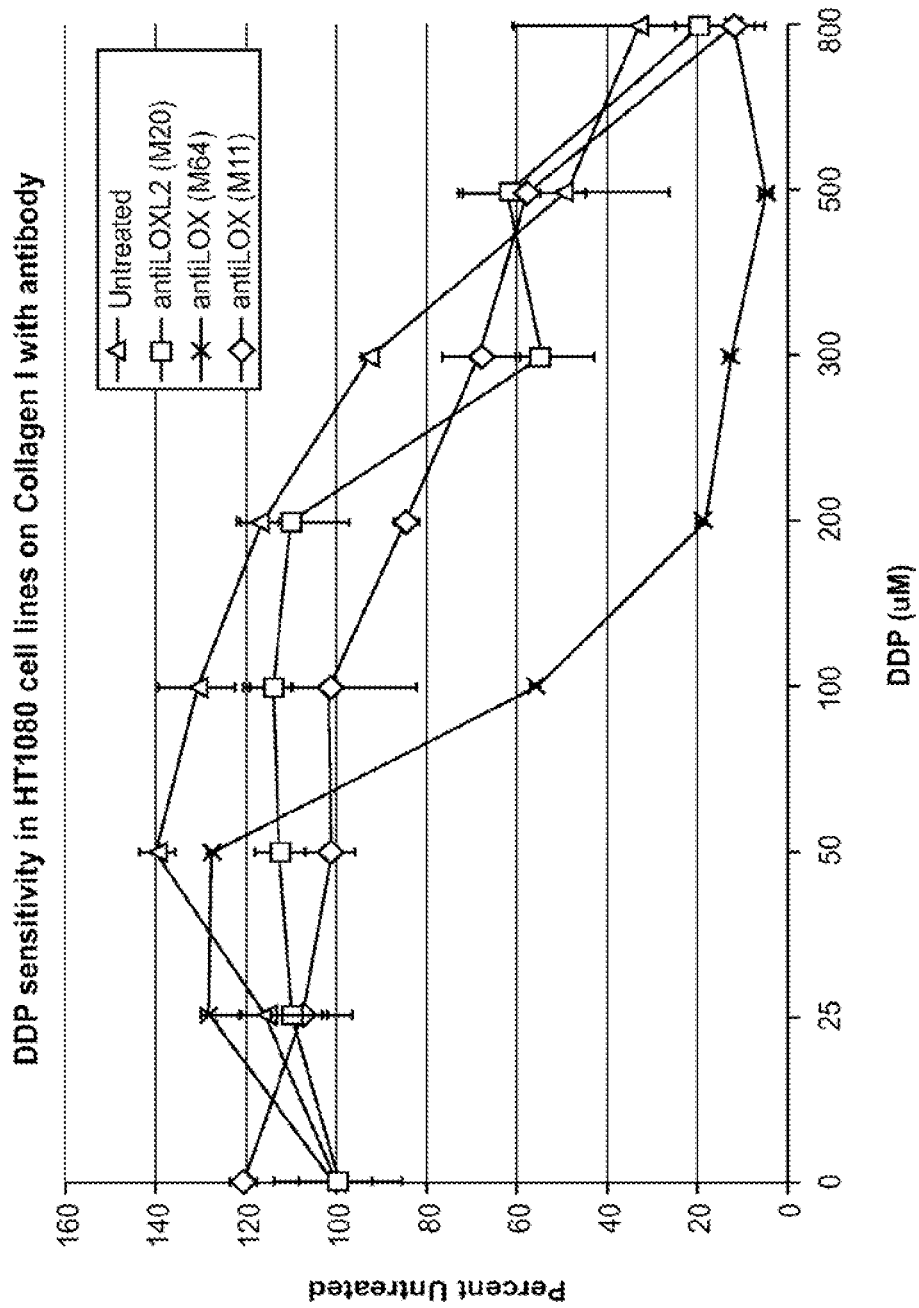
FIG. 18 shows the effect of increasing concentrations of cisplatin (DDP) on the survival of HT1080 cells grown on collagen-coated plastic wells. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.

Results are shown in FIGS. 17 and 18. FIG. 17 shows little to no differential sensitivity to cisplatin (DDP) of HT1080 cells exposed to anti-LOX or anti-LOXL2 antibodies, compared to control cells, when the cells were grown on standard tissue culture plastic. FIG. 18 shows that, when the cells were grown on collagen, their sensitivity to cisplatin (DDP) in the presence of anti-LOX or anti-LOXL2 antibodies was greater at virtually all cisplatin concentration tested. These results provide further confirmation that resistance to chemotherapeutics can be reversed by inhibition of one or more lysyl oxidase-type enzymes.

Example 5

Inhibition of Lysyl Oxidase-type Enzymes Reverses the Resistance of Lung Adenocarcinoma Cells to Chemotherapeutic Agents One hundred microliters of A549 cells (a lung adenocarcinoma cell line) were mixed with 250 µg of anti-LOX or anti-LOXL2 antibody (as above), seeded at 7,500 cells per well in 96-well plates (VWR International, West Chester, Pa.) and cultured in DMEM/FBS at 37° C. and 5% $CO_2$. Twenty-four hours later, the medium was replaced with antibody-containing medium also containing various concentrations of erlotinib (LC Laboratories, Woburn, Mass.). After a further 5 days, live cell number was determined as described in Example 1. For each cell line and antibody concentration, three samples were assayed at each drug concentration.

Figure 19:
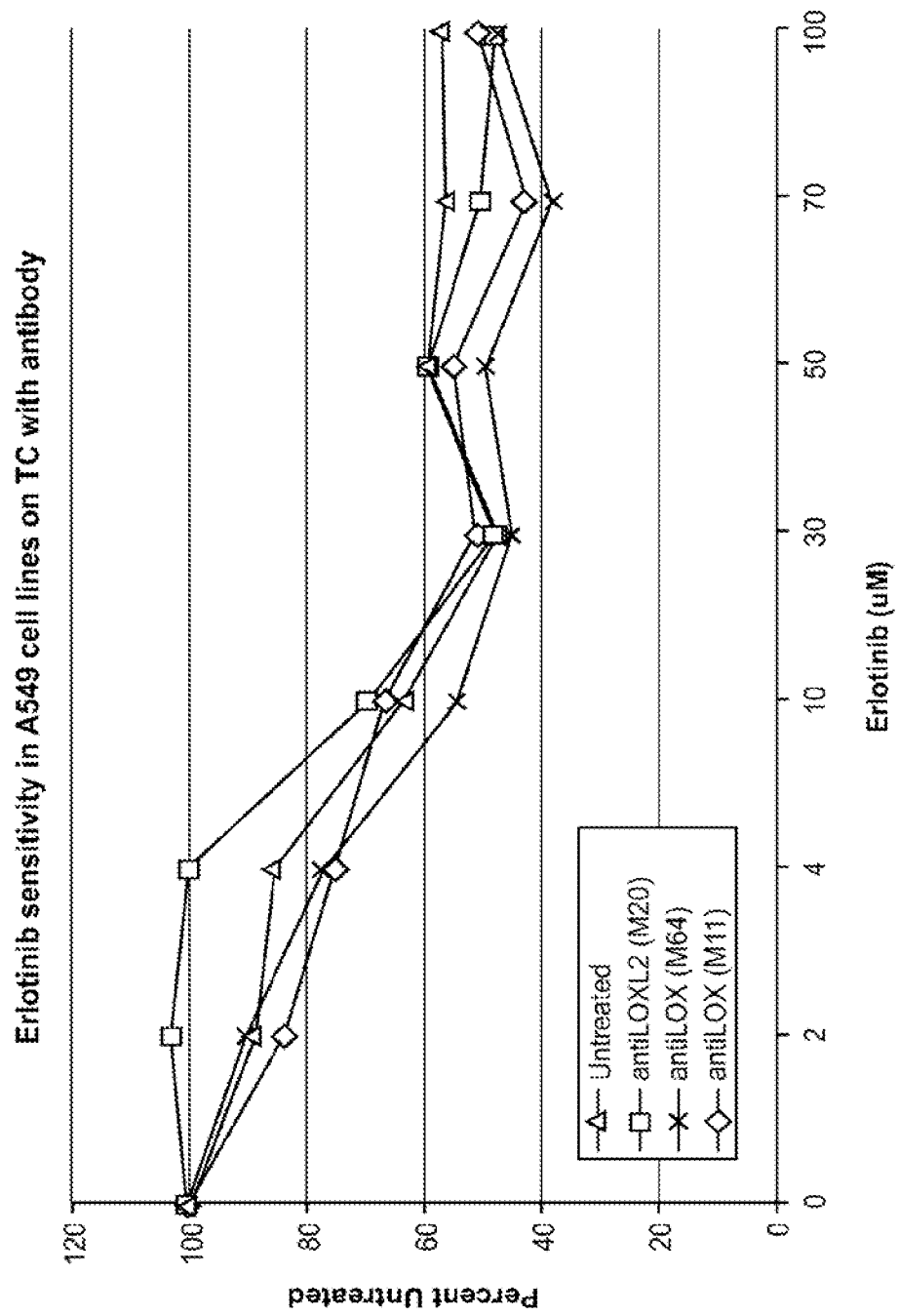
FIG. 19 shows the effect of increasing concentrations of erlotinib on the survival of A549 lung adenocarcinoma cells grown on standard tissue culture plastic. Twenty-four hours prior to exposure to erlotinib, cells were exposed to anti-LOX antibody M11 (diamonds), anti-LOX antibody M64 (X), or anti-LOXL2 antibody M20 (squares). Cells were then exposed to both erlotinib and antibody for an additional five days. Cells not exposed to antibody are indicated by triangles.
Figure 20:
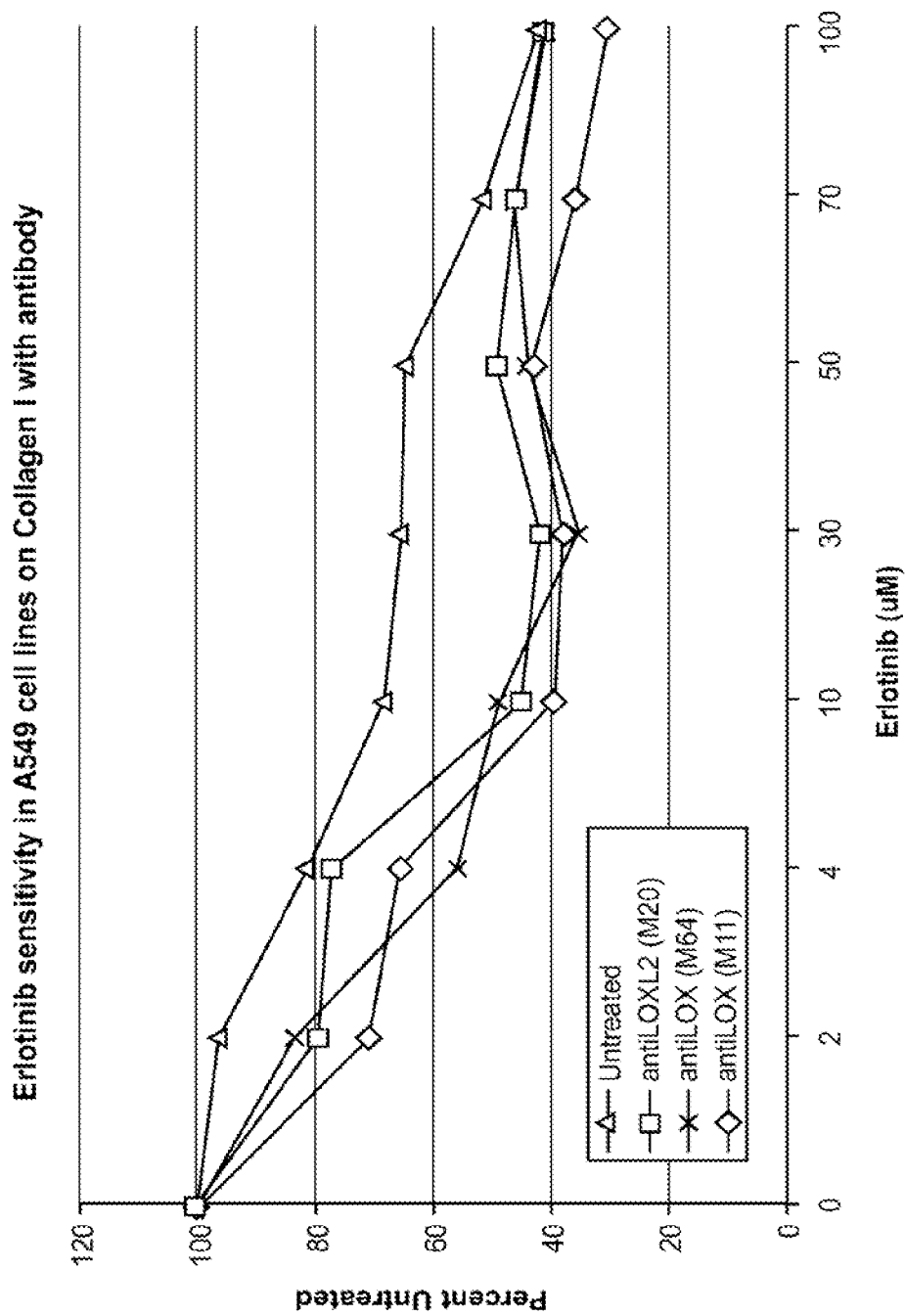
FIG. 20 shows the effect of increasing concentrations of erlotinib on the survival of A549 lung adenocarcinoma cells grown on collagen-coated plastic wells. Twenty-four hours prior to exposure to erlotinib, cells were exposed to anti-LOX antibody M11 (diamonds), anti-LOX antibody M64 (X), or anti-LOXL2 antibody M20 (squares). Cells were then exposed to both erlotinib and antibody for an additional five days. Cells not exposed to antibody are indicated by triangles.

Results are shown in FIGS. 19 and 20. FIG. 19 shows little to no differential sensitivity to erlotinib of A549 cells exposed to anti-LOX or anti-LOXL2 antibodies, compared to control cells, when the cells were grown on standard tissue culture plastic. FIG. 20 shows that, when A549 cells were grown on collagen, their sensitivity to erlotinib in the presence of anti-LOX or anti-LOXL2, antibodies was greater at all erlotinib concentration tested, providing evidence that sensitivity to chemotherapeutics was increased by inhibition of one or more lysyl oxidase-type enzymes.

Example 6

Inhibition of Lysyl Oxidase-type Enzymes Reverses the Resistance of Lung Adenocarcinoma Cells to Chemotherapeutic Agents One hundred microliters of A549 cells (a lung adenocarcinoma cell line) were mixed with 250 µg of anti-LOX or anti-LOXL2 antibody (as above), seeded at 7,500 cells per well in 96-well plates (VWR International, West Chester, Pa.) and cultured in DMEM/FBS at 37° C. and 5% $CO_2$. Twenty-four hours later, the medium was replaced with antibody-containing medium also containing various concentrations of cisplatin (DDP). After a further 5 days, live cell number was determined as described in Example 1. For each cell line and antibody concentration, three samples were assayed at each drug concentration.

Figure 21:
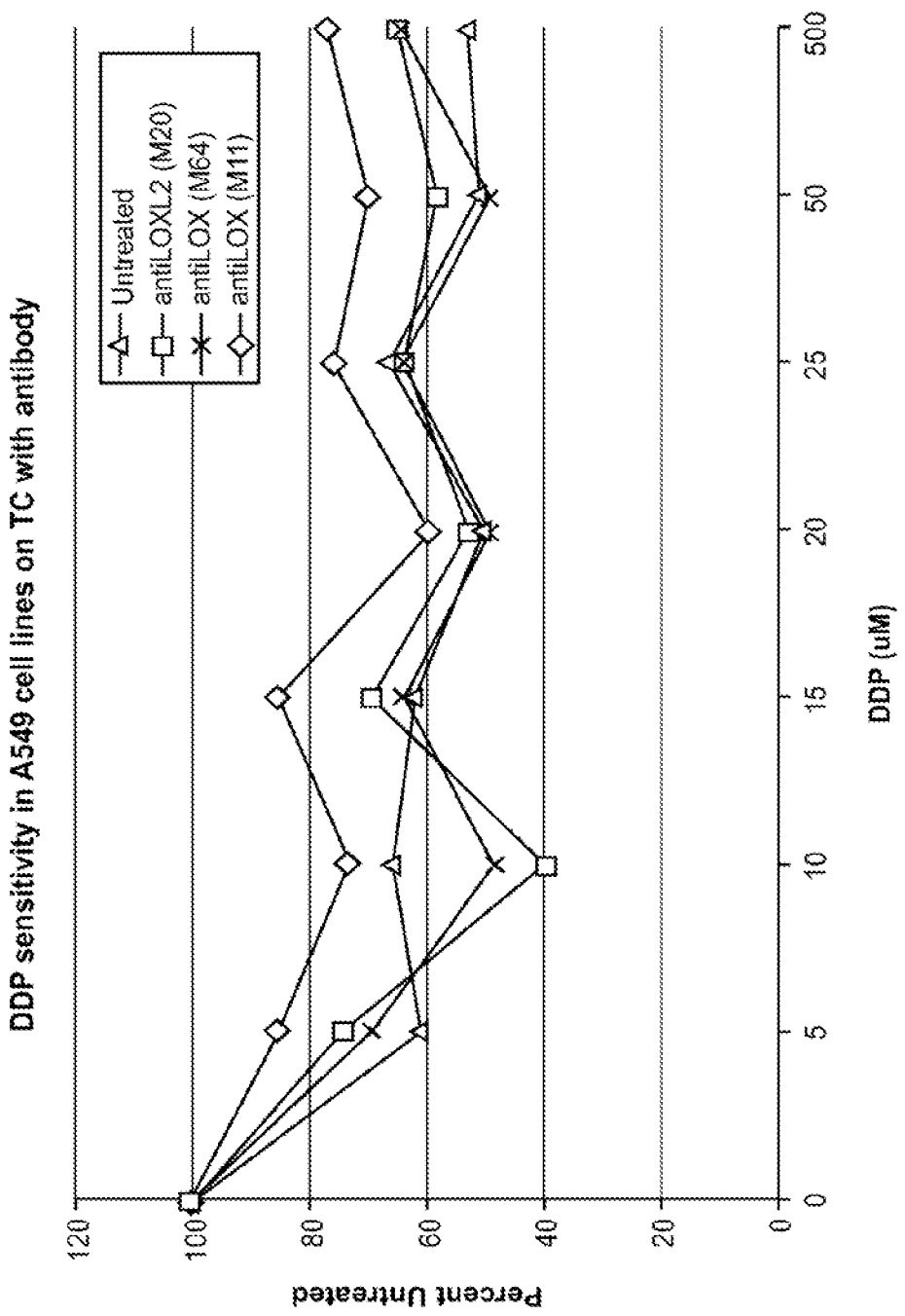
FIG. 21 shows the effect of increasing concentrations of cisplatin (DDP) on the survival of A549 lung adenocarcinoma cells grown on standard tissue culture plastic. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.
Figure 22:
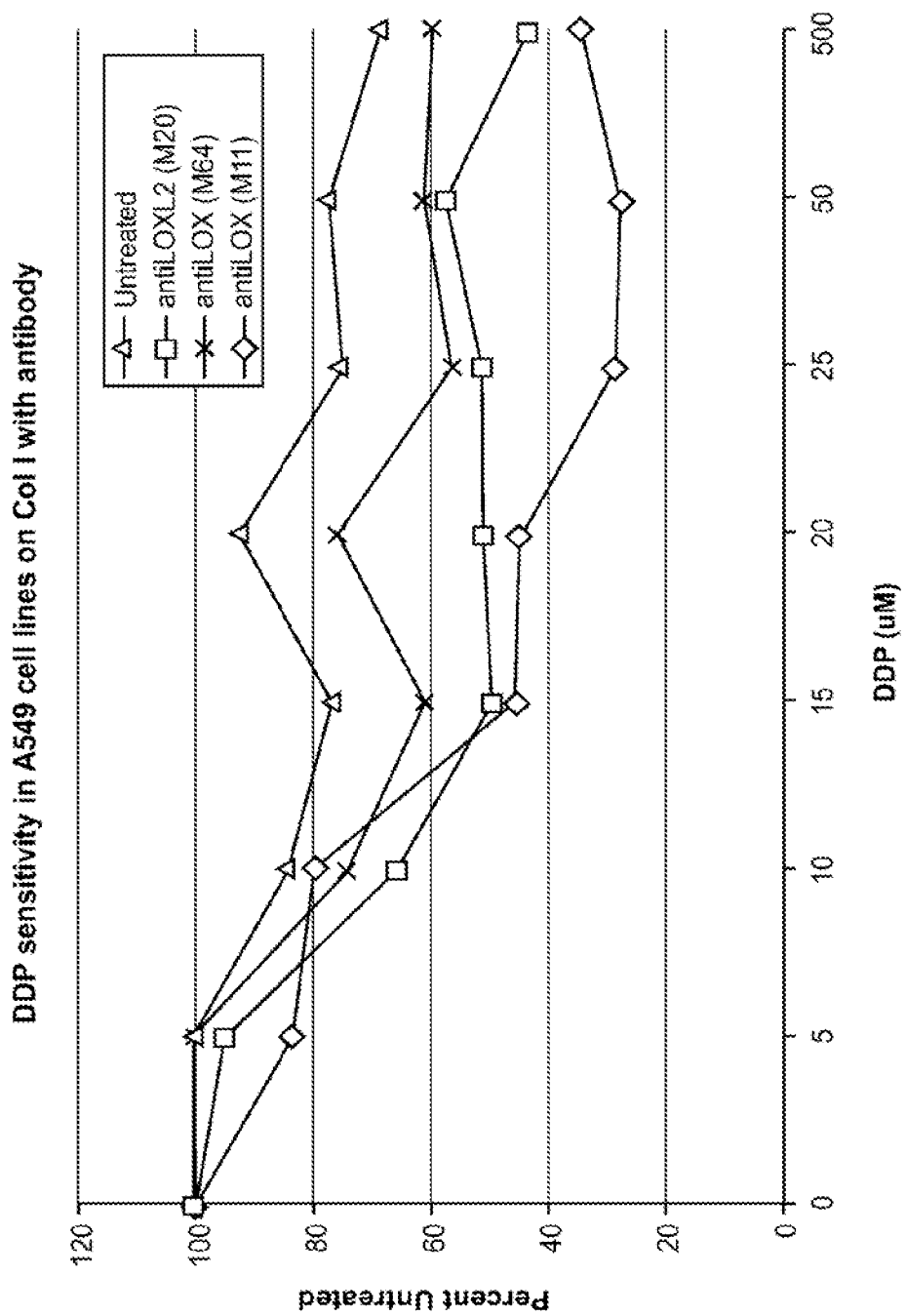
FIG. 22 shows the effect of increasing concentrations of cisplatin (DDP) on the survival of A549 lung adenocarcinoma cells grown on collagen-coated plastic wells. Twenty-four hours prior to exposure to DDP, cells were exposed to anti-LOX antibody M11 (diamonds), anti-LOX antibody M64 (X), or anti-LOXL2 antibody M20 (squares). Cells were then exposed to both DDP and antibody for an additional five days. Cells not exposed to antibody are indicated by triangles.

Results are shown in FIGS. 21 and 22. FIG. 21 shows little to no differential sensitivity to cisplatin (DDP) of A549 cells exposed to anti-LOX or anti-LOXL2 antibodies, compared to control cells, when the cells were grown on standard tissue culture plastic. FIG. 22 shows that, when A549 cells were grown on collagen, their sensitivity to cisplatin in the presence of anti-LOX or anti-LOXL2 antibodies was greater at all cisplatin concentration tested, providing evidence that sensitivity to chemotherapeutics was increased by inhibition of one or more lysyl oxidase-type enzymes.

Example 7

Inhibition of Lysyl Oxidase-type Enzymes Reverses the Resistance of Lung Adenocarcinoma Cells to Chemotherapeutic Agents One hundred microliters of Hs578t cells (a breast cancer cell line) were mixed with 250 µg of anti-LOX or anti-LOXL2 antibody (as above), seeded at 7,500 cells per well in 96-well plates (VWR International, West Chester, Pa.) and cultured in DMEM/FBS at 37° C. and 5% $CO_2$. Twenty-four hours later, the medium was replaced with antibody-containing medium also containing various concentrations of erlotinib (LC Laboratories, Woburn, Mass.). After a further 5 days, live cell number was determined as described in Example 1. For each cell line and antibody concentration, three samples were assayed at each drug concentration.

Figure 23:
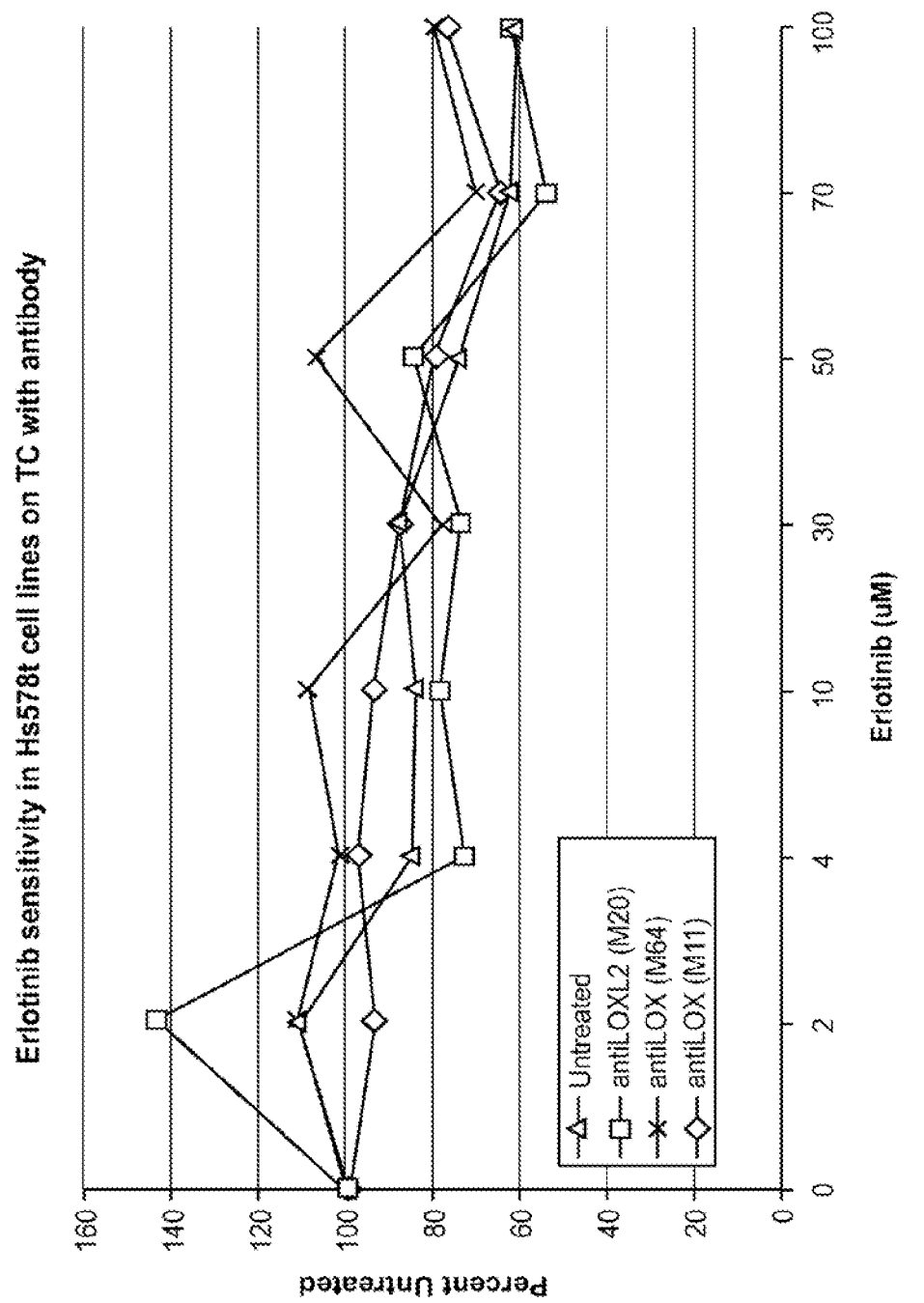
FIG. 23 shows the effect of increasing concentrations of erlotinib on the survival of HS578t breast cancer cells grown on standard tissue culture plastic. Twenty-four hours prior to exposure to erlotinib, cells were exposed to anti-LOX antibody M11 (diamonds), anti-LOX antibody M64 (X), or anti-LOXL2 antibody M20 (squares). Cells were then exposed to both erlotinib and antibody for an additional five days. Cells not exposed to antibody are indicated by triangles.
Figure 24:
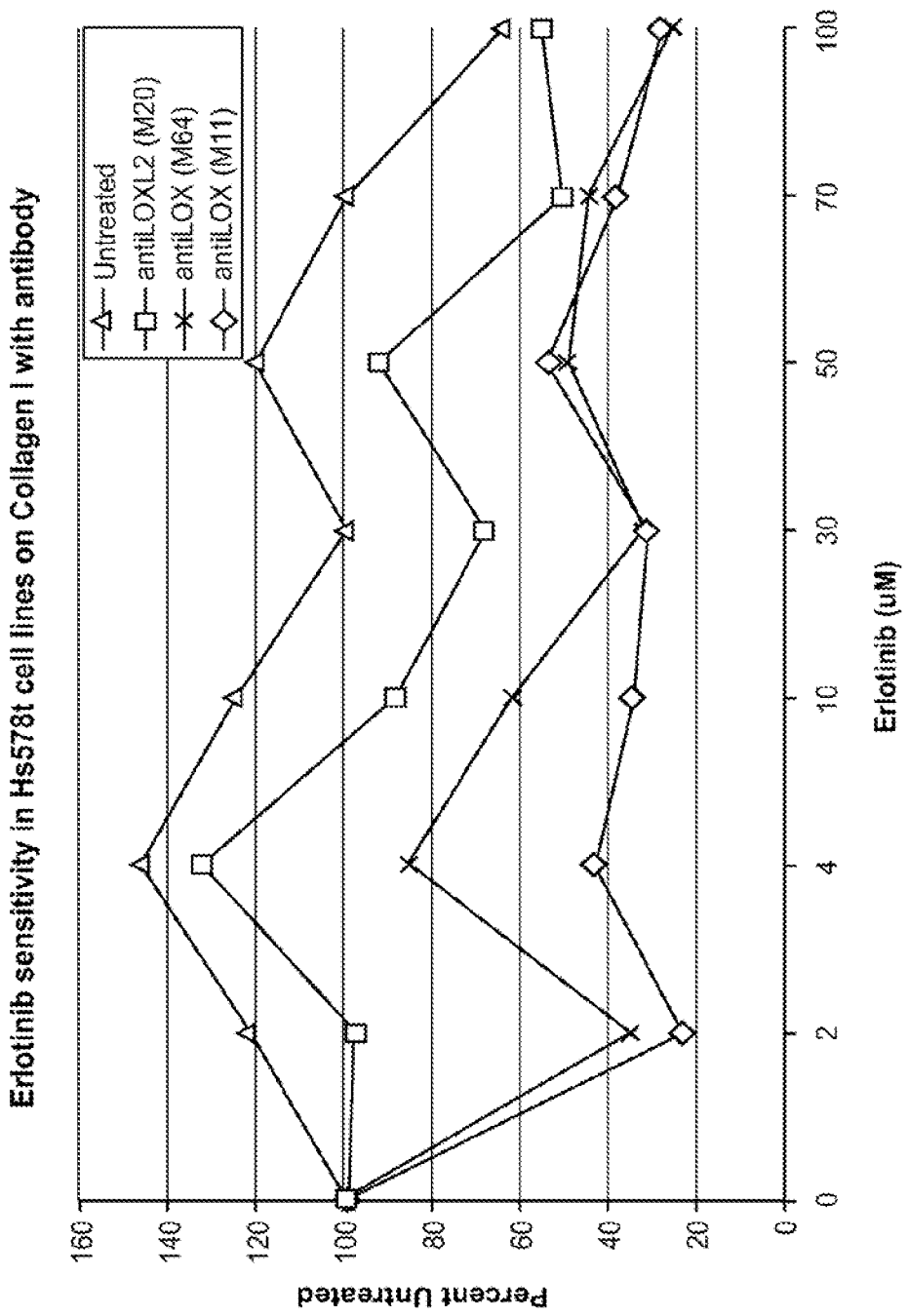
FIG. 24 shows the effect of increasing concentrations of erlotinib on the survival of HS578t breast cancer cells grown on collagen-coated plastic wells. Twenty-four hours prior to exposure to erlotinib, cells were exposed to anti-LOX antibody M11 (diamonds), anti-LOX antibody M64 (X), or anti-LOXL2 antibody M20 (squares). Cells were then exposed to both erlotinib and antibody for an additional five days. Cells not exposed to antibody are indicated by triangles.

Results are shown in FIGS. 23 and 24. FIG. 23 shows little to no differential sensitivity to erlotinib of Hs578t cells exposed to anti-LOX or anti-LOXL2 antibodies, compared to control cells, when the cells were grown on standard tissue culture plastic. FIG. 24 shows that, when Hs578t cells were grown on collagen, their sensitivity to erlotinib in the presence of anti-LOX or anti-LOXL antibodies was greater at all erlotinib concentration tested, providing evidence that sensitivity to chemotherapeutics was increased by inhibition of one or more lysyl oxidase-type enzymes.

Example 8

Inhibition of Lysyl Oxidase-type Enzymes Reverses the Resistance of Breast Adenocarcinoma Cells to Chemotherapeutic Agents MDA-MB-435 cells (breast adenocarcinoma cell lines, ATCC, Manassas, Va.) are resuspended in medium containing 10-50 µg/mL anti-LOXL2 or control IgG antibody. Cells are seeded into 96 well tissue culture plates ($10^3$-$10^4$ cells in 100 µL per well) coated with poly-L-lysine, collagen I, collagen IV, fibronectin, or Matrigel™ (BD Biosciences, San Jose, Calif.). Alternatively, cells are plated in standard 96 well tissue culture plates (Costar, VWR International, West Chester, Pa.). Cells are incubated overnight at 37° C. in a 5% $CO_2$ incubator. After sixteen to twenty hours, various concentrations of cisplatin (DDP), methotrexate, doxorubicin, docetaxel, gemcitabine, or 5-FU are added. Cells are incubated for 3-5 days at 37° C. in a 5% $CO_2$ incubator, and the number of remaining live cells are quantified using the Cell Titer-Glo® luminescent cell viability assay (Promega, Madison, Wis.) according to the manufacturer's instructions. For each condition, samples are assayed in triplicate. The data are analyzed using GraphPad Prism software (or equivalent) to calculate $IC_{50}$ values from a 4-parameter logistic equation.

The results indicate that MDA-MB-435 cells exhibit increased sensitivity to cisplatin (DDP), methotrexate, doxorubicin, docetaxel, gemcitabine, and 5-FU in the presence of anti-LOXL2 antibodies, when plated on different extracellular matrices. For example, MDA-MB-435 cells exhibit increased sensitivity to various chemotherapeutic drugs, in the presence of anti-LOXL2 antibodies, when grown on collagen I. Furthermore, under certain conditions, MDA-MB-435 cells can demonstrate differential sensitivity to chemotherapeutics on different substrates. For example, increased drug resistance is observed on collagen I compared to collagen IV or Matrigel™, reflecting the relevance of matrices associated with a disease state such as cancer (collagen I) compared to matrices associated with a healthy organ (collagen IV, Matrigel™), and this resistance is reduced by anti-LOXL2 treatment. These data provides evidence that sensitivity to chemotherapeutic agents can be increased by inhibition of a lysyl oxidase-type enzyme.

Example 9

Inhibition of Lysyl Oxidase-type Enzymes Reverses the Resistance of Pancreas Adenocarcinoma Cells to Chemotherapeutic Agents Panc-1 or Capan-1 cells (pancreas adenocarcinoma cell lines, ATCC, Manassas, Va.) are resuspended in medium containing 10-50 µg/mL anti-LOXL2 or control IgG antibody. Cells are seeded into 96 well tissue culture plates ($10^3$-$10^4$ cells in 100 µL per well) coated with poly-L-lysine, collagen I, collagen IV, fibronectin, or Matrigel™ (BD Biosciences, San Jose, Calif.). Alternatively, cells are plated in standard 96 well tissue culture plates (Costar, VWR International, West Chester, Pa.). Cells are incubated overnight at 37° C. in a 5% $CO_2$ incubator. After sixteen to twenty hours, various concentrations of gemcitabine, docetaxel, doxorubicin, 5-FU or erlotinib are added. Cells are incubated for 3-5 days at 37° C. in a 5% $CO_2$ incubator, and the number of remaining live cells are quantified using the Cell Titer-Glo® luminescent cell viability assay (Promega, Madison, Wis.) according to the manufacturer's instructions. For each condition, samples are assayed in triplicate. The data are analyzed using GraphPad Prism software (or equivalent) to calculate $IC_{50}$ values from a 4-parameter logistic equation.

The results indicate that Panc-1 and Capan-1 cells exhibit increased sensitivity to gemcitabine, docetaxel, doxorubicin, 5-FU or erlotinib in the presence of anti-LOXL2 antibodies when plated on different extracellular matrices. For example, Panc-1 and Capan-1 cells exhibit increased sensitivity to various chemotherapies in the presence of anti-LOXL2 antibodies when grown on collagen I. Furthermore, under certain conditions, Panc-1 and Capan-1 cells can demonstrate differential sensitivity to chemotherapies on different substrates. For example, increased drug resistance is observed on collagen I compared to collagen IV or Matrigel™ reflecting the relevance of matrices associated with a disease state such as cancer (collagen I) compared to matrices associated with a healthy organ (collagen IV, Matrigel™), and this resistance is reduced by anti-LOXL2 treatment. These data provides evidence that sensitivity to chemotherapeutic agents can be increased by inhibition of a lysyl oxidase-type enzyme.

Applicants have shown that sensitivity to a number of different chemotherapeutic agents, each with a different mechanism of action, was increased by inhibition of one or more lysyl oxidase-type enzymes. This effect has been observed in at least six different malignant cell lines of different etiology and tissue origin.

What is claimed is:

1. A method for killing a malignant cell, the method comprising: contacting the malignant cell, wherein the malignant cell expresses a lysyl oxidase-type enzyme, with an anti-neoplastic agent and an inhibitor of the lysyl oxidase-type enzyme, wherein the cell is growing in the presence of an extracellular matrix containing collagen, whereby the malignant cell is killed, wherein the anti-neoplastic agent is a chemotherapeutic agent and the inhibitor is an isolated lysyl oxidase-like 2 (LOXL2) antibody or antigen-binding fragment thereof specifically binds to an epitope within the amino acid sequence of SEQ ID NO: 28; wherein the antibody or antigen-binding fragment thereof comprises a heavy chain variable region comprising the amino acid sequence of SEQ ID NO: 14 and a light chain variable region comprising the amino acid sequence of SEQ ID NO: 15.

2. The method of claim herein the malignant cell is in culture.

3. The method of claim 1, wherein the malignant cell is present in a tumor.

4. The method of claim 1, wherein the chemotherapeutic agent is selected from the group consisting of methotrexate, cispiatin, doxorubicin, docetaxel, erlotinih, paciitaxel, para-clitaxel, 5-fluorouracil and germcitibine.

5. The method of claim 1, wherein the collagen comprises type 1 collagen.

6. The method of claim 1, wherein the LOXL2 antibody or antigen-binding fragment thereof is a Fv, a scFv, a Fab, or a F(ab')$_2$.

7. The method of claim 1, wherein the LOXL2 inhibitor inhibits LOXL2 enzymatic activity.

8. The method of claim 1, wherein the LOXL2 antibody or antigen-binding fragment thereof is polyclonal.

9. The method of claim 1, wherein the antibody or antigen-binding fragment thereof is monoclonal.

10. The method of claim 9, wherein the antibody or antigen-binding fragment thereof is humanized.

11. The method of claim 1, wherein the antibody or antigen-binding fragment thereof comprises the complementarity determining regions CDRs), CDR1, CDR2, and CDR3, of a heavy chain variable region comprising the amino acid sequence of SEQ ID NO; 14, and the CDRs, CDR1, CDR2, and CDR3, of a light chain variable region comprising the amino acid sequence of SEQ ID NO: 15.

12. The method of claim 11, wherein the antibody or antigen-binding fragment thereof comprises a heavy chain variable region comprising the amino acid sequence of SEC) ID NO: 14.

13. The method of claim 11, wherein the antibody or antigen-binding fragment thereof comprises a light chain variable region comprising the amino acid sequence of SEQ ID NO; 15.

14. The method of claim 1, wherein the malignant cell is selected from the group consisting of fibrosarcoma, breast carcinoma, breast adenocarcinoma, pancreatic adenocarcinoma, pancreatic tumor, colon adenocarcinoma, ovarian adenocarcinoma, and lung carcinoma.

* * * * *